(12) United States Patent
Boerner et al.

(10) Patent No.: US 10,919,921 B2
(45) Date of Patent: Feb. 16, 2021

(54) P-CHIRAL PHOSPHINE LIGANDS AND USE THEREOF FOR ASYMMETRIC SYNTHESIS

(71) Applicant: BASF SE, Ludwigshafen am Rhein (DE)

(72) Inventors: Armin Boerner, Rostock (DE); Jens Holz, Rostock (DE); Katharina Rumpel, Rostock (DE)

(73) Assignee: BASF SE

(*) Notice: Subject to any disclaimer, the term of this patent is extended or adjusted under 35 U.S.C. 154(b) by 0 days.

(21) Appl. No.: 16/099,324

(22) PCT Filed: May 5, 2017

(86) PCT No.: PCT/EP2017/060800
§ 371 (c)(1),
(2) Date: Nov. 6, 2018

(87) PCT Pub. No.: WO2017/191310
PCT Pub. Date: Nov. 9, 2017

(65) Prior Publication Data
US 2019/0211040 A1    Jul. 11, 2019

(30) Foreign Application Priority Data

May 6, 2016   (EP) ..................................... 16168649
Jun. 13, 2016  (EP) ..................................... 16174225

(51) Int. Cl.
| | | |
|---|---|---|
| *C07F 9/655* | (2006.01) | |
| *C07F 9/50* | (2006.01) | |
| *C07C 45/62* | (2006.01) | |
| *C07F 15/00* | (2006.01) | |
| *C07F 9/6584* | (2006.01) | |
| *C07F 9/46* | (2006.01) | |
| *C07F 9/6558* | (2006.01) | |
| *B01J 31/24* | (2006.01) | |
| *C07C 29/141* | (2006.01) | |
| *C07C 29/17* | (2006.01) | |

(52) U.S. Cl.
CPC ........... *C07F 9/65522* (2013.01); *B01J 31/24* (2013.01); *C07C 29/141* (2013.01); *C07C 29/17* (2013.01); *C07C 45/62* (2013.01); *C07F 9/46* (2013.01); *C07F 9/5022* (2013.01); *C07F 9/65517* (2013.01); *C07F 9/65586* (2013.01); *C07F 9/65844* (2013.01); *C07F 15/0073* (2013.01); *C07B 2200/07* (2013.01); *C07C 2601/14* (2017.05)

(58) Field of Classification Search
CPC .................................................. C07F 9/65522
See application file for complete search history.

(56) References Cited

U.S. PATENT DOCUMENTS

| | | |
|---|---|---|
| 4,237,072 A | 12/1980 | Aviron-Violet et al. |
| 7,534,921 B2 | 5/2009 | Jäkel et al. |
| 7,973,198 B2 | 7/2011 | Schmidt-Leithoff et al. |
| 2013/0331611 A1 | 12/2013 | Saudan et al. |

FOREIGN PATENT DOCUMENTS

| | | |
|---|---|---|
| CN | 102000606 A | 4/2011 |
| CN | 103384657 A | 11/2013 |
| CN | 103797020 A | 5/2014 |
| JP | S52078812 A | 7/1977 |
| WO | WO-2006040096 A1 | 4/2006 |
| WO | WO-2008132057 A1 | 11/2008 |
| WO | WO-2012150053 A1 | 11/2012 |
| WO | WO-2013007724 A1 | 1/2013 |
| WO | WO-2014167014 A1 | 10/2014 |

OTHER PUBLICATIONS

Juge, S., et al. "Efficient Stereoselective Synthesis of o-Functionalized P-Chirogenic Phosphines Applied to Asymmetric Catalysis." Phosphorous, Sulfur, and Silicon and the related Elements. (2015), vol. 190, No. 5-6, pp. 700-705. (Year: 2015).*
Holz, J., et al. "P-Chirogenic Xantphos Ligands and Related Ether Diphosphines: Synthesis and Application in Rhodium-Catalyzed Asymmetric Hydrogenation." ACS Catal. (2017), vol. 7, pp. 6162-6169. (Year: 2017).*
Bayardon, J., et al., "Efficient Steroselective Synthesis of o-Functionalized P-Chirogenic Phosphines Applied to Asymmetric Catalysis", Phosphorus, Sulfur and Silicon and the related Elements, vol. 190, No. 5-6, (2015), pp. 700-705.
Chapuis, C., et al., "Synthesis of Citronellal by Rh$^1$-Catalysed Asymmetric Isomerization of N,N-Diethyl-Substituted Geranyl- and Nerylamines or Geraniol and Nerol in the Presence of Chiral Diphosphino Ligands under Homogeneous and Supported Conditions", Helvetica Chimica Acta, vol. 84, No. 1, (2001), pp. 230-242.
Dang, T.-P., et al., "Catalyse d'Hydrogenation en Phase Homogene des Aldehydes α-β Insatures. Application a la Synthese Asymetrique du Citronellal", Journal of Molecular Catalysis, vol. 16, No. 1, (1982), pp. 51-59 (in French).
International Search Report for PCT/EP2017/060800 dated Jul. 17, 2017.
Written Opinion of the International Searching Authority for PCT/EP2017/060800 dated Jul. 17, 2017.

(Continued)

*Primary Examiner* — John S Kenyon
(74) *Attorney, Agent, or Firm* — Faegre Drinker Biddle & Reath LLP

(57) ABSTRACT

The present invention relates to chiral compounds with two optically active phosphorus atoms, chiral transition metal catalysts which comprise these compounds as ligands, a process for preparing the P-chiral compounds and processes for asymmetric synthesis using the chiral transition metal catalysts. The present invention specifically relates to a process for preparing an optically active carbonyl compound by asymmetric hydrogenation of a prochiral α,β-unsaturated carbonyl compound with hydrogen in the presence of an optically active transition metal catalyst according to the invention. Yet more specifically, the present invention relates to a process for the asymmetric hydrogenation of citral, and also a process for preparing optically active menthol.

18 Claims, No Drawings

(56) References Cited

OTHER PUBLICATIONS

Clavero et al., "Ruthenium complexes of P-stereogenic phosphines with a heterocyclic substituent", Dalton Trans., vol. 45, No. 20, May 28, 2016, pp. 8513-8531.

* cited by examiner

P-CHIRAL PHOSPHINE LIGANDS AND USE THEREOF FOR ASYMMETRIC SYNTHESIS

CROSS-REFERENCE TO RELATED APPLICATIONS

This application is a national stage application (under 35 U.S.C. § 371) of PCT/EP2017/060800, filed May 5, 2017, which claims benefit of European Application Nos. 16168649.8, filed May 6, 2016, and 16174225.9, filed Jun. 13, 2016, all of which are incorporated herein by reference in their entirety.

BACKGROUND OF THE INVENTION

The present invention relates to chiral compounds with two optically active phosphorus atoms, chiral transition metal catalysts which comprise these compounds as ligands, a process for preparing the P-chiral compounds and processes for asymmetric synthesis using the chiral transition metal catalysts. The present invention specifically relates to a process for preparing an optically active carbonyl compound by asymmetric hydrogenation of a prochiral α,β-unsaturated carbonyl compound with hydrogen in the presence of an optically active transition metal catalyst according to the invention. Yet more specifically, the present invention relates to a process for the asymmetric hydrogenation of citral, and also a process for preparing optically active menthol.

PRIOR ART

Asymmetric synthesis is the name for reactions in which a chiral group is produced from a prochiral one in such a way that the stereoisomeric products (enantiomers or diastereomers) are formed in unequal amounts. Asymmetric synthesis has gained immense importance not only in the area of the pharmaceutical industry, but also for producing aroma chemicals (fragrances and flavors), since often only a specific optically active isomer has the desired odor (olfactory) or taste (gustatory) properties. There is therefore a continuing need for new asymmetric synthesis processes and specifically for catalysts with good application properties, such as a large asymmetric induction for certain stereocenters, the possibility of maintaining mild reaction conditions high space/time yields, etc.

An important class of asymmetric reactions is the asymmetric hydrogenation, i.e. the addition of hydrogen onto carbon-carbon and onto carbon-heteroatom multiple bonds. Further important asymmetric reactions are e.g. 1-hydro-2-carbo additions, i.e. an addition of hydrogen and a carbon-atom-containing group. Important representatives of this reaction are e.g. hydroformylation, hydrocyanation and carbonylation.

Many optically active aldehydes and ketones are valuable intermediates in the synthesis of higher-value-added chiral value substances and active ingredients and are themselves valuable end products. Thus, for example, citronellal is an important aroma substance which is used, inter alia, as ingredient of perfumes. Furthermore, it serves as starting material for the total synthesis of menthol, another important aroma substance. The selective hydrogenation of the C=C double bond adjacent to the carbonyl group in the stereoisomeric monoterpenes neral or geranial or the mixture of the two, called citral, leads to citronellal. For many applications in the scent and fragrance industry the racemic product is already suitable. For the regioselective synthesis of citronellal, the hydrogenation must proceed only at the double bond in the α,β position relative to the carbonyl group (see scheme). The simultaneous reduction of the aldehyde group and thus the formation of citronellol or only the hydrogenation of the aldehyde group and therefore the formation of nerol/geraniol must not take place. The second olefinic double bond must also remain intact.

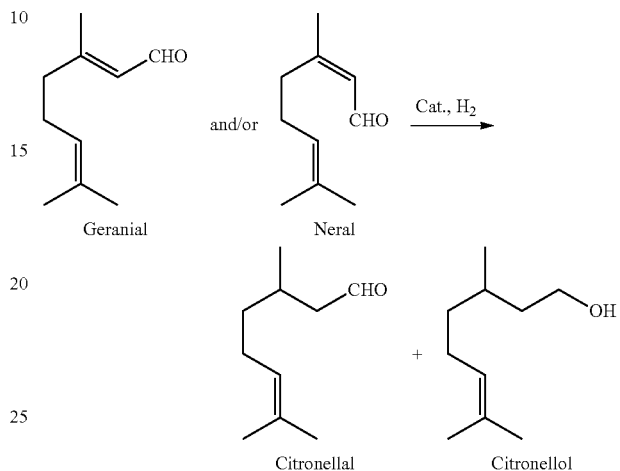

WO 2012/150053 describes a process for the hydrogenation of conjugated dienals to give nonconjugated enals with rhodium complexes in a carbon monoxide-free atmosphere. The bidentate diphosphine ligands used have a "natural bite angle" of 93° to 130°. The natural bite angle of diphosphines is defined as the selective chelate formation angle, i.e. (P-metal-P)-bonding angle, as is pregiven by the ligand scaffold. Accordingly, the diphosphine ligands used have a rigid molecular backbone and are selected, for example, from among compounds of the formulae (A) and (B)

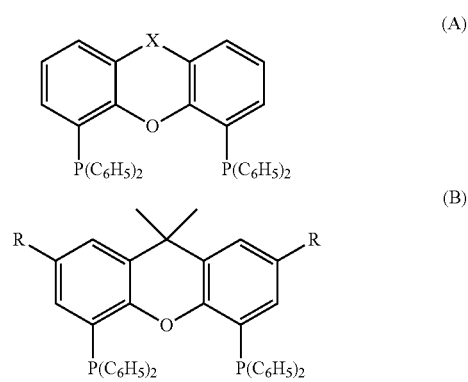

where $X=C(CH_3)_2$, NH, $Si(CH_3)_2$ and $R=CH_3$, $C_2H_5$, t.-$C_4H_9$.

The bidentate diphosphine ligands used according to WO 2012/150053 are not chiral. WO 2014/167014 A1 describes a process for the preparation of citronellal by homogeneous Rh-catalyzed hydrogenation of neral and geranial, either individually or as a mixture, where the hydrogenation is carried out under a CO-free hydrogen atmosphere and using a CO-free catalyst system at temperatures of 0 to 60° C., a hydrogen pressure of 1 to 100 bar and using diphosphines with at least one ether group as controlling organic ligands for the Rh catalyst system. The ligands used are in turn not chiral.

U.S. Pat. No. 4,237,072 describes a process for the preparation of optically active citronellal by hydrogenation of geranial or neral in the presence of a catalyst complex made of rhodium and a chiral phosphine dissolved in the reaction system.

T.-P. Dang et al. describe in J. Mol. Cat., 1982, volume 16, pages 51-59, a process for the homogeneously catalytic hydrogenation of α,β-unsaturated aldehydes, and also the use of this process for preparing optically active citronellal. The catalysts used here were complex compounds of a rhodium carbonyl compound and a chiral diphosphine.

Chapuis at al. mention in Helv. Chim. Acta, 2001, volume 84, pages 230-242, footnote 4, the asymmetric hydrogenation of geranial or neral to give optically active citronellal in the presence of a catalyst of $Rh_4(CO)_{12}$ and (R,R)-chiraphos (2R,3R)-2,3-bis(diphenylphosphino)butane.

One problem in the case of the procedure by means of soluble catalysts of catalyzed (homogeneously catalytic) reactions consists in the often inadequate stability of the catalyst complexes used and/or the catalytically active metal or transition metal complex compound that is formed therefrom.

JP-A 52078812 describes a process for the hydrogenation of α,β-unsaturated aldehydes such as crotonaldehyde, cinnamaldehyde or α-methylcinnamaldehyde over homogeneous Rh catalysts under hydroformylation conditions in the presence of a triarylphosphine, a tertiary amine in stoichiometric amounts and carbon monoxide.

WO 2006/040096 describes a process for preparing optically active carbonyl compounds by asymmetric hydrogenation of α,β-unsaturated carbonyl compounds with hydrogen in the presence of an optically active transition metal catalyst that is soluble in the reaction mixture and has at least one carbon monoxide ligand, which is characterized in that the catalyst is pretreated with a gas mixture containing carbon monoxide and hydrogen and/or the asymmetric hydrogenation is carried out in the presence of carbon monoxide additionally added to the reaction mixture.

WO 2008/132057 likewise describes a process for preparing optically active carbonyl compounds by asymmetric hydrogenation of α,β-unsaturated carbonyl compounds which is based on the process disclosed in WO 2006/040096. To better control the carbon monoxide concentration in the reaction mixture during the hydrogenation, this process additionally includes the provisos that the pretreatment of the catalyst precursor with a gas mixture comprising 20 to 90% by volume carbon monoxide, 10 to 80% by volume hydrogen and 0 to 5% by volume further gases, where the specified volume fractions add up to 100% by volume, is carried out at a pressure from 5 to 100 bar, excess carbon monoxide is separated off from the thus obtained catalyst prior to use in the asymmetric hydrogenation and the asymmetric hydrogenation is carried out in the presence of hydrogen with a carbon monoxide content of 100 to 1200 ppm.

Bayardon et al. in Phosphorus, Sulfur and Silicon, 190: 700-705, 2015, and in WO 2013/007724 describe chiral phosphines and diphosphines and use thereof as chiral ligands in asymmetric synthesis. Specifically, compound (C) is described.

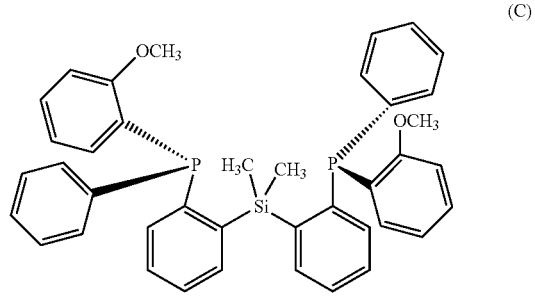

(C)

It was an object of the present invention to provide novel chiral compounds and chiral transition metal catalysts which comprise these compounds as ligands, where the catalysts should advantageously be suitable for use for asymmetric synthesis. They should specifically be suitable for preparing optically active carbonyl compounds by asymmetric hydrogenation and in particular for the asymmetric hydrogenation of citral to citronellal. In this connection, a use of the chiral transition metal catalysts according to the invention under mild reaction conditions should be possible. In particular, it should be possible to dispense with the presence of carbon monoxide during the hydrogenation.

New P-chiral phosphine ligands have now been found which are advantageously suitable for the asymmetric synthesis and by virtue of which the set object is achieved.

DESCRIPTION OF THE INVENTION

The present invention relates to chiral compounds of the general formula (I)

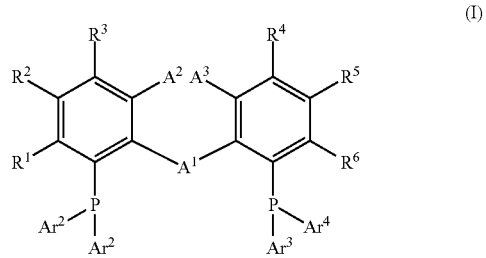

(I)

in which $A^1$ is O, S, $CR^aR^b$, $NR^a$, $SiR^aR^b$, S(=O), S(=O)$_2$, $BR^a$, $PR^a$ or P(=O)$R^a$, where $R^a$ and $R^b$, independently of one another, are hydrogen, $C_1$-$C_{30}$-alkyl, $C_3$-$C_{12}$-cycloalkyl, heterocycloalkyl with 3 to 12 ring atoms, $C_6$-$C_{14}$-aryl or hetaryl with 5 to 14 ring atoms, where the cycloalkyl, heterocycloalkyl, aryl and hetaryl groups are unsubstituted or carry one, two or three substituents selected from $C_1$-$C_{10}$-alkyl and $C_1$-$C_{10}$-alkoxy, $A^2$ and $A^3$, independently of one another, are hydrogen, $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-haloalkyl, hydroxy, mercapto, cyano, nitro, polyalkylene oxide, polyalkyleneimine, halogen, carboxyl, carboxylate, formyl, acyl, sulfo, sulfonate or $NE^1E^2$, in which $E^1$ and $E^2$ are in each case identical or different radicals selected from hydrogen, $C_1$-$C_{30}$-alkyl, $C_3$-$C_{12}$-cycloalkyl and $C_6$-$C_{14}$-aryl, or $A^2$ and $A^3$ together are a chemical bond between the two benzene rings, or $A^2$ and $A^3$ together are O, S, $CR^cR^d$, $NR^c$, $SiR^cR^d$, S(=O), S(=O)$_2$, $BR^c$, $PR^c$ or P(=O)$R^c$, where $R^c$ and $R^d$, independently of one another, are hydrogen, $C_1$-$C_{30}$-alkyl, $C_3$-$C_{12}$-cycloalkyl, heterocycloalkyl with 3 to 12 ring atoms, $C_6$-$C_{14}$-aryl or hetaryl with 5 to 14 ring atoms, where cycloalkyl, heterocycloalkyl, aryl and hetaryl groups are unsubstituted or carry one, two or three substituents selected from $C_1$-$C_{10}$-alkyl or $C_1$-$C_{10}$-alkoxy, or $A^1$, $A^2$ and $A^3$ together are a bridging group

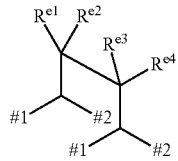

where each of the variables #1 and #2 is a binding site, where the binding sites #1 are bonded to two adjacent carbon atoms of the one benzene ring and the binding sites #2 are bonded to two adjacent carbon atoms of the other benzene ring, $R^{e1}$, $R^{e2}$, $R^{e3}$ and $R^{e4}$, independently of one another, are hydrogen, $C_1$-$C_{20}$-alkyl, $C_3$-$C_{12}$-cycloalkyl, $C_6$-$C_{14}$-aryl, halogen, trifluoromethyl, carboxyl or carboxylate, where $R^{e1}$, also together with $R^{e3}$, can be the binding fraction of a double bond between the two carbon atoms to which $R^{e1}$ and $R^{e3}$ are bonded, or $R^{e1}$, $R^{e2}$, $R^{e3}$ and $R^{e4}$ together with the carbon atoms of the bridging group to which they are bonded can also be a benzene ring or a condensed aromatic ring system with 1, 2 or 3 benzene rings, where the benzene rings are unsubstituted or where each of the benzene rings can have 1 or 2 substituents which are selected, independently of one another, from $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-haloalkyl, hydroxy, mercapto, cyano, nitro, polyalkylene oxide, polyalkyleneimine, halogen, carboxyl, carboxylate, formyl, acyl, sulfo, sulfonate or $NE^3E^4$, in which $E^3$ and $E^4$ are in each case identical or different radicals selected from hydrogen, $C_1$-$C_{30}$-alkyl, $C_3$-$C_{12}$-cycloalkyl and $C_6$-$C_{14}$-aryl, $Ar^1$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_3$-$C_{12}$-cycloalkyl and $C_6$-$C_{14}$-aryl, $Ar^2$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_3$-$C_{12}$-cycloalkyl and $C_6$-$C_{14}$-aryl, $Ar^3$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_1$-$C_{12}$-cycloalkyl and $C_6$-$C_{14}$-aryl, $Ar^4$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_3$-$C_{12}$-cycloalkyl and $C_1$-$C_{14}$-aryl, with the proviso that $Ar^1$ and $Ar^2$ do not have the same meaning, and that $Ar^3$ and $Ar^4$ do not have the same meaning, $R^1$, $R^2$, $R^3$, $R^4$, R and $R^6$, independently of one another, are hydrogen, $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-haloalkyl, hydroxy, mercapto, cyano, nitro, polyalkylene oxide, polyalkyleneimine, halogen, carboxyl, carboxylate, formyl, acyl, sulfo, sulfonate or $NE^5E^6$, in which $E^5$ and $E^6$ are in each case identical or different radicals selected from hydrogen, $C_1$-$C_{20}$-alkyl, $C_3$-$C_{12}$-cycloalkyl and $C_6$-$C_{14}$-aryl, where two adjacent radicals $R^1$ to $R^6$, together with the carbon atoms of the benzene ring to which they are bonded, can also be a condensed ring system with 1, 2 or 3 further benzene rings, where the benzene rings of the condensed ring system are unsubstituted or each of the benzene rings can have 1 or 2 substituents which are selected, independently of one another, from $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-haloalkyl, hydroxy, mercapto, cyano, nitro, polyalkylene oxide, polyalkyleneimine, halogen, carboxyl, carboxylate, formyl, acyl, sulfo, sulfonate or $NE^7E^8$, in which $E^7$ and $E^8$ are in each case identical or different radicals selected from hydrogen, $C_1$-$C_{20}$-alkyl, $C_3$-$C_{12}$-Cycloalkyl and $C_6$-$C_{14}$-aryl.

The compounds of the formula (I) are novel, except for a compound of the formula (I) where $A^1$ is $Si(CH_3)_2$, $Ar^1$ and $Ar^3$ are in each case phenyl, $Ar^2$ and $Ar^3$ are in each case 2-methoxyphenyl and $R^1$, $R^2$, $R^3$, $R^4$, $R^5$, $R^6$, $A^2$ and $A^3$ are in each case hydrogen.

The invention further provides a chiral catalyst comprising or consisting of at least one transition metal complex which has at least one chiral compound of the general formula (I), as defined above and below, as ligand.

The invention further provides a process for preparing a chiral compound of the general formula (I), as defined above and below, in which
a) a compound of the general formula (I.a)

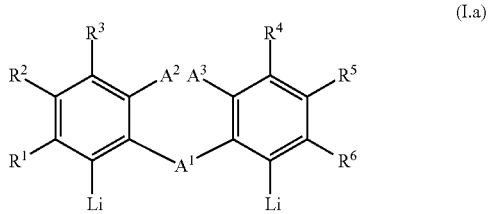

is provided, in which $A^1$, $A^2$, $A^3$, $R^1$, $R^2$, $R^3$, $R^4$, $R^5$ and $R^6$ have the meanings given above,
b) a compound of the general formula (I.b1) is provided and, if $Ar^1$ and $Ar^3$ and $Ar^2$ and $Ar^4$ do not have the same meaning, a compound of the general formula (I.b2) is provided,

in which
$Ar^1$, $Ar^2$, $Ar^3$ and $Ar^4$ have the meanings given above, and $X^1$ and $X^2$, independently of one another, are $C_1$-$C_4$-alkoxy,
and
c) the compound of the general formula (I.a) is reacted with the compound of the general formula (I.b1) and, if present, with the compound of the general formula (I.b2), to give a compound of the general formula (I).

The invention further provides a process for preparing chiral compounds by reaction of a prochiral compound which comprises at least one ethylenically unsaturated double bond in the presence of a chiral catalyst comprising at least one transition metal complex with at least one compound of the general formula (I), as defined above and below, as ligands.

In particular, it is a hydrogenation, allylic alkylation, hydroformylation, hydrocyanation, carbonylation, hydroacylation, hydroamidation, hydroesterification, hydrosilylation, hydroboration, aminolysis, alcoholyis, isomerization, methathesis, cyclopropanation or aldol condensation. A preferred carbonylation reaction is the conversion of olefins with carbon monoxide and water to give carboxylic acids (hydrocarboxylation) or carbon monoxide and alcohols to give carboxylic acid esters (alkoxycarbonylation).

The invention further provides a process for preparing an optically active carbonyl compound by asymmetric hydrogenation of a prochiral α,β-unsaturated carbonyl compound with hydrogen in the presence of at least one optically active transition metal catalyst which has rhodium as catalytically active transition metal and a chiral compound of the general formula (I), as defined above and below, as ligands.

Specifically, the asymmetric hydrogenation is carried out in the presence of an optically active transition metal catalyst that is soluble in the reaction mixture and which has rhodium as catalytically active transition metal and a chiral compound of the general formula (I), as defined above and below, as ligands.

The invention further provides a process for preparing optically active citronellal of the formula (VI)

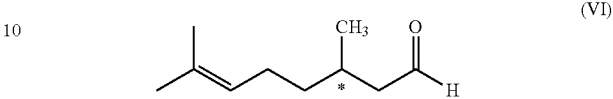

in which * designates the asymmetry center,
by asymmetric hydrogenation of geranial of the formula (IIa-1) or of neral of the formula (IIb-1)

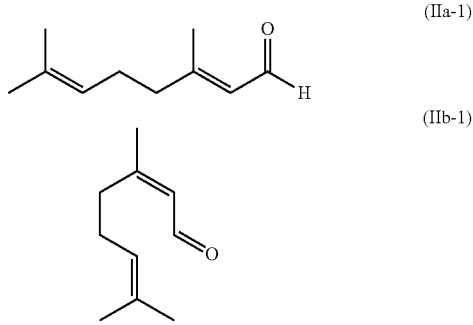

or a mixture comprising neral and geranial.

The invention further provides a process for preparing optically active menthol in which optically active citronellal of the formula (VI), obtainable by a process as defined above and below, is subjected to a cyclization to give optically active isopulegol, and the optically active isopulegol is hydrogenated to give optically active menthol.

In the definitions of the substituents specified in the formulae above, collective terms are used which are generally representative of the respective substituents. The denotation $C_n$-$C_m$ indicates in each case the possible number of carbon atoms in the respective substituents or substituent part.

Halogen: is fluorine, chlorine, bromine or iodine.

Acyl: is in the context of the present invention alkanoyl or aroyl groups having in general 2 to 11, preferably 2 to 8 carbon atoms, for example the acetyl, propanoyl, butanoyl, pentanoyl, hexanoyl, heptanoyl, 2-ethylhexanoyl, 2-propylheptanol, benzoyl or naphthoyl group.

Formyl: is H—C(=O)—.
Carboxy: is —C(=O)OH.
Sulfo: is —S(=O)$_2$—OH.

Carboxylate and sulfonate in the context of this invention are preferably a derivative of a carboxylic acid function or of a sulfonic acid function, in particular a metal carboxylate or sulfonate, a carboxylic acid or sulfonic acid ester function or a carboxamide or sulfonamide function. These include e.g. the esters with $C_1$-$C_4$-alkanols, such as methanol, ethanol, n-propanol, isopropanol, n-butanol, sec-butanol and tert-butanol.

These also include the primary amides and N-alkyl and N,N-dialkyl derivatives thereof.

Alkyl: is a saturated, straight-chain or branched hydrocarbon radical having 1 to 4 ($C_1$-$C_4$-alkyl), 1 to 6 ($C_1$-$C_6$- alkyl), 1 to 10 ($C_1$-$C_{10}$-alkyl), 1 to 20 ($C_1$-$C_{20}$-alkyl) or 1 to 30 ($C_1$-$C_{30}$-alkyl) carbon atoms, e.g. $C_1$-$C_4$-alkyl such as methyl, ethyl, propyl, 1-methyl-ethyl, butyl, 1-methylpropyl, 2-methylpropyl; $C_1$-$C_6$-alkyl: $C_1$-$C_4$-alkyl as specified above, and 1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl; $C_1$-$C_{10}$-alkyl: $C_1$-$C_6$-alkyl as specified above, and n-heptyl, n-octyl, n-nonyl, n-decyl; $C_1$-$C_{20}$-alkyl: $C_1$-$C_{10}$-alkyl as specified above, and n-undecyl, n-dodecyl, n-tridecyl, n-tetradecyl, n-pentadecyl, n-hexadecyl, n-heptadecyl, n-octa-decyl and n-nonadecyl.

Halo(gen) alkyl: is a straight-chain or branched alkyl group having 1 to 4, 1 to 6, 1 to 8, 1 to 10 or 1 to 20 carbon atoms (as specified above), where, in this group, the hydrogen atoms can be partially or completely replaced by halogen atoms as specified above, e.g. $C_1$-$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Hydroxyalkyl: is a mono- or poly-, in particular monohydroxylated, straight-chain or branched alkyl group having 1 to 4, 1 to 6, 1 to 8, 1 to 10 or 1 to 20 carbon atoms (as specified above) such as e.g. the monohydroxylated analogs of the above straight-chain or branched alkyl radicals, such as e.g. a linear hydroxyalkyl group such as hydroxymethyl, 2-hydroxyethyl, 3-hydroxypropyl, 4-hydroxybutyl, or one of those with a non-terminal hydroxyl group, such as 1-hydroxyethyl, 1- or 2-hydroxypropyl, 1- or 2-hydroxybutyl or 1-, 2- or 3-hydroxybutyl.

Aminoalkyl: is in particular a mono- or poly-, in particular monoaminated analog of an above hydroxyalkyl radical, where the OH group is replaced by an amino group ($NH_2$).

Alkylene: is a straight-chain or mono- or polybranched alkanediyl group having 1 to 25 carbon atoms, i.e. hydrocarbon bridge group having 1 to 25 carbon atoms, such as e.g. —$CH_2$—, —$(CH_2)_2$—, —$(CH_2)_3$—, —$(CH_2)_4$—, —$(CH_2)_2$—$CH(CH_3)$—, —$CH_2$—$CH(CH_3)$—$CH_2$—, $(CH_2)_4$—, —$(CH_2)_5$—, —$(CH_2)_6$—, —$(CH_2)_7$—, —CH$(CH_3)$—$CH_2$—$CH_2$—$CH(CH_3)$— or —$CH(CH_3)$—$CH_2$—$CH_2$—$CH_2$—$CH(CH_3)$—.

Polyalkylene: is a radical which is composed essentially of $C_{2-6}$—, in particular $C_{2-4}$-monomer building blocks, such as ethylene, propylene, n- or isobutylene or mixtures, and has a degree of polymerization of 2 to 100, or 3 to 50 or 4 to 25 or 5 to 10.

Oxyalkylene: is a mono- or polybranched alkylene radical having 2 to 10 carbon atoms, as defined above, where the carbon chain is interrupted one or more times, in particular once, by an oxygen atom, such as e.g. —$CH_2$—O—$CH_2$—, —$(CH_2)_2$—O—$(CH_2)_2$—, —$(CH_2)_3$—$(CH_2)_3$—, or —$CH_2$—O—$(CH_2)_2$—, —$(CH_2)_2$—O—$(CH_2)_3$—, —$CH_2$—O—$(CH_2)_3$.

Polyalkylene oxide: is a radical derived from identical or different $C_{2-4}$-oxyalkylene monomer building blocks, as defined above, with a degree of polymerization of 2 to 100, or 3 to 50 or 4 to 25 or 5 to 10.

Polyalkyleneimine: is a structure-analogous radical to the above polyalkylene oxide radical, with the oxygen atom being replaced by an imine group.

Alkoxy is a saturated, straight-chain or branched hydrocarbon radical having 1 to 4, 1 to 6, 1 to 10, 1 to 20 or 1 to 30 carbon atoms, as defined above, which is bonded via oxygen, e.g. $C_1$-$C_4$-alkoxy such as methoxy, ethoxy, n-propoxy, 1-methylethoxy, butoxy, 1-methylpropoxy, 2-methylpropoxy or 1,1-dimethylethoxy; $C_1$-$C_6$-alkoxy: $C_1$-$C_4$-alkoxy, as specified above, and e.g. pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy.

Haloalkoxy: is an alkoxy radical having 1 to 4, 1 to 6, 1 to 10, 1 to 20 or 1 to 30 C atoms as mentioned above which is partially or completely substituted by fluorine, chlorine, bromine and/or iodine, e.g. $C_1$-$C_{10}$-haloalkoxy such as $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, $OC_2F_5$, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy.

Cycloalkyl: is a monocyclic, bicyclic or tricyclic, saturated hydrocarbon groups having 3 to 12, preferably 3 to 6 or 3 to 8 carbon ring members, e.g. a monocyclic hydrocarbon groups having 3 to 8 carbon ring members such as cyclopropyl, cyclobutyl, cyclopentyl, cyclohexyl, cycloheptyl or cyclooctyl; a bicyclic hydrocarbon group having 5 to 10 carbon ring members such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl and bicyclo[4.4.0]decyl; a tricyclic hydrocarbon group with 6 to 10 carbon ring members such as adamantyl.

Cycloalkoxy (=cycloalkyloxy): is a monocyclic, bicyclic or tricyclic, saturated hydrocarbon group having 3 to 12, preferably up to 6, up to 8 carbon ring members, as defined above, which is bonded via an oxygen atom.

Aryl: is a mono- or polynuclear aromatic hydrocarbon radical having usually 6 to 14, preferably 6 to 10 carbon atoms such as e.g. phenyl, naphthyl, indenyl, fluoroenyl, anthracenyl or phenanthrenyl.

$C_6$-$C_{14}$-Aryl-$C_1$-$C_{10}$-alkylene: is a mono- or polynuclear aromatic hydrocarbon radical having usually 6 to 14, preferably 6 to 10, carbon atoms, as defined above, which is bonded via a straight-chain or a mono- or polybranched alkanediyl group (=alkylene group) having 1 to 10 carbon atoms, e.g. benzyl, 1-phenylethyl, 2-phenylethyl, 1-, 2-, 3- or 4-phenylbutyl or 1-, 2-, 3-, 4-, 5- or 6-phenylhexyl.

$C_1$-$C_{10}$-Alkyl-$C_6$-$C_{14}$-aryl: is a mono- or polynuclear aromatic hydrocarbon radical having usually 6 to 14, preferably 6 to 10 carbon atoms, as defined above, in which one or more hydrogen atoms, preferably one, two or three hydrogen atoms, can be replaced by straight-chain or branched alkyl having 1 to 10 carbon atoms, as defined above, e.g. tolyl, mesityl, ethylphenyl, 1-methylnaphthyl, 2-methylnaphthyl.

Aryloxy: is a mono- or polynuclear aromatic hydrocarbon radical having usually 6 to 14, preferably 6 to 10 carbon atoms, as defined above, which is bonded via an oxygen atom.

Heterocycloalkyl (heterocyclyl) with 3 to 12 ring atoms: is a saturated, partially (e.g. mono-) unsaturated heterocyclic radical having 3, 4, 5, 6, 7, 8, 9, 10, 11 or 12 ring atoms, of which 1, 2 or 3 are selected from N, O, S, S(O) and S(O)$_2$ and the other ring atoms are carbon; such as e.g. 3- to 8-membered saturated heterocyclyl such as oxiranyl, oxetanyl, aziranyl, piperidinyl, piperazinyl, morpholinyl, thimorpholinyl, pyrrolidinyl, oxazolidinyl, tetrahydrofuryl, dioxolanyl, dioxanyl, hexahydroazepinyl, hexyhydrooxepinyl, and hexahydrothiepinyl; partially unsaturated 3-, 4-, 5-, 6-, 7- or 8-membered heterocyclyl such as di- and tetrahydropyridinyl, pyrrolinyl, oxazolinyl, dihydrofuryl, tetrahydroazepinyl, tetrahydrooxepinyl, and tetrahydrothiepinyl.

Heterocycloalkoxy (=hetarocycloalkoxy) with 3 to 12 ring atoms: is a saturated, partially (e.g. mono-) unsaturated heterocyclic radical having 3, 4, 5, 6, 7, 8, 9, 10, 11 or 12 ring atoms, of which 1, 2 or 3 are selected from N, O, S, S(O) and S(O)$_2$ and the other ring atoms are carbon, as defined above, which is bonded via oxygen.

Hetaryl (=heteroaryl): is an aromatic, mono- or polynuclear heterocycle which, besides carbon atoms, comprises one to four heteroatoms from the group O, N or S as ring members; such as e.g.

- 5-membered heteroaryl, which, besides carbon atom(s) can comprise one to four nitrogen atoms or one to three nitrogen atoms and one sulfur or oxygen atom or one sulfur or oxygen atom as ring member, e.g. furyl, thienyl, pyrrolyl, isoxazolyl, isothiazolyl, pyrazolyl, oxazolyl, thiazolyl, imidazolyl, oxadiazolyl, thiadiazolyl, triazolyl;
- benzo-fused 5-membered heteroaryl: 5-ring heteroaryl groups as defined above which may be condensed with one or two benzene rings in such a way that two adjacent carbon ring members or one nitrogen and one adjacent carbon ring member are bridged by a buta-1,3-diene-1,4-diyl group, e.g. indolyl, isoindolyl, benzimidazolyl, benzofuryl, benzothienyl, benzoxazolyl, benzisoxazolyl, benzo-thiazolyl, dibenzofuranyl, dibenzothienyl or carbazolyl;
- 6-membered heteroaryl: 6-ring heteroaryl groups which, besides carbon atoms, can comprise one to three or one to four nitrogen atoms as ring members, e.g. pyridinyl, pyridazinyl, pyrimidinyl, pyrazinyl, 1,3,5-triazin-2-yl and 1,2,4-triazin-3-yl;
- benzo-fused 6-membered heteroaryl: 6-ring heteroaryl groups as defined above which may be condensed with one or two benzene rings in such a way that two adjacent carbon ring members are bridged by a buta-1,3-diene-1,4-diyl group, e.g. quinolinyl, isoquinolinyl, quinazolinyl, quinoxalinyl, acridinyl or phenazinyl.

"Chiral compounds" are compounds without axis of symmetry. In the context of the present invention, they are in particular compounds with at least one chirality center (i.e. at least one asymmetric atom, in particular at least one asymmetric P atom or C atom) and without axis of symmetry.

In the context of the present invention, the term "chiral catalyst" comprises catalysts which have at least one chiral ligand.

"Achiral compounds" are compounds which are not chiral.

A "prochiral compound" is understood as meaning a compound with at least one prochiral center.

"Asymmetric synthesis" refers to a reaction in which a compound with at least one chirality center is produced from a compound with at least one prochiral center, where the stereoisomeric products are formed in unequal amounts.

"Stereoisomers" are compounds of identical constitution but different atomic arrangement in the three-dimensional space.

"Enantiomers" are stereoisomers which behave like image to mirror image to one another. The "enantiomeric excess" (ee) achieved during asymmetric synthesis is given here by the following formula: ee [%]=(R−S)/(R+S)×100. R and S are the descriptors of the CIP system for the two enantiomers and describe the absolute configuration on the asymmetric atom. The enantiomerically pure compound (ee=100%) is also referred to as "homochiral compound".

The process according to the invention leads to products which are enriched with regard to a specific stereoisomer. The attained "enantiomer excess" (ee) is generally at least 20%, preferably at least 50%, in particular at least 80%.

"Diastereomers" are stereoisomers which are not enantiomeric to one another.

In a preferred embodiment of the compounds of the general formula (I), $A^1$ is O and $A^2$ and $A^3$ are a chemical bond between the benzene rings.

$A^1$ is preferably O, S, $CR^aR^b$, $NR^a$, $S(=O)$, $S(=O)_2$, $BR^a$, $PR^a$ or $P(=O)R^a$, where $R^a$ and $R^b$ have the meanings specified above.

In a further preferred embodiment of the compounds of the general formula (I), $A^1$ is O and $A^2$ and $A^3$ together are $CR^cR^d$, where $R^c$ and $R^d$, independently of one another, are hydrogen or $C_1$-$C_4$-alkyl.

In a preferred embodiment of the compounds of the general formula (I), $A^1$ is O and $A^2$ and $A^3$ are both hydrogen.

Preferably, $R^1$, $R^2$, $R^3$, $R^4$, $R^5$ and $R^6$, independently of one another, are selected from hydrogen, $C_1$-$C_{20}$-alkyl and $C_1$-$C_{20}$-alkoxy.

Particularly preferably, two of the radicals $R^1$, $R^2$, $R^3$, $R^4$, $R^5$ and $R^6$ are $C_1$-$C_{20}$-alkyl or are $C_1$-$C_{20}$-alkoxy and the others are hydrogen.

A specific embodiment is compounds of the formula I in which $A^1$ is O, $R^1$, $R^2$, $R^3$, $R^4$, $R^5$ and $R^6$ are each in case hydrogen and $A^2$ and $A^3$ together are $C(CH_3)_2$. These compounds are referred to hereinbelow also as compounds I-A.

A further specific embodiment is compounds of the formula I in which $A^1$ is O, $R^1$, $R^3$, $R^4$ and $R^6$ are in each case hydrogen, $R^2$ and $R^5$ are in each case t-butyl, and $A^2$ and $A^3$ together are $C(CH_3)_2$. These compounds are also referred to hereinbelow as compounds I-B.

A further specific embodiment is compounds of the general formula (I) in which $A^1$ is O and $A^2$, $A^3$, $R^1$, $R^2$, $R^3$, $R^4$, $R^5$ and $R^6$ are in each case hydrogen. These compounds are also referred to hereinbelow as compounds I-C.

In a specific variant, $A^1$, $A^2$ and $A^3$ together are a bridging group

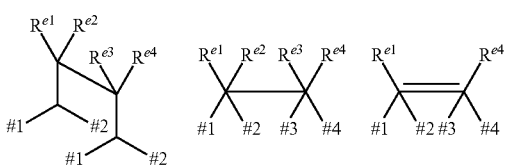

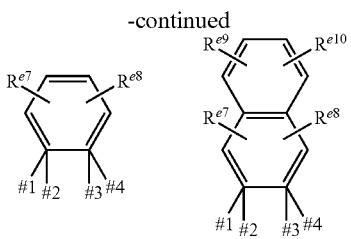

which is selected from the groups
in which $R^{e1}$, $R^{e2}$, $R^{e3}$ and $R^{e4}$, independently of one another, are hydrogen, alkyl, cycloalkyl, aryl, halogen, trifluoromethyl, carboxyl, carboxylate or cyano or are joined together to give a $C_3$-$C_4$-alkylene group, and $R^{e7}$, $R^{e8}$, $R^{e9}$ and $R^{e10}$, independently of one another, are hydrogen, alkyl, cycloalkyl, aryl, halogen, trifluoromethyl, COOH, carboxylate, cyano, alkoxy, $SO_3H$, sulfonate, $NE^9E^{10}$, alkylene-$NE^9E^{10}E^{11+}X^-$, aryl or nitro. Preferably, the groups $R^{e1}$, $R^{e2}$, $R^{e3}$ and $R^{e4}$ are hydrogen, $C_1$-$C_{10}$-alkyl or carboxylate and the groups $R^{e7}$, $R^{e8}$, $R^{e9}$ and $R^{e10}$ are hydrogen, $C_1$-$C_{10}$-alkyl, halogen, in particular fluorine, chlorine or bromine, trifluoromethyl, $C_1$-$C_4$-alkoxy, carboxylate, sulfonate or aryl. Particularly preferably, $R^{e7}$, $R^{e8}$, $R^{e9}$, and $R^{e10}$ are hydrogen. Particularly preferred bridging groups are the ethylene group and the 1, 2-phenylene group. A particularly preferred bridging group is the ethylene group —$CH_2$—$CH_2$—.

Preferably, $Ar^1$, $Ar^2$, $Ar^3$ and $Ar^4$ are selected independently of one another from phenyl, 1-naphthyl, 2-naphthyl, 9-phenanthryl, 2-tolyl, 3-tolyl, 4-tolyl, 2-ethylphenyl, 3-ethylphenyl, 2-isopropylphenyl, 3-isopropylphenyl, 4-(2-methylbutyl)phenyl, 2-anisyl, 3-anisyl, 4-anisyl, 2-ethoxyphenyl; 4-ethoxyphenyl, 3-ethoxyphenyl, 2-isopropoxy-phenyl, 3-isopropoxyphenyl, 3,5-dimethoxyphenyl and dibenzo[b,d]-furan-4-yl.

In a preferred embodiment of the compounds of the general formula (I), $Ar^1$ and $Ar^3$ have the same meaning and $Ar^2$ and $Ar^4$ have the same meaning.

Preferably, $Ar^1$ and $Ar^3$ are both in each case phenyl.

Further preferably, $Ar^2$ and $Ar^4$ are both in each case 1-naphthyl, 2-naphthyl, 9-phenanthryl, 2-tolyl, 3-tolyl, 4-tolyl, 2-ethylphenyl, 3-ethylphenyl, 2-isopropylphenyl, 3-isopropylphenyl, 4-(2-methylbutyl)phenyl, 2-anisyl, 3-anisyl, 4-anisyl, 2-ethoxyphenyl, 4-ethoxyphenyl, 3-ethoxyphenyl, 2-isopropoxyphenyl, 3-isopropoxyphenyl, 3,5-dimethoxyphenyl or dibenzo[b,d]-furan-4-yl.

Specifically, the compounds of the general formula (I) are selected from
(1S,1'S)-(+)-(9,9-dimethyl-9H-xanthen-4,5-diyl)bis((2-methoxyphenyl)(phenyl)-phosphine)
(1S,1'S)(+)-(9,9-dimethyl-9H-xanthene-4,5-diyl)bis((2-methylphenyl)(phenyl)-phosphine)
(1S,1'S)-(–)-(9,9-dimethyl-9H-xanthene-4,5-diyl)bis((4-methoxyphenyl)(phenyl)-phosphine)
(1S,1'S)-(–)-9,9-dimethyl-9H-xanthene-4,5-dl)bis((4-methylphenyl)(phenyl)phosphine)
(1S,1'S)-(–)-(9,9-dimethyl-9H-xanthene-4,5-diyl)bis((1-naphthyl)phenyl)phosphine)
(1S,1'S)-(–)-(9,9-dimethyl-9H-xanthene-4,5-diyl)bis((2-naphthyl)(phenyl)phosphine)
(1S,1'S)-(–)-(9,9-dimethyl-9H-xanthene-4,5-diyl)bis((9-phenanthryl)(phenyl)phosphine)
(1S,1'S)-(–)-(9,9-dimethyl-9H-xanthene-4,5-diyl)bis((3,5-dimethoxyphenyl)(phenyl)-phosphine)
(1S,1'S)-(+)-(9,9-dimethyl-9H-xanthene-4,5-diyl)bis(2-isopropoxyphenyl)(phenyl)(phosphine)
(1S,1'S)-(–)-(9,9-dimethyl-9H-xanthene-4,5-diyl)bis((2-ethoxyphenyl)(phenyl)phosphine)
(1S,1'S)-(–)-(9,9-dimethyl-9H-xanthene-4,5-diyl)bis((3-methoxyphenyl)(phenyl)(phosphine)
(1S,1'S)-(–)-(9,9-dimethyl-9H-xanthene-4,5-diyl)bis((3-isopropoxyphenyl)(phenyl)phosphine)
(1S,1'S)-(–)-(9,9-dimethyl-9H-xanthene-4,5-diyl)bis((dibenzo[b,d]-furan-4-yl)(phenyl)-phosphine)
(1S,1'S)-(+)-(9,9-dimethyl-9H-xanthene-4,5-diyl)bis((2-ethylphenyl)(phenyl)phosphine)
(1S,1'S)-(+)-(9,9-dimethyl-9H-xanthene-4,5-diyl)bis((3-methylphenyl)(phenyl)-phosphine)
(1S,1'S)-(–)-(9,9-dimethyl-9H-xanthene-4,5-diyl)bis(3-ethoxyphenyl)(phenyl)(phosphine)
(1S,1'S)-(–)-(9,9-dimethyl-9H-xanthene-4,5-diyl)bis((4-(rac-2-methylbutyl)(phenyl) phenylphosphine)
(1S,1'S)-(–)-9,9-dimethyl-9H-xanthene-4,5-diyl)bis((4-ethoxyphenyl)(phenyl)phosphine)
(1S,1'S)-(+)-(2,7-di-tert-butyl-9,9-dimethyl-9H-xanthene-4,5-diyl)bis((2-methoxyphenyl) (phenylphosphine)
(1S,1'S)-(+)-(2,7-di-tert-butyl-9,9-dimethyl-9H-xanthene-4,5-diyl)bis((2-methylphenyl)-(phenyl)phosphine)
(1S,1'S)-(–)-(2,7-di-tert-butyl-9,9-dimethyl-9H-xanthene-4,5-diyl)bis((4-methoxyphenyl)-(phenyl)phosphine)
(1S,1'S)-(–)-(2,7-di-tert-butyl-9,9-dimethyl-9H-xanthene-4,5-diyl)bis((4-methylphenyl)-(phenyl)phosphine)
(1S,1'S)-(–)-(2,7-di-tert-butyl-9,9-dimethyl-9H-xanthene-4,5-diyl)bis((4-napthyl)-(phenyl)phosphine)
(1S,1'S)-(–)-(2,7-di-tert-butyl-9,9-dimethyl-9H-xanthene-4,5-diyl)bis((2-naphthyl) (phenyl)phosphine)
(1S,1'S)-(–)-(2,7-di-tert-butyl-9,9-dimethyl-9H-xanthene-4,5-diyl)bis((9-phenanthryl)-(phenyl)phosphine)
(1S,1'S)-(–)-(2,7-di-tert-butyl-9,9-dimethyl-9H-xanthene-4,5-diyl)bis((3,5-dimethoxy-phenyl)(phenyl)phosphine)
(1S,1'S)-(+)-(2,7-di-tert-butyl-9,9-dimethyl-9H-xanthene-4,5-diyl)bis((2-isopropoxy-phenyl)(phenyl)phosphine)
(1S,1'S)-(+)-2,7-di-tert-butyl-9,9-dimethyl-9H-xanthene-4,5-diyl)bis((2-isopropylphenyl) (phenyl)phosphine)
(1S,1'S)-(–)-(2,7-di-tert-butyl-9,9-dimethyl-9H-xanthene-4,5-diyl)bis((2-ethoxyphenyl)-(phenyl)phosphine)
(1S,1'S-(–)-(2,7-di-tert-butyl-9,9-dimethyl-9H-xanthene-4,5-diyl)bis((3-methoxyphenyl)-(phenyl)phosphine)
(1S,1'S)-(–)-(2,7-di-tert-butyl-9,9-dimethyl-9H-xanthene-4,5-diyl)bis((3-isopropoxy-phenyl)(phenyl)phosphine)
(1S,1'S)-(–)-(2,7-di-tert-butyl-9,9-dimethyl-9H-xanthene-4,5-diyl)bis((dibenzo[b,d]-furan-4-yl)(phenyl)phosphine)
1S,1'S)-(–)-(2,7-di-tert-butyl-9,9-dimethyl-9H-xanthene-4,5-diyl)bis((2-ethylphenyl)-(phenyl)phosphine)
(1S,1'S)-(+)-(2,7-di-tert-butyl-9,9-dimethyl-9H-xanthene-4,5-diyl)bis((3-isopropylphenyl) (phenyl)phosphine)
(1S,1'S)-(+)-(2,7-di-tert-butyl-9,9-dimethyl-9H-xanthene-4,5-diyl)bis((3-methylphenyl)-(phenyl)phosphine)
(1S,1'S)-(+)-(2,7-di-tert-butyl-9,9-dimethyl-9H-xanthene-4,5-diyl)bis((3-ethylphenyl)-(phenyl)phosphine)
(1S,1'S)-(–)-(2,7-di-tert-butyl-9,9-dimethyl-9H-xanthene-4,5-diyl)bis((3-ethoxyphenyl)-(phenyl)phosphine)
(1S,1'S)-(+)-(2,7-di-tert-butyl-9,9-dimethyl-9H-xanthene-4,5-diyl)bis((4-(rac-2-methyl-butyl)phenyl)(phenyl)phosphine)
(1S,1'S)-(–)-(2,7-di-tert-butyl-9,9-dimethyl-9H-xanthene-4,5-diyl)bis((4-ethoxyphenyl)-(phenyl)phosphine)
(1S,1'S)-(–)-(oxybis(2,1-phenylene))bis((2-methoxyphenyl) (phenyl)phosphine)
(1S,1'S)-(–)-(oxybis(2,1-phenylene))bis((2-methylphenyl) (phenyl)phosphine)

(1S,1'S)-(−)-(oxybis(2,1-phenylene))bis((4-methoxyphenyl)(phenyl)phosphine)
(1S,1'S)-(−)-(oxybis(2,1-phenylene))bis((4-methylphenyl)(phenyl)phosphine)
(1S,1'S)-(−)-(oxybis(2,1-phenylene))bis((1-naphthyl)(phenyl)phosphine)
(1S,1'S)-(−)-(oxybis(2,1-phenylene))bis((2-naphthyl)(phenyl)phosphine)
(1R,1'R)-(+)-(oxybis(2,1-phenylene))bis((9-phenanthryl)(phenyl)phosphine)
(1S,1'S)-(−)-(oxybis(2,1-phenylene))bis((3,5-dimethoxyphenyl)(phenyl)phosphine)
(1S,1'S)-(+)-(oxybis(2,1-phenylene))bis((2-isopropylphenyl)(phenyl)phosphine)
(1S,1'S)-(+)-(oxybis(2,1-phenylene))bis((2-ethoxyphenyl)(phenyl)phosphine)
(1S,1'S)-(−)-(oxybis(2,1-phenylene))bis((3-methoxyphenyl)(phenyl)phosphine)
(1S,1'S)-(−)-(oxybis(2,1-phenylene))bis((3-isopropoxyphenyl)(phenyl)phosphine)
(1S,1'S)-(−)-(oxybis(2,1-phenylene))bis((dibenzo[b,d]furan-4-yl)(phenyl)phosphine)
(1S,1'S)-(−)-(oxybis(2,1-phenylene))bis((2-ethylphenyl)(phenyl)phosphine)
(1S,1'S)-(+)-(oxybis(2,1-phenylene))bis((3-isopropylphenyl)(phenyl)phosphine)
(1S,1'S)-(−)-(oxybis(2,1-phenylene))bis((3-methylphenyl)(phenyl)phosphine) and
(1S,1'S)-(−)-(oxybis(2,1-phenylene))bis((4-ethoxyphenyl)(phenyl)phosphine).

The invention further provides a process for preparing a chiral compound of the general formula (I), as defined above and below, in which a) a compound of the general formula (I.a)

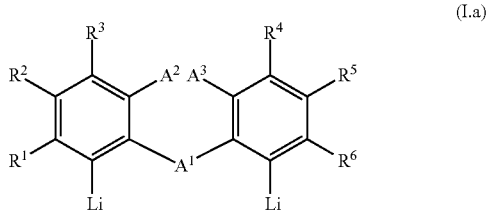

(I.a)

is provided, in which $A^1$, $A^2$, $A^3$, $R^1$, $R^2$, $R^3$, $R^4$, $R^5$ and $R^6$ have the meanings given above, b) a compound of the general formula (I.b1) is provided and, if $Ar^1$ and $Ar^3$ and $Ar^2$ and $Ar^4$ do not have the same meaning, a compound of the general formula (I.b2) is provided

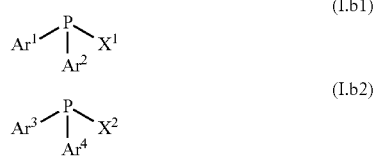

(I.b1)

(I.b2)

in which
$Ar^1$, $Ar^2$, $Ar^3$ and $Ar^4$ have the meanings given above, and
$X^1$ and $X^2$, independently of one another, are $C_1$-$C_4$-alkoxy,
and c) the compound of the general formula (I.a) is reacted with the compound of the general formula (I.b1) and, if present, with the compound of the general formula (I.b2), to give a compound of the general formula (I).

Step a)

Compounds of the formula (I.a) are obtainable by reaction of compounds of the formula II

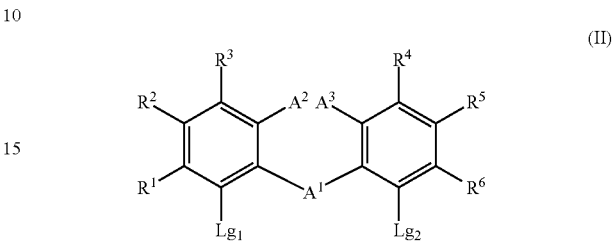

(II)

in which $R^1$, $R^2$, $R^3$, $R^4$, $R^5$, $R^6$, $A^1$, $A^2$ and $A^3$ have the meanings given above and Lg1 and Lg2 are hydrogen or halogen, with a lithium base. Specifically, Lg1 and Lg2 are Br. Suitable lithium bases are inorganic or organic lithium bases, in particular organic lithium bases such as n-butyllithium, sec-butyllithium, tert-butyllithium or phenyllithium. The reaction usually takes place in a solvent. Suitable solvents are ethers, specifically cyclic ethers such as tetrahydrofuran.

The reaction takes place usually at temperatures below 0° C., in particular below −50° C., specifically below −60° C.

Step b)

The borane-deprotected phosphinite compounds of the formula (I.b1) or (I.b2) are generally prepared only directly before the reaction from the corresponding borane-protected phosphinite compounds.

Step c)

The reaction takes place usually at low temperatures, e.g. below −30° C., In particular below −40° C. In a preferred embodiment, the compound of the formula (I.b2) has the same meaning as the compound of the formula (I.b1).

Preference is given to a process where, for providing the compounds of the general formula (I.b1) and, if $Ar^1$ and $Ar^3$ and $Ar^2$ and $Ar^4$ do not have the same meaning, (I.b2) in step b):

b1) an optically active ephedrine composition is subjected to a reaction with a compound of the general formula $Ar^1$—P(N($C_1$-$C_4$-alkyl)$_2$)$_2$ and a borane adduct to give an optically active compound of the general formula (III)

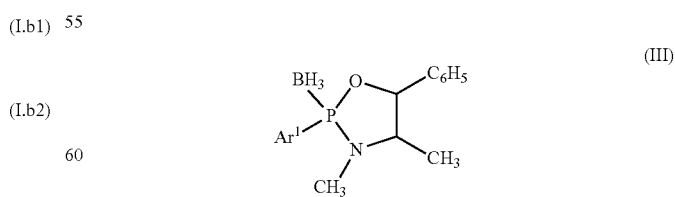

(III)

b2) the compound of the general formula (III) is subjected to a reaction with an aryllithium compound $Ar^2$—Li and then a proton donor to give an optically active compound of the general formula (IV)

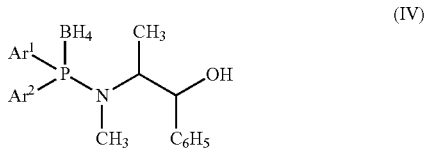

(IV)

b3) the compound of the general formula (IV) is subjected to a reaction with a ($C_1$-$C_4$)-alkanol to give an optically active compound of the general formula (V)

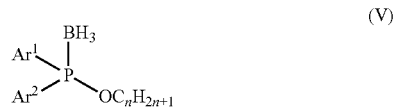

(V)

wherein n=1-4 b4) the compound of the general formula (V) is subjected to a reaction with a Lewis base to give an optically active compound of the general formula (I.b1)

(I.b1)

in which $X^1$ is $C_1$-$C_4$-alkoxy, where, for preparing a compound of the general formula (I.b2) in which $X^2$ is $C_1$-$C_4$-alkoxy, the reaction steps b1) to b4) are carried out with the proviso that, in step b1), an optically active ephedrine composition is subjected to a reaction with a compound of the general formula $Ar^3$—P(N($C_1$-$C_4$-alkyl)$_2$)$_2$ and a borane adduct and that, in step b2), the compound of the general formula (III) is subjected to a reaction with an aryllithium compound $Ar^4$—Li.

Step b1)

Optically active compounds of the formula III are obtainable by processes known in the literature, e.g. in accordance with A. J. Rippert, A. Linden, H.-J. Hansen, *Helv. Chim. Acta* 2000, 83, 311-321, or S. Jugé, M Stephan, J A. Laffitte, J. P. Genet *Tetrahedron Lett.* 1990, 31, 6357-6360. The borane adduct used in step b1) is preferably selected from borane-dimethyl sulfide or borane-THF.

Step b2)

The reaction of the compound of the formula III with an aryllithium compound $Ar^2$—Li to the compound (IV) is known per se, see Jugé, M Stephan, J. A. Laffitte, J. P. Genet *Tetrahedron Lett.* 1990, 31, 6357-6360 or C. Bauduin, D. Moulin, E. Kaloun, C. Darcel and S. Jugé, *J. Org. Chem.* 2003, 68, 4293-4301.

Step b3)

The compound (V) can be prepared according to the literature, see U. Nettekoven; P. C. J. Kamer; P. W. N. M. van Leeuwen; M. Widhalm; A. L Spek; M. Lutz, *J. Org. Chem.* 1999, 24, 3996-4004. Preferably, n is 1 in formula (V)

Step b4)

The cleaving off of the borane protective group from compounds of the formula V takes place with a Lewis base, such as e.g. diazabicyclo[2.2.2]octane. Usually, the deprotection takes place in the presence of a nonpolar solvent, e.g. hexane.

The invention further provides a chiral catalyst comprising or consisting of at least one transition metal complex which has at least one chiral compound of the general formula (I), as defined above, as ligand. As regards suitable and preferred compounds of the general formula (I), reference is made to the above details relating to suitable and preferred embodiments.

In addition to the above-described compounds (I) used as ligands, the catalysts used according to the invention can also have at least one further ligand which is preferably selected from hybrid, CO, olefins, dienes, cycloolefins, halides, amines, carboxylates, acetylacetonate (acac), aryl- or alkylsulfonates, nitriles, N-containing heterocycles, aromatics and heteroaromatics, ethers, PF3, phospholes, phosphabenzenes, and mono-dentate phosphine, phosphinite, phosphonite, phosphoramidite and phosphite ligands. The catalyst can comprise two or more different specified ligands. Preferred further ligands are e.g. hybrid, CO, dba (dibenzylidene acetone), norbonadiene or cod (1,5-cyclooctadiene). In one specific embodiment, the catalyst according to the invention does not comprise CO as ligand. Preferred ligands in that case are, for example, hydride, acac, dba, norbornadiene or cod.

Suitable transition metal complexes are, in particular, transition metal complexes of transition group VIII of the Periodic Table of the Elements. The transition metal is preferably Ru, Co, Rh, Ni, Pt, or Pd. Rh and Pd in particular are preferred.

The ratio of the amount of metal components of the catalyst, preferably rhodium or palladium, based on the total amount of the compound to be hydrogenated, is generally 1000:1 to 10:1, particularly preferably 500:1 to 50:1.

The molar amount ratio of ligand of the formula (I) to metal is generally in a range of about 1:1 to 50:1, preferably in a range from 1:1 to 10:1.

The catalysts can be used either directly in their active form, or else only be generated under the reaction conditions starting from transition metal sources with the addition of the corresponding ligands. Furthermore, it is possible for the catalysts according to the invention to be obtained by reaction of a corresponding metal salt or of a corresponding preliminary complex with the ligand of the general formula (I) and, optionally, further ligands, and subsequent isolation.

Suitable transition metal sources are quite generally transition metals, transition metal compounds and transition metal complexes, from which the hydrogenation catalyst is formed in situ under the hydrogenation conditions in the reaction zone.

Rhodium compounds or complexes suitable as transition metal source are e.g. rhodium(II) and rhodium(III) salts, such as rhodium(II) or rhodium(III) carboxylate, rhodium (II) and rhodium(III) acetate, etc. Also of suitability are rhodium complexes, such as rhodium biscarbonylacetylacetonate, acetylacetonatobisethylenerhodium(I), acetylacetonatocyclooctadienylrhodium(I), acetylacetonatonorbornadienylrhodium(I), acetylacetonatocarbonyltriphenylphosphinerhodium(I), etc.

Palladium compounds or complexes with suitability as a source of transition metal are, for example, palladium salts, such as palladium chlorides, bromides, iodides, cyanides, nitrates, acetates, acetylacetonates, hexafluoroacetylacetonates, tetrafluoroborates, etc. Also suitable are palladium complexes such as cyclooctadienepalladium chloride, cyclooctadienepalladium iodide, 1,5-hexadienepalladium chloride, 1,5-hexadienepalladium iodide, and bis(dibenzylideneacetone)palladium.

Likewise suitable are ruthenium salts or compounds. Examples of suitable ruthenium salts are ruthenium(III) chloride, ruthenium(IV) oxide, ruthenium (VI) oxide or ruthenium(VIII) oxide.

Examples of suitable cobalt salts or compounds are cobalt (II) chloride, cobalt(II) sulfate, cobalt(II) carbonate, cobalt (II) nitrate, their amine or hydrate complexes, or cobalt carboxylates.

The stated compounds of rhodium, palladium, cobalt, and ruthenium are available commercially or can be prepared by the person skilled in the art in analogy to compounds that are already known.

The invention further provides a process for preparing chiral compounds by reaction of a prochiral compound which comprises at least one ethylenically unsaturated double bond in the presence of a chiral catalyst comprising at least one transition metal complex with at least one compound of the general formula (I), as defined above, as ligand.

Contemplated in principle as prochiral, ethylenically unsaturated compounds for the process according to the invention are all prochiral compounds which contain one or more ethylenically unsaturated carbon-carbon or carbon-heteroatom bonds, examples being prochiral alkenes, aldehydes, and ketones.

In particular, it is a hydrogenation, allylic alkylation, hydroformylation, hydrocyanation, carbonylation, hydroacylation, hydroamidation, hydroesterification, hydrosilylation, hydroboration, aminolysis, alcoholysis, isomerization, metathesis, cyclopropanation or aldol condensation.

The reaction conditions of the processes according to the invention for the preparation of chiral compounds correspond generally, except for the chiral catalyst used, to those of the corresponding nonasymmetric processes. Suitable reactors and reaction conditions can therefore be found by the person skilled in the art in the relevant literature concerning the respective process, and routinely adapted. Suitable reaction temperatures are situated generally within a range from −100 to 500° C., preferably in a range from −80 to 250° C. Suitable reaction pressures are situated in general in a range from 0.0001 to 600 bar, preferably from 0.5 to 300 bar. The processes may in general take place continuously, semibatchwise, or batchwise. Suitable reactors for the continuous conversion are known to the person skilled in the art and are described for example in Ullmanns Enzyklopädie der technischen Chemie, vol. 1, 3rd edn., 1951, p. 743 ff. Suitable pressure-rated reactors are likewise known to a person skilled in the art and are described for example in Ullmanns Enzyklopädie der technischen Chemie, vol. 1, 3rd edition, 1951, p. 769 ff.

The processes of the invention can be carried out in a suitable solvent which is inert under the particular reaction conditions. Examples of solvents with general stability include aromatics, such as toluene and xylenes, or hydrocarbons or mixtures of hydrocarbons. Additionally suitable are halogenated hydrocarbons, especially chlorinated hydrocarbons, such as dichloromethane, trichloromethane or 1,2-dichloroethane. Further suitable solvents are esters of aliphatic carboxylic acids with alkanols, for example ethyl acetate or Texanol®, ethers such as tert-butyl methyl ether, 1,4-dioxane and tetrahydrofuran, and dimethylformamide. With sufficiently hydrophilized ligands it is also possible for use to be made of alcohols, such as methanol, ethanol, n-propanol, isopropanol, n-butanol, and isobutanol, and ketones, such as acetone and methyl ethyl ketone, etc. Further solvents which may be used include what are called "ionic liquids". These are liquid salts, examples being N,N'-dialkylimidazolium salts such as the N-butyl-N'-methylimidazolium salts, tetraalkylammonium salts such as the tetra-n-butylammonium salts, N-alkylpyridinium salts such as the n-butylpyridinium salts, tetraalkylphosphonium salts such as the trishexyl(tetradecyl)phosphonium salts, examples being the tetrafluoroborates, acetates, tetrachloroaluminates, hexafluoro-phosphates, chlorides, and tosylates. As solvent it is also possible to use a reactant, product or byproduct of the particular reaction.

In this way, through reaction of a prochiral compound containing at least one ethylenically unsaturated double bond with hydrogen in the presence of a chiral catalyst, as described above, corresponding chiral compounds with a single bond are obtained. Chiral, carbon-containing compounds are obtained from prochiral olefins; chiral alcohols are obtained from prochiral ketones; and chiral amines are obtained from prochiral imines.

Specifically, it is a hydrogenation or allylic alkylation.

The hydrogenation reaction can take place continuously, semicontinuously or discontinuously.

The hydrogenation takes place in a reaction zone which comprise one or more, identical or different reactors. In the simplest case, the reaction zone is formed by a single reactor. The reactors can in each case have identical or different mixing characteristics. The reactors can, if desired, be divided one or more times by internals. If two or more reactors form a zone, then these can be connected to one another as desired, e.g. in parallel or in series. Reactors that can be used are in principle all reactor types suitable for hydrogenation reactions, for example stirred reactors, bubble column reactors, circulation reactors, tubular reactors, with the individual reactors being able to have a number of different mixing characteristics. Suitable pressure-resistant reactors are likewise known to the person skilled in the art and are described e.g. in Ullmanns Enzyklopädie der technischen Chemie [Ullmanns Encyclopedia of Industrial Chemistry], volume 1, 3rd edition, 1951, p. 769 ff. Suitable reactors for the continuous reaction are moreover also known to the person skilled in the art and are described e.g. in Ullmanns Enzyklopädie der technischen Chemie [Ullmanns Encyclopedia of Industrial Chemistry], volume 1, 3rd edition, 1951, p. 743 ff.

The hydrogenation takes place advantageously at a pressure of about 0.5 to about 300 bar, advantageously 1 to about 300 bar, particularly preferably of about 1 to about 200 bar, in particular at about 1.1 to about 100 bar, specifically of about 1.2 to about 50 bar.

The hydrogenation takes place advantageously at a temperature of about 0 to 300° C., particularly preferably from 10 to 200° C., in particular from 20 to 100° C.

Suitable solvents are, for example, acyclic and cyclic ethers, specifically tetrahydrofuran and biphenyl ether, aromatic hydrocarbons, specifically toluene and xylene, halogenated aromatics, such as chlorobenzene, and long-chain alcohols, such as octadecanol, Texanol, Marlotherm, Oxo oil 9N (hydroformylation products of isomeric octenes, BASF SE).

Usually, the hydrogenation is concluded after about 30 minutes to about 100 hours, often after 1 hour to about 48 hours.

The resulting reaction product can be removed from the reaction mixture by processes known per se to the person skilled in the art, such as e.g. by distillation, and the catalyst that is left behind can be used in the course of further reactions, optionally after repeated preformation.

The hydrogenation is suitable particularly for reactions on an industrial scale. The hydrogenation by the process according to the invention is notable for high stereoselectivity.

In particular, the process according to the invention is an allylic alkylation. Accordingly, by reaction of a prochiral ketone or aldehyde with an allylic alkylating agent in the presence of a chiral catalyst, as described above, chiral hydrocarbons are obtained. The reaction is carried out advantageously in the presence of a two-component system of N,O-bis(trimethyl)acetamide and potassium acetate. The allylic alkylation by the process according to the invention is notable for high stereoselectivity.

According to a further preferred embodiment, the process according to the invention is a hydroformylation. Accordingly, from a prochiral compound which contains at least one ethylenically unsaturated double bond, using carbon monoxide and hydrogen in the presence of a chiral catalyst, as described above, aldehydes are obtained. Substrates contemplated for the hydroformylation process include in principle all compounds which contain one or more ethylenically unsaturated double bonds. These include, for example, alkenes, such as α-alkenes, internal linear and internal branched alkenes, cycloalkenes, vinylaromatics, α,β-ethylenically unsaturated monocarboxylic and/or dicarboxylic acids, their esters, monoesters and amides, dienes or polyenes having isolated or conjugated double bonds, and unsaturated nitriles.

The aldehydes obtained may optionally be hydrogenated in the same operation with hydrogen to give the corresponding oxo-process alcohols.

According to a further preferred embodiment, the process of the invention is a hydrocyanation. Accordingly, from a prochiral compound containing at least one ethylenically unsaturated double bond, using hydrogen cyanide, nitriles are obtained.

According to a further preferred embodiment, the process according to the invention is a reaction with carbon monoxide and with at least one compound having a nucleophilic group, referred to hereinafter as carbonylation.

Preferably the compounds with a nucleophilic group are [lacuna], selected from water, alcohols, thiols, carboxylic esters, primary and secondary amines.

A preferred carbonylation reaction is the conversion of olefins with carbon monoxide and water to give carboxylic acids (hydrocarboxylation). A further preferred carbonylation reaction is the conversion olefins with carbon monoxide and alcohols to give carboxylic acid esters (alkoxycarbonylation).

The carbonylation may take place in the presence of activating agents. Examples of suitable activating agents are Brönsted acids, Lewis acids, such as $BF_3$, $AlCl_3$, $ZnCl_2$, and Lewis bases.

According to a further preferred embodiment, the process according to the invention is a hydroacylation. Accordingly, in the asymmetric intramolecular hydroacylation, by reaction of an unsaturated aldehyde, optically active cyclic ketones are obtained. In the asymmetric intermolecular hydroacylation, by reaction of a prochiral olefin with an acyl halide in the presence of a chiral catalyst, as described above, chiral ketones are obtained. Suitable methods for hydroacylation are described in J. March, Advanced Organic Chemistry, 4th edn., p. 811, to which reference is hereby made.

According to a further preferred embodiment, the process according to the invention is a hydroamidation. Accordingly, by reaction of a prochiral compound containing at least one ethylenically unsaturated double bond, using carbon monoxide and ammonia, or using a primary or secondary amine, in the presence of a chiral catalyst as described above, chiral amides are obtained.

According to a further preferred embodiment, the process according to the invention is a hydroesterification. Accordingly, by reaction of a prochiral compound containing at least one ethylenically unsaturated double bond, using carbon monoxide and an alcohol in the presence of a chiral catalyst, as described above, chiral esters are obtained.

According to a further preferred embodiment, the process according to the invention is a hydroboration. Accordingly, by reaction of a prochiral compound containing at least one ethylenically unsaturated double bond with borane or a borane source in the presence of a chiral catalyst, as described above, chiral trialkylboranes are obtained, which can be oxidized to primary alcohols (e.g. with $NaOH/H_2O_2$) or to carboxylic acids. Suitable methods for hydroboration are described in J. March, Advanced Organic Chemistry, 4th edn., pp 783-789, to which reference is made.

According to a further preferred embodiment, the process according to the invention is a hydrosilylation. Accordingly, by reacting a prochiral compound containing at least one ethylenically unsaturated double bond with a silane in the presence of a chiral catalyst, as described above, chiral compounds functionalized with silyl groups are obtained. Prochiral olefins result in chiral alkanes functionalized with silyl groups. Prochiral ketones result in chiral silyl ethers or silyl alcohols. With the hydrosilylation catalysts, the transition metal is preferably selected from Pt, Pd, Rh, Ru, and Ir. It may be of advantage here to use combinations or mixtures of one of the above-stated catalysts with other catalysts. The suitable additional catalysts include, for example, platinum in finely divided form ("platinum black"), platinum chloride, and platinum complexes such as hexachloroplatinic acid or divinyldisiloxane-platinum complexes, e.g. tetra-methyl-divinyldisiloxane-platinum complexes.

Suitable silanes are, for example, halogenated silanes, such as trichlorosilane, methyl-dichlorosilane, dimethyl-chlorosilane and trimethylsiloxydichlorosilane; alkoxysilanes, such as trimethoxysilane, triethoxysilane, methyldi-methoxysilane, phenyldimethoxy-silane, 1,3,3,5,5,7,7-heptamethyl-1,1-dimethoxytetrasiloxane, and also acyloxysilanes.

According to a further preferred embodiment, the process according to the invention is an aminolysis (hydroamination). Accordingly, by reaction of a prochiral compound containing at least one ethylenically unsaturated double bond with ammonia, with a primary or with a secondary amine in the presence of a chiral catalyst, as described above, chiral primary, secondary or tertiary amines are obtained. Suitable methods for hydroamination are described in J. March, Advanced Organic Chemistry, 4th edn., pp. 768-770, to which reference is hereby made.

According to a further preferred embodiment, the process according to the invention is an alcoholysis (hydro-alkoxy addition). Accordingly, by reaction of a prochiral compound containing at least one ethylenically unsaturated double bond with alcohols in the presence of a chiral catalyst, as described above, chiral ethers are obtained. Suitable methods for alcoholysis are described in J. March, Advanced Organic Chemistry, 4th edn., pp. 763-764, to which reference is hereby made.

According to a further preferred embodiment, the process according to the invention is an isomerization. Accordingly, from a prochiral compound containing at least one ethylenically unsaturated double bond, in the presence of a chiral catalyst, as described above, chiral compounds are obtained.

According to a further preferred embodiment, the process according to the invention is a cyclopropanation. Accordingly, from a prochiral compound containing at least one ethylenically unsaturated double bond, with a diazo compound in the presence of a chiral catalyst, as described above, chiral cyclopropanes are obtained.

According to a further preferred embodiment, the process according to the invention is a metathesis. Accordingly, from a prochiral compound containing at least one ethylenically unsaturated double bond, with a further olefin in the presence of a chiral catalyst, as described above, chiral hydrocarbons are obtained.

According to a further preferred embodiment, the process according to the invention is an aldol condensation. Accordingly, by reacting a prochiral ketone or aldehyde with a silylenol ether in the presence of a chiral catalyst, as described above, chiral aldols are obtained.

The catalysts according to the invention are particularly suitable in the asymmetric hydrogenation of C=C bonds, in which they exhibit high activities and selectivities, and in asymmetric allylic alkylation. A particularly advantageous feature is that the ligand of the general formula (I), by virtue of its simple, broad capacity for modification, can be tailored very well, sterically and electronically, to the particular substrate and the catalytic reaction.

The invention further provides a process for preparing an optically active carbonyl compound by asymmetric hydrogenation of a prochiral α,β-unsaturated carbonyl compound with hydrogen in the presence of at least one transition metal catalyst which has rhodium as catalytically active transition metal and a chiral compound of the general formula (I), as defined above and below, as ligand. Specifically, the asymmetric hydrogenation is carried out in the presence of an optically active transition metal catalyst that is soluble in the reaction mixture and which has rhodium as catalytically active transition metal and a chiral compound of the general formula (I), as defined above and below, as ligand.

Preferably, the prochiral α,β-unsaturated carbonyl compound is a prochiral, α,β-unsaturated ketone or a prochiral, α,β-unsaturated aldehyde.

In a preferred embodiment, the prochiral α,β-unsaturated carbonyl compound is selected from compounds of the general formula (II)

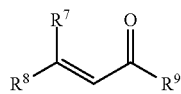

(II)

in which
$R^7$, $R^8$ are different from one another and in each case is an unbranched, branched or cyclic hydrocarbon radical having 1 to 25 carbon atoms which is saturated or has one or more nonconjugated ethylenic double bonds, and which is unsubstituted or carries one or more identical or different substituents which is selected from $OR^{10}$, $NR^{11a}R^{11b}$, halogen, $C_6$-$C_{10}$-aryl and hetaryl with 5 to 10 ring atoms,
$R^9$ is hydrogen or an unbranched, branched or cyclic hydrocarbon radical having 1 to 25 carbon atoms which is saturated or has one or more nonconjugated ethylenic double bonds, and which is unsubstituted or carries one or more identical or different substituents which are selected from $OR^{10}$, $NR^{11a}R^{11b}$, halogen, $C_6$-$C_{10}$-aryl and hetaryl with 5 to 10 ring atoms,
or
$R^9$ together with one of the radicals $R^7$ or $R^8$ can also be a 3- to 25-membered alkylene group in which 1, 2, 3 or 4 nonadjacent $CH_2$ groups can be replaced by O or N—$R^{11c}$, where the alkylene group is saturated or has one or more nonconjugated ethylenic double bonds, and where the alkylene group is unsubstituted or carries one or more identical or different substituents which are selected from $OR^{10}$, $NR^{11a}R^{11b}$, halogen, $C_1$-$C_4$-alkyl, $C_6$-$C_{10}$-aryl and hetaryl with 5 to 10 ring atoms, where two substituents can also together be a 2- to 10-membered alkylene group, where the 2- to 10-membered alkylene group is saturated or has one or more nonconjugated ethylenic double bonds, and where the 2- to 10-membered alkylene group is unsubstituted or carries one or more identical or different substituents which are selected from $OR^{10}$, $NR^{11a}R^{11b}$, halogen, $C_6$-$C_{10}$-aryl and hetaryl with 5 to 10 ring atoms;
where
$R^{10}$ is hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl;
$R^{11a}$, $R^{11b}$ are in each case independently of one another hydrogen, $C_1$-$C_6$-alkyl, $C_6$-$C_{10}$-aryl, $C_6$-$C_{14}$-aryl-$C_1$-$C_{10}$-alkyl or $C_1$-$C_{10}$-alkyl-$C_6$-$C_{14}$-aryl or
$R^{11a}$ and $R^{11b}$ can together also be an alkylene chain having 2 to 5 carbon atoms which can be interrupted by N or O; and
$R^{11c}$ is hydrogen, $C_1$-$C_6$-alkyl, $C_6$-$C_{10}$-aryl, $C_6$-$C_{14}$-aryl-$C_1$-$C_{10}$-alkyl or $C_1$-$C_{10}$-alkyl-$C_6$-$C_{14}$-aryl.

In particular, the prochiral α,β-unsaturated carbonyl compound is selected from compounds of the general formulae (IIa) and (IIb)

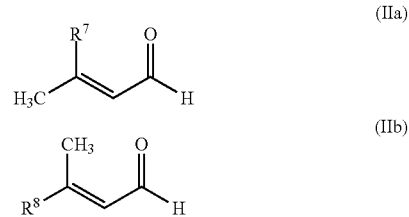

in which
$R^7$, $R^8$ is in each case an unbranched or branched hydrocarbon radical having 2 to 25 carbon atoms which is saturated or has 1, 2, 3, 4 or 5 nonconjugated ethylenic double bonds.

Of major importance for catalyst performance is not only the catalytic activity but also the enantioselectivity achieved. The measure of enantioselectivity is the enantiomeric excess (ee) achieved. The enantioselectivity of the asymmetric hydrogenation by the process according to the invention, for prochiral α,β-unsaturated carbonyl compounds as substrate, can be demonstrated advantageously with cyclic prochiral α,β-unsaturated carbonyl compounds, since with these compounds there is no complication of substrate isomerization. The model substrate used in the experimental part of this specification, therefore, was isophorone, which is not isomerizable. The results of the asymmetric hydrogenation of isophorone demonstrate the high stereoselectivity of the process according to the invention. The process according to the invention therefore allows the preparation of optically active products with high enantioselectivity. Enantiomeric excesses (ee) of at least 70% can be achieved, preferably at least 80% and more particularly at least 90%.

The invention further provides a process for preparing optically active citronellal of the formula (VI)

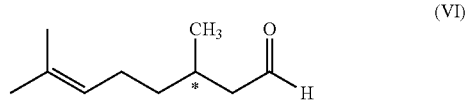

in which * designates the asymmetry center;
by asymmetric hydrogenation of geranial of the formula (IIa-1) or of neral of the formula (IIb-1)

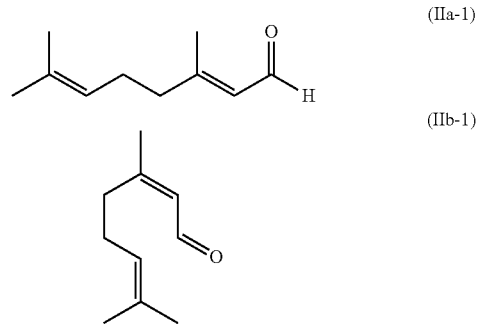

or a mixture comprising neral and geranial.

The hydrogenation according to the invention for the preparation of citronellal (VI), starting from neral and/or geranial, takes place preferably at temperatures of 0 to 60° C., under a hydrogen pressure of 0.5 to 100 bar, and using chiral compounds of the formula (I) as directing organic ligands for the catalyst according to the invention. The catalysts used in the process according to the invention comprise rhodium as catalytically active transition metal. In general, with the hydrogenation according to the invention, the rhodium concentration in the reaction medium is in a range from about 1 to 10 000 ppm.

The molar amount ratio of ligand to transition metal is generally in a range from about 0.5:1 to 100:1, preferably 1:1 to 50:1, especially 2:1 to 10:1.

The molar amount ratio of total geranial and/or neral for hydrogenation to rhodium transition metal is generally in a range from about 10:1 to 500 000:1, preferably 100:1 to 50 000:1.

The catalyst systems used in the process according to the invention may have, in addition to the above-described diphosphine ligands, at least one further ligand. Further ligands are preferably selected from cycloolefins, acetylacetonate, carboxylates, arylsulfonates, alkylsulfonates, hydride, olefins, dienes, nitriles, halogen, aromatics and heteroaromatics, ethers, and non-diphosphine unidentate, bidentate and polydentate ligands containing phosphorus atoms.

The hydrogenation may be carried out without an external solvent or in a suitable solvent which is inert under the respective reaction conditions. Suitable solvents are, for example, aromatics, such as toluene and xylenes, hydrocarbons or mixtures of hydrocarbons, ethers such as tetrahydrofuran or 1,4-dioxane, esters of aliphatic carboxylic acids with alkanols, an example being Texanol®, and esters of aromatic carboxylic acids, e.g. C8-C13-dialkyl phthalates. Particularly preferred solvents are toluene or tetrahydrofuran.

In contrast to known processes, the reaction can be carried out under relatively low hydrogen pressures and at low temperatures.

The hydrogenation takes place preferably at a temperature in the range from 5 to 50° C., preferably from 10 to 40° C.

The hydrogenation takes place preferably under a hydrogen pressure of 0.5 to 80 bar, more preferably 0.7 to 50 bar.

At reaction temperatures of 10 to 30° C., preferably 25° C., and a hydrogen pressure of 1 bar, very good results, particularly with regard to selectivity, can already be achieved.

The invention further provides a process for preparing optically active menthol, in which optically active citronellal of the formula (IV), obtainable by a process as defined above, is subjected to a cyclization to give optically active isopulegol, and the optically active isopulegol is hydrogenated to give optically active menthol.

Processes for preparing optically active menthol by cyclization of optically active citronellal to give optically active isopulegol and hydrogenation of optically active isopulegol to give optically active menthol are known to the person skilled in the art and described e.g. In WO 2006/056435.

The invention is described in more detail by reference to the following non-limiting examples.

EXAMPLES

The following examples serve to illustrate the invention without limiting it.

Abbreviations

| | |
|---|---|
| EtOAc | ethyl acetate |
| Ar | aryl |
| BSA | N,O-bis(trimethylsilyl)acetamide |
| Bu | butyl |
| DABCO | 1,4-diazobicyclo[2.2.2]octane |
| Et | ethyl |
| EtO or OEt | ethoxy |
| i-PrOH | isopropanol |
| Me | methyl |
| MeO or OMe | methoxy |
| MeOH | methanol |
| Pd(dba)$_2$ | bis(dibenzylideneacetone)palladium(0) |
| Ph | phenyl |
| sec | secondary |
| THF | tetrahydrofuran |
| TMEDA | N,N,N',N',-tetramethylethylenediamine |
| cal. | calculated for |
| ex. | example |
| fnd. | found |
| SOLV. | solvent |
| m.p. | melting point |
| CC | column chromatography |
| $t_R$ | retention time |

EXAMPLES

I. Preparation of Chiral Phosphine Ligands of the Formula I

I.1 Preparation of Precursors

Example 1

(2R,4S,5R)-2,3,4,5-Tetrahydro-3,4-dimethyl-2,5-diphenyl-1,3,2-oxazaphosphole-2-borane The preparation was carried out in a manner known per se by reaction of (1R,2S)-(−) ephedrine with bis(diethylamino)phenylphosphine and dimethyl sulfide-borane ($BH_3 \cdot (CH_3)_2S$), with the reaction time being extended to 72 hours, see A. J. Rippert, A. Linden, H.-J. Hansen *Helv. Chim. Acta* 2000, 83, 311-321, or S. Jugé, M Stephan, J. A. Laffitte, J. P. Genet *Tetrahedron Let.* 1990, 31, 6357-6360.

m.p.=108-109° C. (from i-PrOH);
$[\alpha]_D^{22}$=+2.4 (c1.0, $CHCl_3$);
$^1$H-NMR ($CDCl_3$): δ 7.89-7.76 (2H, m, arom H), 7.60-7.44 (3H, m, arom H), 7.43-7.27 (5H, m, arom H), 5.60 (1H, dd, J 6.2, 3.2 Hz, CH—O), 3.67 (1H, m, CH—N), 2.66 (3H, d, J 10.8 Hz, $CH_3$—N), 0.81 (3H, d, J 6.5 Hz, $CH_3$), 1.60-0.40 (3H, br q, $BH_3$);
$^{13}$C-NMR ($CDCl_3$): δ 136.1 (d, J 5.1 Hz, C—C), 132.8 (d, J 44.6 Hz, C—P), 132.3 (d, J 2.0 Hz, CH), 132.3 (d, J 12.1 Hz, 2×CH), 128.5 (d, J 9.8 Hz, 2×CH), 128.3 (2×CH), 128.3 (CH), 126.6 (2×CH), 84.1 (d, J 7.5 Hz, CH—O), 58.9 (d, J 1.6 Hz, CH—N), 29.4 (d, J 8.0 Hz, $CH_3$N), 13.5 (d, J 3.5 Hz, $CH_3$); $^{31}$P-NMR ($CDCl_3$): δ +133.4.

Example 1*

(2S,4R,5S)-2,3,4,5-Tetrahydro-3,4-dimethyl-2,5-diphenyl-1,3,2-oxazaphosphole-2-borane The title compound was prepared analogously to the process described in example 1, using (1S,2R)-(+)-ephedrine instead of (−)-ephedrine.

Example 2

General Operating Procedure for the Preparation of (1R,2S)-2-{[(S)-(aryl)phenylphosphanyl]methylamino}-1-phenylpropan-1-ol P-Borane Complexes 2a-u

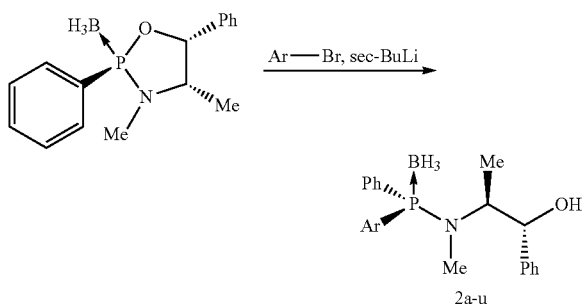

2a-u

The preparation of the aryllithium reagents was carried out in a manner known per se, see C. Bauduin, D. Moulin, E. B. Kaloun, C. Darcel, S. Jugé *J. Org. Chem.* 2003, 68, 4293-4301.

In a Schlenk vessel, 20 mmol of the corresponding aryl bromide were slowly added via syringe to 20 mmol of sec-BuLi (15.4 ml of a 1.3 M solution) at 0° C. After further stirring for 1 hour, the suspension was carefully admixed with 5 ml of THF. In another Schlenk vessel, 10 mmol (2.85 g) of (2R,4S,5R)-2,3,4,5-tetrahydro-3,4-dimethyl-2,5-diphenyl-1,3,2-oxazaphosphole (compound from example 1) in THF (10 ml) were initially introduced at −78° C. and slowly admixed with the aryllithium solution via cannula. Completion was attained by further stirring overnight at room temperature. For the work-up, the suspension was cooled again to 0° C. and carefully admixed with water (5 ml). Then, the reaction solution was extracted with dichloromethane (3×30 ml), and the organic phase was dried with $Na_2SO_4$. The solvent was removed. The target compound was obtained by column chromatography over silica gel or crystallization.

The following compounds were prepared according to the general operating procedure:

(1R,2 S)-2-{[(S)-(2-Methoxyphenyl)phenylphosphanyl]methylamino}-1-phenylpropan-1-ol P-borane complex (compound 2a)
Yield: 91%; m.p.=120° C. (from i-PrOH/hexane);
$[\alpha]_D^{21}$=+39.4 (c1.0, $CH_2Cl_2$).

(1R,2S)-2-{[(S)-(2-Methylphenyl)phenylphosphanyl]methylamino}-1-phenylpropan-1-ol P-borane complex (compound 2b)
Yield: 89%; m.p.=119-120° C. (CC with cyclohexane/EtOAc 19/1 to 9/1);
$[\alpha]_D^{21}$=+75.0 (c1.0, $CHCl_3$).

(1R,2S)-2-{[(S)-4-Methoxyphenyl)phenylphosphanyl]methylamino}-1-phenylpropan-1-ol P-borane complex (compound 2c)
Yield: 90%; m.p.=53-54° C. (CC with cyclohexane/EtOAc 9/1);
$[\alpha]_D^{22}$=+39.6 (c1.0, $CHCl_3$).

(1R,2S)-2-{[(S)-(4-Methylphenyl)phenylphosphanyl]methylamino}-1-phenylpropan-1-ol P-borane complex (compound 2d)
Yield: 42%; m.p.=47-48° C. (CC with cyclohexane/EtOAc 19/1 to 9/1); $[\alpha]_D^{22}$=+44.6 (c1.0, $CHCl_3$).

(1R,2S)-2-{[(S)-(1-Naphthyl)phenylphosphanyl]methylamino}-1-phenylpropan-1-ol P-borane complex (compound 2e)
Yield: 87%; m.p.=120-122° C. (CC with heptane/EtOAc 9/1-4/1); $[\alpha]_D^{22}$=+93.2 (c1.0, $CHCl_3$).

(1R,2S)-2-{[(S)-(2-Naphthyl)phenylphosphanyl]methylamino}-1-phenylpropan-1-ol P-borane complex (compound 2f)
Yield: 85%; m.p.=135-136° C. (i-PrOH/hexane); $[\alpha]_D^{22}$=+59.8 (c1.1, $CH_2Cl_2$).

(1R,2S)-2-{[(S)-(9-Phenanthryl)phenylphosphanyl]methylamino}-1-phenylpropan-1-ol P-borane complex (compound 2g);
Yield: 79%; m.p.=76-78° C. (SC with cyclohexane/EtOAc 19/1 to 4:1);
$[\alpha]_D^{24}$=+93.0 (c1, $CHCl_3$).

(1R,2S)-2-{[(S)-(3,5-Dimethoxyphenyl)phenylphosphanyl]methylamino}-1-phenylpropan-1-ol P-borane complex (compound 2h)
Yield: 87%; m.p.=48-49° C. (CC with cyclohexane/EtOAc 9/1 to 4/1);
$[\alpha]_D^{23}$=+41.3 (c1.0, $CHCl_3$).

(1R,2S)-2-{[(S)-(2-Isopropoxyphenyl)phenylphosphanyl]methylamino}-1-phenylpropan-1-ol P-borane complex (compound 2i)

Yield: 80% white solid; m.p.=48-52° C. (CC with cyclohexane/EtOAc 4/1); $[\alpha]_D^{22}$=+23.2 (c1.0, CHCl$_3$).

(1R,2S)-2-{[(S)-(2-Isopropylphenyl)phenylphosphanyl]methylamino}-1-phenylpropan-1-ol P-borane complex (compound 2j)
Yield: 72% white solid; m.p.=54-58° C. (CC with cyclohexane/EtOAc 9/1);
$[\alpha]_D^{22}$=+32.2 (c1.0, CHCl$_3$).

(1R,2S)-2-{[(S)-(2-Ethoxyphenyl)phenylphosphanyl]methylamino}-1-phenylpropan-1-ol P-borane complex (compound 2k)
Yield: 88% white solid; m.p.=50-52° C. (CC with cyclohexane/EtOAc 19/1 to 9/1);
$[\alpha]_D^{23}$=+27.7 (c1.0, CHCl$_3$).

(1R,2S)-2-{[(S)-(3-Methoxyphenyl)phenylphosphanyl]methylamino}-1-phenylpropan-1-ol P-borane complex (compound 2l)
Yield: 92% of viscous syrup (CC with cyclohexane/EtOAc 9/1 to 4/1);
$[\alpha]_D^{23}$=+43.6 (c1.0, CHCl$_3$).

(1R,2S)-2-{[(S)-(3-Isopropoxyphenyl)phenylphosphanyl]methylamino}-1-phenylpropan-1-ol P-borane complex (compound 2m)
Yield: 88% white solid; m.p.=45-47° C. (CC with cyclohexane/EtOAc 19/1);
$[\alpha]_D^{23}$=+39.0 (c1.0, CHCl$_3$).

(1R,2S)-2-{[(S)-(Dibenzo[b,d]furan-4-yl)phenylphosphanyl]methylamino}-1-phenylpropan-1-ol P-borane complex (compound 2n)
As modification to the general procedure, the synthesis of the aryllithium compound of the dibenzofuran was carried out by reacting dibenzofuran with 1.1 equivalents of an n-butyllithium solution in THF (−30° C. to room temperature, 20 h).
Yield: 82% white solid; m.p.=60-64° C. (CC with cyclohexane/EtOAc 9/1);
$[\alpha]_D^{22}$=+71.0 (c1.0, CHCl$_3$).

(1R,2S)-2-{[(S)-(2-Ethylphenyl)phenylphosphanyl]methylamino}-1-phenylpropan-1-ol P borane complex (compound 2o)
Yield: 79% white residue; m.p.=46-48° C. (CC with cyclohexane/EtOAc 19/1 to 9/1);
$[\alpha]_D^{23}$=+46.5 (c1.0, CHCl$_3$).

(1R,2S)-2-{[(S)-(3-Isopropylphenyl)phenylphosphanyl]methylamino}-1-phenylpropan-1-ol P-borane complex (compound 2p)
Yield: 88% viscous, pale yellow syrup (CC with cyclohexane/EtOAc 19/1 to 4/1);
$[\alpha]_D^{23}$=+44.2 (c1.0, CHCl$_3$).

(1R,2S)-2-{[(S)-(3-Methylphenyl)phenylphosphanyl]methylamino}-1-phenylpropan-1-ol P-borane complex (compound 2q)
Yield: 87% white solid; m.p.=38-40° C. (CC with cyclohexane/EtOAc 19/1);
$[\alpha]_D^{23}$=+45.6 (c1.0, CHCl$_3$).

(1R,2S)-2-{[(S)-(3-Ethylphenyl)phenylphosphanyl]methylamino}-1-phenylpropan-1-ol P borane complex (compound 2r)
Yield: 92% colorless viscous syrup (CC with cyclohexane/EtOAc 19/1);
$[\alpha]_D^{23}$=+42.0 (c1.0, CHCl$_3$);

(1R,2S)-2-{[(S)-(3-Ethoxyphenyl)phenylphosphanyl]methylamino}-1-phenylpropan-1-ol P-borane complex (compound 2s)
Yield: 90% white solid; m.p.=95° C. (CC with cyclohexane/EtOAc 9/1);
$[\alpha]_D^{23}$=+41.3 (c1.0, CHCl$_3$).

(1R,2S)-2-{[(S)-(4-(rac-2-methylbutyl)phenyl)phenylphosphanyl]methylamino}-1-phenylpropan-1-ol P-borane complex (compound 2t)
This compound resulted as byproduct by alkylation of the methyl group during the preparation of 2d
Yield: 45% white solid; m.p.=45-46° C. (CC with cyclohexane/EtOAc 19/1 to 9/1);
$[\alpha]_D^{22}$=+36.3 (c1.0, CHCl$_3$).

(1R,2S)-2-{[(S)-(4-Ethoxyphenyl)phenylphosphanyl]methylamino}-1-phenylpropan-1-ol P-borane complex (compound 2u)
Yield: 71% white solid; m.p.=48-49° C. (CC with cyclohexane/EtOAc 9/1);
$[\alpha]_D^{22}$=+35.6 (c1.0, CHCl$_3$).

Example 2*

The enantiomers to the compounds 2a-2u were obtainable analogously by reacting (2S,4R,5S)-2,3,4,5-tetrahydro-3,4-dimethyl-2,5-diphenyl-1,3,2-oxazaphosphole-2-borane from example 1* with the corresponding aryllithium compound.

Example 3

General Operating Procedure for the Synthesis of the Methyl (S)-(Aryl)Phenylphosphinites P-Borane Complexes (3a-u)

The preparation of the chiral phosphinous acid methyl esters 3a-u was carried out in a known manner by treating the P-amide compounds 2a-u with methanol/sulfuric acid, see U. Nettekoven, P. C. J. Kamer, P. W. N. M. van Leeuwen, M. Widhalm, A. L. Spek, M. Lutz *J. Org. Chem.* 1999, 24, 3996-4004.

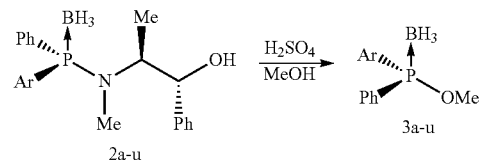

In each case 10 mmol of the P-amide compound 2a-u were initially introduced in degassed methanol (90 ml) at 0° C. and then slowly admixed with concentrated sulfuric acid (10 mmol, 0.98 g). Stirring was continued for a further 20 hours at room temperature and, after removal of the solvent, the compounds 3a-u were isolated by column chromatography.

Methyl (R)-(−)-(2-methoxyphenyl)phenylphosphinite borane complex (compound 3a)
Yield 87%; colorless oil (CC with cyclohexane/EtOAc 9/1);
$[\alpha]_D^{24}$=−30.8 (c1.0, CH$_2$Cl$_2$).
HPLC: purity >99% ee; column: Chiralcel OJ-H (150×4.6 mm), hexane/i-PrOH 92/8, 1.00 ml/min, $t_R$=11.0 min (S)-enantiomer and 16.9 min (R)-enantiomer.

Methyl (R)-(+)-(2-methylphenyl)phenylphosphinite borane complex (compound 3b)
Yield 76%, colorless oil (CC with cyclohexane/EtOAc 19/1);
$[\alpha]_D^{23}$=+3.8 (c1.0, CHCl$_3$);
HPLC: purity >99% ee; column: Chiralcel OJ-H (150×4.6 mm), hexane/i-PrOH 95/5, 1.00 ml/min, $t_R$=7.8 min (S)-enantiomer and 11.8 min (R)-enantiomer.

Methyl (R)-(+)-(4-methoxyphenyl)phenylphosphinite borane complex (compound 3c)
Yield 81%; colorless oil (CC with cyclohexane/EtOAc 19/1);
$[\alpha]_D^{25}$=+38.3 (c1.07, CHCl$_3$);
HPLC: purity >99% ee; Chiralpak AS-H (150×0.46 mm), hexane/i-PrOH 99.5/0.5, 1.00 ml/min, t$_R$=8.8 min (S)-enantiomer and 10.5 min (R)-enantiomer.

Methyl (R)-(+)-(4-methylphenyl)phenylphosphinite borane complex (compound 3d)
Yield 86%; colorless oil (CC with cyclohexane/EtOAc 9/1);
$[\alpha]_D^{26}$=+13.3 (c1.0, CHCl$_3$);
HPLC: purity 97% ee; Chiralcel OJ-H (150×4.6 mm), hexane/EtOH 85/15, 1.00 ml/min, t$_R$=9.2 min (S)-enantiomer and 15.9 min (R)-enantiomer.

Methyl (R)-(−)-(1-naphthyl)phenylphosphinite borane complex (compound 3e)
Yield 82%; white crystals m.p.=67-68° C. (CC with cyclohexane/EtOAc 9/1);
$[\alpha]_D^{19}$=−23.3 (c1.0, CH$_2$Cl$_2$);
HPLC: purity 98% ee; Reprosil 100 (150×4.6 mm), hexane/i-PrOH 99.75/0.25, 1.25 ml/min, t$_R$=8.0 min (R)-enantiomer and 9.0 min (S)-enantiomer.

Methyl (R)-(+)-(2-naphthyl)phenylphosphinite borane complex (compound 3f)
Yield 91%; colorless crystals m.p.=88-89° C. (CC with cyclohexane/EtOAc 9/1);
$[\alpha]_D^{22}$=+44.3 (c1.0, CH$_2$Cl$_2$);
HPLC: purity >99%; Chiralpak AD-H (150×4.6 mm), hexane/i-PrOH 99.5/0.5, 1.00 ml/min, t$_R$=10.5 min (S)-enantiomer and 13.0 min (R)-enantiomer.

Methyl (R)-(+)-(9-phenanthryl)phenylphosphinite borane complex (compound 3g)
Yield 66%; white crystals m.p.=143-144° C. (CC with cyclohexane/EtOAc 9/1 to 4:1);
$[\alpha]_D^{21}$=+78.4 (c1, CHCl$_3$);
HPLC: purity >98% ee; column: Chiralcel OD-H (150× 4.6 mm), hexane/i-PrOH 97/3, 1.00 ml/min, t$_R$=5.3 min (R)-enantiomer and 7.9 min (S)-enantiomer.

Methyl (S)-(−)-(9-phenanthryl)phenylphosphinite borane complex (compound 3g*)
The title compound was prepared in an analogous manner starting from (2S,4R,5S)-2,3,4,5-tetrahydro-3,4-dimethyl-2,5-diphenyl-1,3,2-oxazaphosphole-2-borane from example 1*, subsequent reaction with 9-phenanthryl bromide and sec-BuLi, followed by treatment of the resulting compound with methanol/H$_2$SO$_4$.

Methyl (R)-(−)-(3,5-dimethoxyphenyl)phenylphosphinite borane complex (compound 3h)
Yield 75%; colorless oil (CC with cyclohexane/EtOAc 9/1 to 4:1); $[\alpha]_D^{23}$=−2.8 (c1, CHCl$_3$);
HPLC: purity 97% ee; column: Chiralpak AS-H (150×4.6 mm), hexane/i-PrOH 97/3, 1.00 ml/min, t$_R$=5.0 min (S)-enantiomer and 6.7 min (R)-enantiomer.

Methyl (R)-(−)-(2-isopropoxyphenyl)phenylphosphinite borane complex (compound 3i)
Yield: 81%, colorless oil (CC with cyclohexane/EtOAc 19/1)
$[\alpha]_D^{23}$=−44.6 (c1.0, CHCl$_3$);
HPLC: purity 97% ee; column: Chiralcel OJ-H (150×4.6 mm), hexane/i-PrOH 99.75/0.25, 1.25 ml/min, t$_R$=10.6 min (S)-enantiomer and 15.5 min (R)-enantiomer.

Methyl (R)-(−)-(2-isopropylphenyl)phenylphosphinite borane complex (compound 3j)
Yield: 59%, white solid; m.p.=86° C. (CC with cyclohexane/EtOAc 19/1);
$[\alpha]_D^{22}$=−11.3 (c1.0, CHCl$_3$);
HPLC: purity 98% ee; column: Chiralcel OJ-H (150×4.6 mm), hexane/i-PrOH 99.75/0.25, 1.25 ml/min, t$_R$=5.4 min (S)-enantiomer and 7.3 min (R)-enantiomer.

Methyl (R)-(−)-(2-ethoxyphenyl)phenylphosphinite borane complex (compound 3k)
Yield: 76%, white solid; m.p.=54-55° C. (CC with cyclohexane/EtOAc 19/1 to 9/1);
$[\alpha]_D^{23}$=−44.2 (c1.0, CHCl$_3$);
HPLC: purity >98% ee; column: Chiralcel OD-H (150× 4.6 mm), hexane/i-PrOH 99.75/0.25, 1.25 ml/min, t$_R$=8.7 min (R)-enantiomer and 10.4 min (S)-enantiomer, Methyl (R)-(−)-(3-methoxyphenyl)phenylphosphinite borane complex (compound 3l)
Yield: 76%, colorless syrup (CC with cyclohexane/EtOAc 19/1);
$[\alpha]_D^{23}$=−3.2 (c1.0, CHCl$_3$);
HPLC: purity >98% ee; column: Chiralpak AS-H (150× 4.6 mm), hexane/i-PrOH 99.75/0.25, 1.20 ml/min, t$_R$=7.7 min (S)-enantiomer and 11.1 min (R)-enantiomer.

Methyl (R)-(+)-(3-isopropoxyphenyl)phenylphosphinite borane complex (compound 3m)
Yield: 85%, colorless oil (CC with cyclohexane/EtOAc 9/1)
$[\alpha]_D^{23}$=+1.6 (c1.0, CHCl$_3$);
HPLC: purity 99% ee; column: Chiralcel OD-H (150×4.6 mm), hexane, 1.25 ml/min,
t$_R$=12.2 min (S)-enantiomer and 13.2 min (R)-enantiomer.

Methyl (R)-(−)-(dibenzo[b,d]furan-4-yl)phenylphosphinite borane complex (compound 3n)
Yield: 78%; colorless syrup (CC with cyclohexane/EtOAc 49/1);
$[\alpha]_D^{23}$=−121.7 (c1.0, CHCl$_3$);
HPLC: purity 98% ee; column: Reprosil 100 (150×4.6 mm), hexane/i-PrOH 99.5/0.5, 1.25 ml/min, t$_R$=9.3 min (R)-enantiomer and 10.6 min (S)-enantiomer.

Methyl (R)-(−)-(2-ethylphenyl)phenylphosphinite borane complex (compound 3o)
Yield: 52%, colorless syrup (CC with cyclohexane/EtOAc 19/1);
$[\alpha]_D^{23}$=−5.1 (c1.0, CHCl$_3$);
HPLC: purity >99% ee; column: Chiralcel OJ-H (150×4.6 mm), hexane/i-PrOH 99/1, 1.00 ml/min, t$_R$=8.2 min (R)-enantiomer and 10.5 min (S)-enantiomer.

Methyl (R)-(−)-(3-isopropylphenyl)phenylphosphinite borane complex (compound 3p)
Yield: 84%, colorless syrup (CC with cyclohexane EtOAc 19/1);
$[\alpha]_D^2$=−2.1 (c1.0, CHCl$_3$);
HPLC: purity >99% ee; column: Chiralcel OJ-H (150×4.6 mm), hexane/i-PrOH 98/2, 1.00 ml/min, t$_R$=6.3 min (S)-enantiomer and 11.5 min (R)-enantiomer.

Methyl (R)-(−)-(3-methylphenyl)phenylphosphinite borane complex (compound 3q)
Yield: 80%, colorless syrup (CC with cyclohexane/EtOAc 19/1);
$[\alpha]_D^{23}$=−1.5 (c1.0, CHCl$_3$);
HPLC: purity >98% ee; column: Chiralcel OJ-H (150×4.6 mm), hexane/i-PrOH 99/1, 1.10 ml/min, t$_R$=15.6 min (R)-enantiomer and 18.0 min (S)-enantiomer.

Methyl (R)-(−)-(3-ethylphenyl)phenylphosphinite borane complex (compound 3r)
Yield: 84%, colorless syrup (CC with cyclohexane/EtOAc 19/1);
$[\alpha]_D^{23}$=−0.4 (c1.0, CHCl$_3$);

HPLC: purity >98% ee; column: Chiralcel OJ-H (150×4.6 mm), hexane/i-PrOH 99/1, 1.00 ml/min, $t_R$=12.7 min (S)-enantiomer and 16.0 min (R)-enantiomer.

Methyl (R)-(−)-(3-ethoxyphenyl)phenylphosphinite borane complex (compound 3s)

Yield: 83%, colorless syrup (CC with cyclohexane/EtOAc 9/1);

$[\alpha]_D^{23}$=−1.7 (c1.0, CHCl$_3$);

HPLC: purity >98% ee; column: Chiralpak AS-H (150×4.6 mm), hexane/i-PrOH 99.75/0.25, 1.00 ml/min, $t_R$=6.7 min (S)-enantiomer and 7.4 min (R)-enantiomer.

Methyl (R)-(+)-(4-(rac-2-methylbutyl)-phenyl)phenylphosphinite borane complex (compound 3t)

Yield: 80%, colorless oil (CC with cyclohexane/EtOAc 9/1);

$[\alpha]_D^{25}$=+11.9 (c1.0, CHCl$_3$);

HPLC: purity >98% ee; column: Chiralcel OJ-H (150×4.6 mm), hexane/i-PrOH 99.75/0.25, 1.00 ml/min, $t_R$=9.4 min (rac, $S_P$)-enantiomer and 10.9 min (rac, $R_P$)-enantiomer.

Methyl (R)-(+)-(4-ethoxyphenyl)-phenylphosphinite borane complex (compound 3u)

Yield: 79%, colorless syrup (CC with cyclohexane/EtOAc 49/1);

$[\alpha]_D^{23}$=+40.5 (c1.0, CHCl$_3$);

HPLC: purity >99% ee; column: Reprosil 100 (150×4.6 mm), hexane/i-PrOH 99.75/0.25, 1.25 ml/min, $t_R$=8.4 min (R)-enantiomer and 8.9 min (S)-enantiomer.

I.2 Preparation of Chiral Phosphine Ligands of the Formula (I)

Example 4

General Procedure for Synthesizing Compounds of the Formula I with (1S,1'S)-(9,9-dimethyl-9H-xanthene-4,5-diyl)bis((aryl)(phenyl)phosphine) ligands (compounds I-A);

(1S,1'S)-(2,7-di-tert-butyl-9,9-dimethyl-9H-xanthene-4,5-diyl)bis((aryl)(phenyl)-phosphine) ligands (compounds I-B); and (1S,1'S)-(oxybis(2,1-phenylene))bis((aryl)(phenyl)phosphine) ligands (compound I-C).

Compounds I-A (Compounds of the formula I in which $A^1$=O; $A^2$ and $A^3$ together are C(CH$_3$)$_2$ and $R^1$, $R^2$, $R^3$, $R^4$, $R^5$ and $R^6$ are in each case H)

A solution of 1.5 mmol of 9,9-dimethylxanthene (315 mg) and 3.3 mmol of TMEDA (383 mg) in 10 ml of absolute diethyl ether was admixed at room temperature under an argon atmosphere with 3.3 mol of n-butyllithium (2.06 ml of a 1.6 M solution) over the course of 10 minutes and stirred for a further 24 hours. In a further Schlenk vessel, 6.6 mmol of DABCO (739 mg) were added to in each case 3.3 mmol of the borane complex compounds from example 3 In 10 ml of absolute hexane, and the solution was stirred at 40° C. under an argon atmosphere for 20 hours. During this time, the BH$_3$*DABCO complex separated out as a solid and, for further use of the solution, was filtered off therefrom.

The dilithium salt solution formed above was cooled to −45° C. and slowly admixed with the hexane solution of the now-unprotected chiral methyl phosphinite by means of cannula. For completion, the reaction solution was allowed to warm to room temperature and after-stirred overnight. For work-up, the volume of the solution was concentrated to approx. ⅓ a in vacuo and then slowly admixed with anaerobic water (10 ml). The solution was extracted with dichloromethane (2×20 ml) and the combined organic phases were washed again with water (5 ml). After drying with Na$_2$SO$_4$, the solvent was removed in vacuo and the target compound was obtained by column chromatography or crystallization.

Compounds I-B (Compounds of the formula I, in which $A^1$=O; $A^2$ and $A^3$ together are C(CH$_3$)$_2$ and $R^1$, $R^3$, $R^4$ and $R^6$ are in each case H; and $R^2$ and $R^5$ are in each case C(CH$_3$)$_3$)

Compounds of the formula I-B were obtained according to the process for preparing compounds I-A, only 4,5-dibromo-2,7-di-tert-butyl-9,9-dimethylxanthene (1.5 mmol, 720 mg) was admixed with 3.3 mmol of n-butyllithium solution in absolute THF (10 ml) at −70° C. to give the dilithium salt. Over the course of three hours, the mixture was allowed to warm to 0° C.

Compounds I-C

Compounds of the formula I-C were obtained according to the process for preparing compounds I-A, only 1.5 mmol (255 mg) of diphenyl ether were used instead of 1.5 mmol of 9,9-dimethylxanthene.

The following compounds were obtained according to the general procedure:

(1S,1'S)-(+)-(9,9-Dimethyl-9H-xanthene-4,5-diyl)bis((2-methoxy-phenyl)(phenyl)phosphine) (compound I-A.a)

Yield: 60%; white precipitate, m.p.=199-200° C. (from CH$_2$Cl$_2$/hexane);

$[\alpha]_D^{22}$=+14.1 (c1.0, CHCl$_3$);

$^1$H-NMR (CDCl$_3$): δ 7.40 (2H, dd, J 7.7, 1.6 Hz, arom. H), 7.25 (2H, m, arom. H), 7.22-7.08 (10H, m, arom. H), 6.95 (2H, t, J 7.6 Hz, arom. H), 6.82 (2H, m, arom. H), 6.71 (2H, dt, J 7.4, 1.0 Hz, arom. H), 6.58-6.46 (4H, m, arom. H), 3.70 (6H, s, 2×OCH$_3$), 1.66 (6H, s, 2×CH$_3$);

$^{13}$C-NMR (CDCl$_3$): δ 161.2 (m, 2×C—OMe), 152.9 (m, 2×C—O), 137.1 (m, 2×C—P), 133.8 (m, 4×CH), 133.4 (2×CH), 132.2 (2×CH), 129.9 (2×C—C), 129.6 (2×CH), 127.8 (2×CH), 127.7 (m, 4×CH), 126.3 (m, 2×C—P), 125.8 (2×CH), 125.6 (m, 2×C—P), 123.1 (2×CH), 120.7 (2×CH), 110.2 (2×CH), 55.5 (2×OCH$_3$), 34.4 (C), 31.5 (2×CH$_3$);

$^{31}$P-NMR (CDCl$_3$): δ −26.6;

MS (EI, 70 eV) m/z: 638 (100, [M]$^+$), 561 (10, [M-Ph]$^+$);

HRMS (ESI) [M+H]$^+$: m/z calc.: for C$_4$H$_{37}$O$_3$P$_2$ 639.22124, found: 639.22143, [M+Na]$^+$:

m/z calc.: for C$_{41}$H$_{36}$NaO$_3$P$_2$ 661.20319, found: 661.20277.

(1S,1'S)(+(9,9-Dimethyl-9H-xanthene-4,5-diyl)bis((2-methylphenyl)(phenyl)phosphine) (compound I-A.b)

Yield: 54%; white precipitate, m.p.=196-98° C. (from CH$_2$Cl$_2$/hexane);

$[\alpha]_D^{23}$=+7.1 (c1.0, CHCl$_3$);

$^1$H-NMR (CDCl$_3$): δ 7.41 (2H, dd, J 7.8, 1.4 Hz, arom. H), 7.27-7.08 (14H, m, arom. H), 6.99 (2H, dt, J 7.6, 1.6 Hz, arom. H), 6.95 (2H, t, J 7.6 Hz, arom. H), 6.69 (2H, m, arom. H), 6.50 (2H, m, arom. H), 2.31 (6H, s, 2×CH$_3$), 1.66 (6H, s, 2×CH$_3$);

$^{13}$C-NMR (CDCl$_3$): δ 152.7 (m, 2×C—O), 142.3 (m, 2×C—C), 136.5 (m, 2×C—P), 136.4 (m, 2×C—P), 134.2 (m, 4×CH), 132.5 (2×CH), 132.1 (2×CH), 129.9 (2×C—C), 129.8 (m, 2×CH), 128.2 (m, 2×CH), 128.1 (m, 2×CH), 128.1 (m, 4×CH), 126.2 (2×CH), 125.7 (2×CH), 125.1 (m, 2×C—P), 123.3 (2×CH), 34.5 (m, C), 31.7 (2×CH$_3$), 21.3 (m, 2×CH$_3$);

$^{31}$P-NMR (CDCl$_3$): δ −24.5;

MS (EI, 70 eV) m/z: 606 (100, [M]$^+$), 591 (7, [M-CH$_3$]$^+$), 529 (9, [M-Ph]$^+$), 408 (20, [M-PPh(2-Me-Ph)+H]$^+$), 393 (28, [C$_{27}$H$_{22}$OP]$^+$);

HRMS (EI) [M]$^+$: m/z calc.: for C$_{41}$H$_{36}$OP$_2$ 606.22226, found: 606.22359.

(1S,1'S)-(−)-(9,9-Dimethyl-9H-xanthene-4,5-diyl)bis((4-methoxy-phenyl)(phenyl)phosphine) compound I-A.c)

Yield: 53%; white precipitate, m.p.=156-158° C. (from CH$_2$Cl$_2$/hexane);

[α]$_D^{23}$=−47.7 (c1.0, CHCl$_3$);

$^1$H-NMR (CDCl$_3$): δ 7.42 (2H, dd, J 7.8, 1.5 Hz, arom. H), 7.29-7.13 (14H, m, arom. H), 6.98 (2H, t, J 7.6 Hz, arom. H), 6.78 (4H, m, arom. H), 6.59 (2H, m, arom. H), 3.80 (6H, s, 2×OCH$_3$), 1.67 (6H, s, 2×CH$_3$);

$^{13}$C-NMR (CDCl$_3$): δ 159.8 (2×C—OMe), 152.4 (m, 2×C—O), 138.2 (m, 2×C—P), 135.6 (m, 4×CH), 133.4 (m, 4×CH), 131.9 (2×CH), 129.8 (2×C—C), 128.0 (m, 4×CH), 127.8 (2×CH), 127.7 (m, 2×C—P), 126.3 (m, 2×C—P), 126.1 (2×CH), 123.2 (2×CH), 113.8 (m, 4×CH), 55.0 (2×OCH$_3$), 34.4 (C), 31.7 (2×CH$_3$);

$^{31}$P-NMR (CDCl$_3$): δ −18.8;

MS (EI, 70 eV) m/z; 638 (100, [M]$^+$), 623 (53, [M-CH$_3$]$^+$), 608 (9, [M−2×CH$_3$]$^+$), 561 (5, [M-Ph]$^+$), 319 (52, [C$_{20}$H$_{16}$O$_2$P]$^+$);

HRMS (EI) [M]$^+$: m/z calc.: for C$_{41}$H$_{36}$O$_3$P$_2$ 638.21342, found: 638.21503.

(1S,1'S-(−)-(9,9-Dimethyl-9H-xanthene-4,5-diyl)bis((4-methylphenyl)(phenyl)phosphine) (compound I-A.d)

Yield: 33%; white precipitate, m.p.=83-85° C. (from CC with cyclohexane/EtOAc 49/1);

[α]$_D^{23}$=−23.6 (c1.0, CHCl$_3$);

$^1$H-NMR (CDCl$_3$): δ 7.38 (2H, dd, J 7.8, 1.6 Hz, arom. H), 7.26-7.11 (10H, m, arom. H), 7.10-6.97 (8H, m, arom. H), 6.95 (2H, t, J 7.7 Hz, arom. H), 6.54 (2H, m, arom. H), 2.30 (6H, s, 2×CH$_3$), 1.64 (6H, s, 2×CH$_3$);

$^{13}$C-NMR (CDCl$_3$): δ 152.6 (m, 2×C—O), 138.0 (2×C—C), 137.7 (m, 2×C—P), 134.0 (m, 4×CH), 133.7 (m, 4×CH), 133.7 (m, 2×C—P), 132.0 (2×CH), 129.9 (2×C—C), 129.0 (m, 4×CH), 128.0 (m, 4×CH), 127.8 (2×CH), 126.2 (2×CH), 126.0 (m, 2×C—P), 123.3 (2×CH), 34.5 (C), 31.8 (2×CH$_3$), 21.3 (2×CH$_3$);

$^{31}$P-NMR (CDCl$_3$): δ −18.2;

MS (EI, 70 eV) m/z: 606 (82, [M]$^+$), 591 (12, [M-CH$_3$]$^+$), 529 (2, [M-Ph]$^+$), 408 (43, [M-PPh (2-Me-Ph)+H]$^+$), 393 (100, [C$_{27}$H$_{22}$PP]$^+$);

HRMS (ESI) [M+H]$^+$: m/z calc.: for C$_{41}$H$_{37}$OP$_2$ 607.23142, found: 607.23146.

(1S,1'S)-(−)-(9,9-Dimethyl-9H-xanthene-4,5-diyl)bis((1-naphthyl)(phenyl)phosphine) (compound I-A.e)

Yield: 56%; white precipitate, m.p.=200-202° C. (from CH$_2$Cl$_2$/hexane);

[α]$_D^{21}$=−62.6 (c1.0, CHCl$_3$);

$^1$H-NMR (CDCl$_3$): δ 8.25 (2H, br d, J 8.4 Hz, arom. H), 7.85 (2H, br d, J 8.1 Hz, arom. H), 7.77 (2H, br d, J 8.4 Hz, arom. H), 7.47 (2H, m, arom. H), 7.43 (2H, dd, J 7.8, 1.4 Hz, arom. H), 7.38 (2H, m, arom. H), 7.25 (2H, dd, J 7.9, 7.4 Hz, arom. H), 7.21-7.15 (2H, m, arom. H), 7.11-7.04 (8H, m, arom. H), 6.91 (2H, t, J 7.7 Hz, arom. H), 6.87 (2H, m, arom. H), 6.46 (2H, m, arom. H), 1.69 (6H, s, 2×CH$_3$);

$^{13}$C-NMR (CDCl$_3$): δ 152.7 (m, 2×C—O), 136.3 (m, 2×C—P), 135.6 (m, 2×C—C), 135.1 (m, 2×C—P), 134.2 (m, 4×CH), 133.4 (m, 2×C—C), 132.6 (2×CH), 131.6 (2×CH), 130.0 (2×C—C), 128.9 (2×CH), 128.3 (2×CH), 128.2 (2×CH), 128.0 (m, 4×CH), 126.9 (m, 2×CH), 126.3 (2×CH), 125.8 (2×CH), 125.6 (2×CH), 125.4 (2×CH), 125.1 (m, 2×C—P), 123.4 (2×CH), 34.5 (C), 31.6 (2×CH$_3$);

$^{31}$P-NMR (CDCl$_3$): δ −25.3;

MS (EI, 70 eV) m/z; 678 (100, [M]$^+$), 663 (10, [M-CH$_3$]$^+$), 601 (2, [M-Ph]$^+$), 444 (37, [M-PPh(Naphthyl)+H]$^+$), 429 (32, [M-PPh(Naphthyl)-CH$_3$+H]$^+$);

HRMS (EI) [M]$^+$: m/z calc.: for C$_{47}$H$_{36}$OP$_2$ 678.22359, found: 678.22548.

(1S,1'S)-(−)-(9,9-Dimethyl-9H-xanthene-4,5-diyl)bis(2-naphthyl)(phenyl)phosphine) (Compound I-A.f)

Yield: 63%; white precipitate, m.p.=238-239° C. (CC with cyclohexane/EtOAc 19/1 to 4/1);

[α]$_D^{22}$=−135.0 (c1.0, CHCl$_3$);

$^1$H-NMR (CDCl$_3$): δ 7.78 (2H, m, arom. H), 7.70-7.60 (6H, m, arom. H), 7.51-7.38 (6H, m, arom. H), 7.30-7.21 (4H, m, arom. H), 7.15-7.07 (4H, m, arom. H), 7.06-7.00 (4H, m, arom. H), 6.96 (2H, t, J 7.7 Hz, arom. H), 6.56 (2H, m, arom. H), 1.71 (6H, s, 2×CH$_3$);

$^{13}$C-NMR (CDCl$_3$): δ 158.1 (m, 2×C—O), 156.0 (m, 2×C—O), 152.9 (m, 2×C—O), 135.2 (m, 2×C—P), 133.5 (m, 4×CH), 132.1 (2×CH), 131.3 (2×CH), 130.2 (2×C—C), 128.2 (2×CH), 127.7 (m, 4×CH), 126.9 (2×CH), 126.3 (2×CH), 124.3 (2×C—C), 124.0 (m, 2×C—P), 123.5 (2×CH), 123.3 (2×C—C), 122.7 (2×CH), 122.4 (2×CH), 121.0 (m, 2×C—P), 120.8 (2×CH), 120.4 (2×CH), 112.2 (2×CH), 34.6 (C), 31.5 (2×CH$_3$);

$^{31}$P-NMR (CDCl$_3$): δ −16.4;

MS (EI, 70 eV) m/z: 678 (100, [M]$^+$), 663 (12, [M-CH$_3$]$^+$), 601 (2, [M-Ph]$^+$);

HRMS (ESI) [M+H]$^+$: m/z calc.: for C$_{47}$H$_{37}$OP$_2$ 679.23142, found: 679.23216, [M+Na]$^+$:

m/z calc.: for C$_{47}$H$_{36}$NaOP$_2$ 701.21336, found: 701.21253.

(1S,1'S)-(−)-(9,9-Dimethyl-9H-xanthene-4,5-diyl)bis((9-phenanthryl)(phenyl)phosphine) (Compound I-A.g)

Yield: 44%; white precipitate, m.p.=185-188° C. (from CH$_2$Cl$_2$/hexane);

[α]$_D^{24}$=−89.2 (c1.0, CHCl$_3$);

$^1$H-NMR (CDCl$_3$): δ 8.69 (2H, br d, J 8.2 Hz, arom. H), 8.64 (2H, br d, J 8.4 Hz, arom. H), 8.29 (2H, m, arom. H), 7.65-7.58 (4H, m, arom. H), 7.48-7.42 (8H, m, arom. H), 7.09 (2H, m, arom. H), 7.02-6.95 (6H, m, arom. H), 6.94-6.88 (6H, m, arom. H), 6.51 (2H, m, arom. H), 1.74 (6H, s, 2×CH$_3$);

$^{13}$C-NMR (CDCl$_3$): δ 152.9 (m, 2×C—O), 135.6 (m, 2×C—P), 134.1 (m, 4×CH), 133.7 (m, 2×C—C), 133.5 (m, 4×C—C), 133.1 (2×CH), 132.7 (2×CH), 131.6 (2×C—C), 130.8 (4×C—C), 130.2 (2×C—C), 130.1 (2×C—C), 128.7 (2×CH), 128.2 (2×CH), 127.9 (m, 4×CH), 127.7 (2×CH), 126.7 (2×CH), 126.4 (2×CH), 126.3 (2CH), 126.2 (2×CH), 124.8 (m, 2×C—P), 123.6 (2×CH), 122.6 (2×CH), 122.4 (2×CH), 34.7 (C), 31.4 (2×CH$_3$);

$^{31}$P-NMR (CDCl$_3$): δ −23.0;

MS (EI, 70 eV) m/z; 778 (100, [M]$^+$), 701 (2, [M-Ph]$^+$), 453 (81, C$_{32}$H$_{22}$OP$^+$), 178 (31, C$_{14}$H$_{10}$]$^+$);

HRMS (ESI) [M+H]$^+$: m/z calc.: for C$_{55}$H$_{41}$OP$_2$ 779.26272, found: 779.26263, [M+Na]$^+$:

m/z calc.: for C$_{55}$H$_{40}$NaOP$_2$ 801.24466, found: 801.24431.

(1S,1'S)-(−)-(9,9-Dimethyl-9H-xanthene-4,5-diyl)bis((3,5-dimethoxy-phenyl)(phenyl)phosphine) (compound I-A.h)

Yield: 48%; white solid; m.p.=80-82° C. (CC with cyclohexane/EtOAc 19/1);

[α]$_D^{23}$=−6.9 (c1.0, CHCl$_3$);

$^1$H-NMR (CDCl$_3$): δ 7.39 (2H, dd, J 7.9, 1.5 Hz, arom. H), 7.28-7.16 (10H, m, arom. H), 6.95 (2H, t, J 7.7 Hz, arom. H), 6.60 (2H, m, arom. H), 6.38-6.30 (6H, m, arom. H), 3.62 (12H, s, 4×OCH$_3$), 1.63 (6H, s, 2×CH$_3$);

$^{13}$C-NMR (CDCl$_3$): δ 160.2 (m, 2×C—OMe), 152.5 (m, 2×C—O), 139.7 (m, 2×C—P), 136.8 (m, 2×C—P), 133.7 (m, 4×CH), 131.9 (2×CH), 129.8 (2×C—C), 128.2 (2×CH), 127.9 (m, 4×CH), 126.2 (2×CH), 125.3 (m, 2×C—P), 123.3 (2×CH), 111.2 (m, 4×CH), 100.7 (2×CH), 54.9 (4×OCH$_3$), 34.3 (m), 31.5 (2×CH$_3$);

$^{31}$P-NMR (CDCl$_3$): δ −14.9;

MS (EI, 70 eV) m/z: 698 (100, [M]$^+$), 683 (9, [M-CH$_3$]$^+$), 621 (3, [M-Ph]$^+$);

HRMS (ESI) [M+H]⁺: m/z calc.: for $C_{43}H_{41}OP_2$ 699.24237, found: 699.24282, [M+Na]⁺:
m/z calc.: for $C_{43}H_{40}NaO_5P_2$ 721.22432, found: 721.22351.

(1S,1'S)-(+)-(9,9-Dimethyl-9H-xanthene-4,5-diyl)bis((2-isopropoxyphenyl)(phenyl) phosphine) (compound I-A.i)
Yield: 52%; white solid; m.p.=73-75° C. (from CC with cyclohexane/EtOAc 49/1);
$[\alpha]_D^{24}$=+24.9 (c1.0, CHCl₃);
¹H-NMR (CDCl₃): δ −7.37 (2H, dd, J 7.7, 1.6 Hz, arom. H), 7.32-7.25 (4H, m, arom. H), 7.21-7.12 (8H, m, arom. H), 6.92 (2H, t, J 7.6 Hz, arom. H), 6.75 (2H, m, arom. H), 6.70-6.58 (6H, m, atom. H), 4.42 (2H, sept, J 6.0 Hz, CHO), 1.63 (6H, s, 2×CH₃), 1.04 (3H, t, J 6.0 Hz, CH₃), 0.96 (3H, t, J 6.0 Hz, CH₃);
¹³C-NMR (CDCl₃): δ 159.2 (m, 2×C—OEt), 152.9 (m, 2×C—O), 137.3 (m, 2×C—P), 136.7 (m, 2×C—P), 134.3 (m, 4×CH), 133.7 (m, 2×CH), 132.4 (2×CH), 129.7 (2×C—C), 129.2 (2×CH), 127.8 (2×CH), 127.7 (m, 4×CH), 125.7 (2×CH), 125.7 (m, 2×C—P), 122.9 (2×CH), 120.2 (2×CH), 112.0 (2×CH), 69.9 (2×OCH), 34.5 (C), 31.6 (2×CH₃), 21.8 (2×CH₃), 21.5 (2×CH₃);
³¹P-NMR (CDCl₃): δ −25.6;
MS (EI, 70 eV) m/z: 694 (100, [M]⁺), 635 (5, [M-OC₃H₇]⁺), 617 (6, [M-Ph]⁺), 451 (2, [M-PPh(2-iPrO-Ph)]⁺);
HRMS (EI) [M]⁺: m/z calc.: for $C_{45}H_{44}O_3P_2$ 694.27602, found: 694.27565.

(1S,1'S)-(−)-(9,9-Dimethyl-9H-xanthene-4,5-diyl)bis((2-ethoxyphenyl)(phenyl) phosphine) (compound I-A.k)
Yield: 85%; white solid; m.p.=78-80° C. (from CC with cyclohexane/EtOAc 49/1);
$[\alpha]_D^{21}$=−22.5 (c1.0, CHCl₃);
¹H-NMR (CDCl₃): δ 7.38 (2H, dd, J 7.7, 1.6 Hz, arom. H), 7.26-7.10 (12H, m, arom. H), 6.93 (2H, t, J 7.6 Hz, arom. H), 6.76 (2H, m, arom. H), 6.69 (2H, dt, J 7.5, 1.0 Hz, arom. H), 6.62 (2H, m, atom. H), 6.56 (2H, m, arom. H), 3.89 (4H, m, CH₂O), 1.64 (6H, s, 2×CH₃), 1.00 (6H, t, J 6.9 Hz, 2×CH₃);
¹³C-NMR (CDCl₃): δ 160.4 (m, 2×C—OEt), 152.9 (m, 2×C—O), 137.2 (m, 2×C—P), 134.1 (m, 4×CH), 133.3 (m, 2×CH), 132.3 (2×CH), 129.8 (2×C—C), 129.3 (2×CH), 127.9 (2×CH), 127.7 (m, 4×CH), 126.9 (m, 2×C—P), 125.8 (2×CH), 125.7 (m, 2×C—P), 123.0 (2×CH), 120.6 (2×CH), 111.2 (2×CH), 63.8 (2×OCH₂), 34.5 (C), 31.7 (2×CH₃), 14.4 (CH₃);
³¹P-NMR (CDCl₃): δ −25.7;
MS (EI, 70 eV) m/z: 666 (100, [M]⁺), 637 (3, [M-C₂H₅]⁺), 589 (13, [M-Ph]⁺);
HRMS (ESI) [M+H]⁺: m/z calc.: for $C_{43}H_{41}O_3P_2$ 667.25254, found: 667.25303.

(1S,1'S)-(−)-(9,9-Dimethyl-9H-xanthene-4,5-diyl)bis((3-methoxyphenyl)(phenyl) phosphine) (compound I-A.l)
Yield: 12%; white solid; m.p.=135° C. (from ethanol);
$[\alpha]_D^{21}$=−6.3 (c1.0, CHCl₃);
¹H-NMR (CDCl₃): δ 7.40 (2H, dd, J 7.8, 1.5 Hz, arom. H), 7.26-7.16 (10H, m, arom. H), 7.12 (2H, m, arom. H), 6.95 (2H, t, J 7.6 Hz), 6.79-6.69 (6H, m, arom. H), 6.55 (2H, m, arom. H), 3.65 (6H, s, 2×OCH₃), 1.64 (6H, s, 2×CH₃);
¹³C-NMR (CDCl₃): δ 159.1 (m, 2×C—OMe), 152.6 (m, 2×C—O), 138.9 (m, 2×C—P), 137.1 (m, 2×C—P), 133.9 (m, 4×CH), 132.1 (2×CH), 129.9 (2×C—C), 129.0 (m, 2×CH), 128.2 (2×CH), 128.1 (m, 4×CH), 126.3 (2×CH), 126.2 (m, 2×CH), 125.6 (m, 2×C—P), 123.4 (2×CH), 118.8 (m, 2×CH), 114.2 (2×CH), 55.0 (2×OCH₃), 34.4 (C), 31.8 (2×CH₃);
³¹P-NMR (CDCl₃): δ −16.5;

MS (EI, 70 eV) m/z: 638 (100, [M]⁺), 637 (11, [M–H]⁺), 623 (19, [M-CH₃]+), 607 (4, [M-OCH₃]⁺), 561 (3, [M-Ph]⁺), 531 (4,[M-(3-MeO-Ph]⁺);
HRMS (ESI) [M+H]⁺: m/z calc.: for $C_{41}H_{37}O_3P_2$ 639.22124, found: 639.22145.

(1S,1'S)-(−)-(9,9-Dimethyl-9H-xanthene-4,5-diyl)bis((3-isopropoxyphenyl)(phenyl) phosphine) (compound I-A.m)
Yield: 76%; white solid; m.p.=63-65° C. (from CC with cyclohexane/EtOAc 99/1);
$[\alpha]_D^{23}$=−13.6 (c1.0, CHCl₃);
¹H-NMR (CDCl₃): δ 7.39 (2H, dd, J 7.8, 1.6 Hz, arom. H), 7.24-7.17 (10H, m, arom. H), 7.10 (2H, m, arom. H), 6.95 (2H, t, J 7.7 Hz, arom. H), 6.76 (2H, ddd, J 8.3, 2.3, 1.0 Hz, arom. H), 6.75-6.67 (4H, m, arom. H), 6.56 (2H, m, arom. H), 4.33 (2H, sept, J 6.0 Hz, 2×OCH), 1.63 (6H, s, 2×CH₃), 1.20 (6H, d, J 6.0 Hz, 2×CH₃), 1.19 (6H, d, J 6.0 Hz, 2×CH₃);
¹³C-NMR (CDCl₃): δ 157.5 (m, 2×C—OⁱPr), 152.5 (m, 2×C—O), 138.7 (m, 2×C—P), 137.2 (m, 2×C—P), 134.0 (m, 4×CH), 132.1 (2×CH), 129.9 (2×C—C), 129.1 (m, 2×CH), 128.2 (2×CH), 128.0 (m, 4×CH), 126.3 (2×CH), 126.1 (m, 2×CH), 125.8 (m, 2×C—P), 123.3 (2×CH), 120.4 (m, 2×C—H), 116.5 (2×CH), 69.6 (2×OCH), 34.4 (C), 31.8 (2×CH₃), 22.0 (2×CH₃), 21.9 (2×CH₃);
³¹P-NMR (CDCl₃): δ −16.5;
MS (EI, 70 eV) m/z: 694 (100, [M]⁺), 679 (21, [M-CH₃]⁺), 651 (9, [M-C₃H₇]⁺);
HRMS (EI) [M]⁺: m/z calc.: for $C_{45}H_{44}O_3P_2$ 694.27602, found: 694.27403.

(1S,1'S-(−)-(9,9-Dimethyl-9H-xanthene-4,5-diyl)bis((dibenzo[b,d]-furan-4-yl)(phenyl)phosphine) (compound I-A.n)
Yield: 63%; white solid; m.p.=172-174° C. (CC with cyclohexane/EtOAc 49/1);
$[\alpha]_D^{23}$=−92.5 (c1.0, CHCl₃);
¹H-NMR (CDCl₃): δ 7.93 (2H, ddd, J 7.2, 1.5, 0.7 Hz, arom. H), 7.80 (2H, dd, J 7.6, 1.3 Hz, arom. H), 7.50-7.28 (8H, m, arom. H), 7.12-6.83 (14H, m, arom. H), 6.68 (2H, m, arom. H), 6.51 (2H, m, arom. H), 1.69 (6H, s, 2×CH₃);
¹³C-NMR (CDCl₃): δ 158.1 (m, 2×C—O), 156.0 (m, 2×C—O), 152.9 (m, 2×C—O), 135.2 (m, 2×C—P), 133.5 (m, 4×CH), 132.1 (2×CH), 131.3 (2×CH), 130.2 (2×C—C), 128.2 (2×CH), 127.7 (m, 4×CH), 126.9 (2×CH), 126.3 (2×CH), 124.3 (2×C—C), 124.0 (m, 2×C—P), 123.5 (2×CH), 123.3 (2×C—C), 122.7 (2×CH), 122.4 (2×CH), 121.0 (m, 2×C—P), 120.8 (2×CH), 120.4 (2×CH), 112.2 (2×CH), 34.6 (C), 31.5 (2×CH₃);
³¹P-NMR (CDCl₃): δ −28.9
MS (EI, 70 eV) m/z: 758 (100, [M]⁺), 743 (18, [M-CH₃]⁺), 681 (2, [M-Ph]⁺), 469 (18, [M-PPh(4-DBF)-CH₃+H]⁺);
HRMS (ESI) [M+H]⁺: m/z calc.: for $C_{51}H_{37}O_3P_2$ 759.22124, found: 759.22137, [M+Na]⁺: m/z calc.: for $C_{51}H_{36}NaO_3P_2$ 781.20319, found: 781.20276.

(1S,1'S)-(+)-(9,9-Dimethyl-9H-xanthene-4,5-diyl)bis((2-ethylphenyl)(phenyl)phosphine) (compound I-A.o)
Yield: 10%; colorless crystals, m.p.=72-75° C. (from CH₂Cl₂/hexane);
$[\alpha]_D^{24}$=+53.9 (c1.0, CHCl₃);
¹H-NMR (CDCl₃): δ 7.38 (2H, dd, J 7.7, 1.6 Hz, arom. H), 7.26-7.12 (14H, m, arom. H), 6.96 (2H, m, arom. H), 6.92 (2H, t, J 7.6 Hz, arom. H), 6.71 (2H, m, arom. H), 6.48 (2H, m, arom. H), 2.86-2.64 (4H, m, CH₂), 1.63 (6H, s, 2×CH₃), 1.06 (6H, t, J 7.5 Hz, 2×CH₃);
¹³C-NMR (CDCl₃): δ 152.4 (m, 2×C—O), 148.6 (m, 2×C-Et), 137.3 (m, 2×C—P), 135.9 (m, 2×C—P), 134.1 (m, 4×CH), 133.4 (2×CH), 132.2 (2×CH), 129.8 (2×C—C), 128.5 (2×CH), 128.0 (m, 4×CH), 127.7 (2×CH), 126.2 (2×C—H), 125.7 (2×CH), 125.7 (m, 2×C—P), 123.2 (2×CH), 34.4 (m, C), 31.8 (2×CH$_3$), 27.1 (m, 2×CH$_2$), 15.1 (2×CH$_3$);

$^{31}$P-NMR (CDCl$_3$): δ −26.5;

MS (EI, 70 eV) m/z: 634 (100, [M]$^+$), 633 (29, [M–H), 557 (21, [M-Ph]$^+$), 529 (21, [M-(2-Et-Ph)]$^+$);

HRMS (EI) [M]$^+$: m/z calc.: for C$_{43}$H$_{40}$OP$_2$ 634.25489, found: 634.25319.

(1S,1'S)-(+)-(9,9-Dimethyl-9H-xanthene-4,5-diyl)bis((3-methylphenyl)(phenyl)phosphine) (compound I-A.q)

Yield: 33%; white solid; m.p.=147-148° C. (from CH$_2$Cl$_2$/hexane);

[α]$_D^{25}$=+6.5 (c1.0, CHCl$_3$);

$^1$H-NMR (CDCl$_3$): δ 7.39 (2H, dd, J 7.7, 1.6 Hz, arom. H), 7.25-7.13 (10H, m, arom. H), 7.12-6.99 (6H, m, arom. H), 6.95 (2H, t, J 7.7 Hz, arom. H), 6.92 (2H, m, arom. H), 6.55 (2H, m, arom. H), 2.22 (6H, s, 2×CH$_3$), 1.64 (6H, s, 2×CH$_3$);

$^{13}$C-NMR (CDCl$_3$): δ 152.6 (m, 2×C—O), 137.5 (m, 2×C—P), 137.4 (m, 2×C-Me), 137.1 (m, 2×C—P), 134.6 (m, 2×CH), 133.3 (m, 4×CH), 132.1 (2×CH), 130.8 (m, 2×CH), 129.9 (2×C—C), 129.0 (2×CH), 128.0 (2×CH), 128.0 (2×CH), 128.0 (m, 4×CH), 126.1 (2×CH), 125.9 (m, 2×C—P), 123.3 (2×CH), 34.4 (C), 31.6 (2×CH$_3$), 21.4 (2×CH$_3$);

$^{31}$P-NMR (CDCl$_3$): δ −17.4;

MS (EI, 70 eV) m/z: 606 (100, [M]$^+$), 591 (15, [M-CH]$^+$);

HRMS (ESI) [M+H]$^+$: m/z calc.: for C$_{41}$H$_{37}$OP$_2$ 607.23142, found: 607.23170, [M+Na]$^+$:

m/z calc.: for C$_{41}$H$_{36}$NaOP$_2$ 629.21336, found: 629.21306.

(1S,1'S)-(−)-(9,9-Dimethyl-9H-xanthene-4,5-diyl)bis((3-ethoxyphenyl)(phenyl)-phosphine) (compound I-A.s)

Yield: 45%; white solid; m.p.=67-69° C. (from CC with cyclohexane/EtOAc 99/1); [α]$_D^{24}$=−6.0 (c1.0, CHCl$_3$);

$^1$H-NMR (CDCl$_3$): δ 7.39 (2H, dd, J 7.8, 1.5 Hz, arom. H), 7.24-7.15 (10H, m, arom. H), 7.10 (2H, m, arom. H), 6.94 (2H, t, J 7.7 Hz), 6.75 (2H, ddd, J 8.1, 2.5, 1.0 Hz, arom. H), 6.74-6.69 (4H, m, arom. H), 6.55 (2H, m, arom. H), 3.85 (4H, m, 2×OCH$_2$), 1.63 (6H, s, 2×CH$_3$), 1.30 (6H, t, J 7.0 Hz, 2×CH$_3$);

$^{13}$C-NMR (CDCl$_3$): δ 158.5 (m, 2×C—OEt), 152.6 (m, 2×C—O), 138.8 (m, 2×C—P), 137.2 (m, 2×C—P), 133.9 (m, 4×CH), 132.1 (2×CH), 129.9 (2×C—C), 129.0 (m, 2×CH), 128.2 (2×CH), 128.1 (m, 4×CH), 126.3 (2×CH), 126.1 (m, 2×CH), 125.7 (m, 2×C—P), 123.4 (2×CH), 119.2 (m, 2×CH), 114.9 (2×CH), 63.1 (2×OCH$_2$), 34.4 (C), 31.8 (2×CH$_3$), 14.8 (2×CH$_3$);

$^{31}$P-NMR (CDCl$_3$): δ −16.5;

MS (EI, 70 eV) m/z: 666 (100, [M]$^+$), 651 (19, [M-CH$_3$]$^+$), 621 (3,[M-OC$_2$H$_5$]$^+$), 589 (2, [M-Ph]$^+$);

HRMS (EI) [M]$^+$: m/z calc.: for C$_{43}$H$_{40}$O$_3$P$_2$ 666.24472, found: 666.24399.

(1S,1'S)-(−)-(9,9-Dimethyl-9H-xanthene-4,5-diyl)bis((4-(rac-2-methylbutyl)phenyl)-(phenyl)-phosphine) (compound I-A.t)

Yield: 60%; white precipitate, m.p.=151-154° C. (from CH$_2$Cl$_2$/hexane);

[α]$_D^{23}$=−26.0 (c1.0, CHCl$_3$);

$^1$H-NMR (CDCl$_3$): δ 7.39 (2H, dd, J 7.7, 1.5 Hz, arom. H), 7.26-7.16 (10H, m, arom. H), 7.12-7.04 (4H, m, arom. H), 7.03-6.98 (4H, m, arom. H), 6.94 (2H, t, J 7.6 Hz, arom. H), 6.55 (2H, m, arom. H), 2.61 (2H, dd, J 13.4, 6.2 Hz, 2×H$_A$—CH$_2$Ph), 2.32 (2H, dd, J 113.4, 8.1 Hz, 2×H$_B$—CH$_2$Ph), 1.64 (2H, m, 2×CH), 1.64 (6H, s, C(CH$_3$)$_2$), 1.40 (2H, m, 2×H$_A$—CH$_2$), 1.17 (2H, m, 2×H$_B$—CH$_2$), 0.91 (6H, t, J 7.4 Hz, CH$_3$), 0.84 (6H, d, J 6.7 Hz, CH$_3$), $^{13}$C-NMR (CDCl$_3$): δ 152.6 (m, 2×C—O), 141.8 (2×C—C), 137.8 (m, 2×C—P), 133.9 (m, 4×CH), 133.9 (m, 2×C—P), 133.8 (m, 4×CH), 132.0 (2×CH), 129.8 (2×C—C), 129.1 (m, 4×CH), 128.0 (m, 4×CH), 127.9 (2×CH), 126.3 (m, 2×C—P), 126.2 (2×CH), 123.2 (2×CH), 43.1 (CH$_2$Ph), 36.5 (CH), 34.4 (C), 31.9 (CH$_3$), 31.9 (CH$_3$), 29.3 (CH$_2$), 19.0 (CH$_3$), 11.5 (CH$_3$);

$^{31}$P-NMR (CDCl$_3$): δ −18.5;

MS (EI, 70 eV) m/z: 718 (100, [M]$^+$), 703 (17, [M-CH$_3$]$^+$), 662 (18), 359 (39);

HRMS (EI) [M]$^+$: m/z calc.: for CH$_{49}$H$_{32}$OP$_2$ 718.34879, found: 718.34779.

(1S,1'S)-(−)-(9,9-Dimethyl-9H-xanthene-4,5-diyl)bis((4-ethoxyphenyl)(phenyl)-(phosphine) (compound I-A.u)

Yield 72%; white solid; m.p.=175-177° C. (from CH$_2$/Cl$_2$/hexane);

[α]$_D^{22}$=−46.5 (c1.0, CHCl$_3$);

$^1$H-NMR (CDCl$_3$): δ 7.38 (2H, dd, J 7.7, 1.5 Hz, arom. H), 7.24-7.07 (14H, m, arom. H), 6.94 (2H, t, J 7.6 Hz, arom. H), 6.73 (4H, m, arom. H), 6.55 (2H, m, arom. H), 3.99 (4H, q, J 7.0 Hz 2×OCH$_2$), 1.63 (6H, s, 2×CH$_3$), 1.40 (6H, t, J 7.0 Hz, 2×CH$_3$);

$^{13}$C-NMR (CDCl$_3$): δ 159.3 (2×C—OEt), 152.5 (m, 2×C—O), 138.3 (m, 2×C—P), 135.7 (m, 4×CH), 133.5 (m, 4×CH), 131.9 (2×CH), 129.9 (2×C—C), 128.0 (m, 4×CH), 127.8 (2×CH), 127.6 (m, 2×C—P), 126.4 (m, 2×C—P), 126.1 (2×CH), 123.2 (2×CH), 114.4 (m, 4×CH), 63.1 (2×OCH$_2$), 34.4 (C), 31.8 (2×CH$_3$), 14.9 (2×CH$_3$);

$^{31}$P-NMR (CDCl$_3$): δ −18.8;

MS (EI, 70 eV) m/z; 666 (100, [M]$^+$), 651 (5, [M-CH$_3$]$^+$), 637 (5, [M-C$_2$H$_5$]$^+$), 621 (7, [M-OC$_2$H$_5$]$^+$), 562 (29);

HRMS (EI) [M]$^+$: m/z calc.: for C$_{43}$H$_{40}$O$_3$P$_2$ 666.24472, found: 666.24449.

(1S,1'S)-(+)-(2,7-Di-tert-butyl-9,9-dimethyl-9H-xanthene-4,5-diyl)bis((2-methoxy-phenyl)(phenyl)phosphine) (compound I-B.a)

Yield: 80%; white solid; m.p.=116-118° C. (from ethanol);

[α]$_D^{20}$=+28.5 (c1.0, CHCl$_3$);

$^1$H-NMR (CDCl$_3$): δ·7.33 (2H, d, J 2.4 Hz, arom. H), 7.25-7.08 (12H, m, arom. H), 6.78 (2H, m, arom. H), 6.68 (2H, dt, J 7.4, 1.0 Hz, arom. H), 6.53-6.45 (4H, m, arom. H), 3.67 (6H, s, 2×OCH$_3$), 1.64 (6H, s, 2×CH$_3$), 1.08 (18H, s, 6×CH$_3$);

$^{13}$C-NMR (CDCl$_3$): δ 161.2 (d, J 7.7 Hz, 2×C—OMe), 151.0 (m, 2×C—O), 144.9 (2×C—C), 137.4 (m, 2×C—P), 133.8 (m, 4×CH), 133.4 (2×CH), 129.5 (4×CH), 129.0 (2×C—C), 127.7 (2×CH), 127.6 (m, 4×CH), 126.6 (m, 2×C—P), 124.3 (m, 2×C—P), 122.2 (2×CH), 120.6 (2×CH), 109.9 (2×CH), 55.4 (2×OCH$_3$), 34.9 (C), 34.4 (2×C), 31.3 (2×CH$_3$), 31.3 (6×CH$_3$);

$^{31}$P-NMR (CDCl$_3$): δ −25.1;

MS (EI, 70 eV) m/z: 750 (100, [M]$^+$), 735 (5, [M-CH$_3$]$^+$), 673 (15, [M-Ph]$^+$), 521 (15 [M-CH$_3$—PPh(2-MeO-Ph)+H]$^+$);

HRMS (EI) [M]$^+$: m/z calc.: for C$_{49}$H$_{52}$O$_3$P$_2$ 750.33755, found: 750.33862.

(1S,1'S)-(+)-(2,7-Di-tert-butyl-9,9-dimethyl-9H-xanthene-4,5-diyl)bis((2-methyl-phenyl)(phenyl)phosphine) (compound I-B.b)

Yield: 80%; white solid; m.p.=91-93° C. (CC with cyclohexane/EtOAc 49/1);

[α]$_D^{23}$=+7.9 (c1.0, CHCl$_3$);

$^1$H-NMR (CDCl$_3$): δ 7.37 (2H, br d, J 2.4 Hz, arom. H), 7.25-7.07 (14H, m, arom. H), 6.97 (2H, dt, J 7.4, 1.7 Hz, arom. H), 6.70 (2H, m, arom. H), 6.47 (2H, m, arom. H), 2.28 (6H, s, 2×CH$_3$), 1.66 (6H, s, 2×CH$_3$), 1.08 (18H, s, 6×CH$_3$);

$^{13}$C-NMR (CDCl$_3$): δ 150.7 (m, 2×C—O), 145.3 (2×C—C), 142.2 (m, 2×C-Me), 136.8 (m, 2×C—P), 136.6 (m, 2×C—P), 134.1 (m, 4×CH), 132.6 (2×CH), 129.8 (m, 2×CH), 129.6 (2×CH), 128.9 (2×C—C), 128.2 (2×CH), 128.2 (2×CH), 128.0 (m, 4×CH), 125.6 (2×CH), 123.8 (m, 2×C—P), 122.7 (2×CH), 34.9 (m, C), 34.4 (2×C), 32.0 (2×CH$_3$), 31.3 (6×CH$_3$), 21.3 (m, 2×CH$_3$);

$^{31}$P-NMR (CDCl$_3$): δ −22.7;

MS (EI, 70 eV) m/z: 718 (100, [M]$^+$), 703 (10, [M-CH$_3$]$^+$), 641 (4, [M-Ph]$^+$), 505 (13, [M-CH$_3$—PPh(2-Me-Ph)+H]$^+$);

HRMS (ESI) [M+H]$^+$: m/z calc.: for C$_{49}$H$_{53}$OP$_2$ 719.35662, found: 719.35675.

(1S,1'S)-(−)-(2,7-Di-tert-butyl-9,9-dimethyl-9H-xanthene-4,5-diyl)bis((4-methoxy-phenyl)(phenyl)phosphine) (compound I-B.c)

Yield: 52%; white solid; m.p.=160-164° C. (CC with heptane/EtOAc 49/1);

[α]$_D^{21}$=−38.7 (c1.0, CHCl$_3$);

$^1$H-NMR (CDCl$_3$): δ 7.42 (2H, br d, J 2.3 Hz, arom. H), 7.23-7.11 (14H, m, arom. H), 6.76 (4H, m, arom. H), 6.54 (2H, m, arom. H), 3.78 (6H, s, 2×OCH$_3$), 1.66 (6H, s, 2×CH$_3$), 1.10 (18H, s, 6×CH$_3$);

$^{13}$C-NMR (CDCl$_3$): δ 159.8 (2×C—OMe), 150.4 (m, 2×C—O), 145.1 (2×C—C), 138.5 (m, 2×C—P), 135.6 (m, 4×CH), 133.5 (m, 4×CH), 129.2 (2×CH), 128.8 (2×C—C), 128.2 (m, 2×C—P), 127.9 (m, 4×CH), 127.7 (2×CH), 125.1 (m, 2×C—P), 122.7 (2×CH), 113.7 (m, 4×CH), 55.1 (2×OCH$_3$), 34.8 (m, C), 34.4 (2×C), 32.1 (2×CH$_3$), 31.3 (6×CH$_3$);

$^{31}$P-NMR (CDCl$_3$): δ −17.5;

MS (EI, 70 eV) m/z; 750 (100, [M]$^+$), 735 (16, [M-CH$_3$]$^+$), 536 (30, [M-PPh(4-MeO-Ph)+H]$^+$), 521 (30, [M-CH$_3$—PPh(MeO-Ph)+H]$^+$);

HRMS (EI) [M]$^+$: m/z calc.: for C$_{49}$H$_{52}$O$_3$P$_2$ 750.33862, found: 750.34064.

(1S,1'S)-(−)-(2,7-Di-tertbutyl-9,9-dimethyl-9H-xanthene-4,5-diyl)bis((4-methyl-phenyl)(phenyl)phosphine) (compound I-B.d)

Yield: 78%; white solid; m.p.=80-82° C. (CC with cyclohexane/EtOAc 49/1);

[α]$_D^{24}$=−29.3 (c1.0, CHCl$_3$);

$^1$H-NMR (CDCl$_3$): δ 7.36 (2H, br d, J 2.4 Hz, arom. H), 7.25-7.15 (10H, m, arom. H), 7.13-7.06 (4H, m, arom. H), 6.98 (4H, m, arom. H), 6.57 (2H, m, arom. H), 2.31 (6H, s, 2×CH$_3$), 1.65 (6H, s, 2×CH$_3$), 1.10 (18H, s, 6×CH$_3$);

$^{13}$C-NMR (CDCl$_3$): δ 150.5 (m, 2×C—O), 145.1 (2×C—C), 138.2 (2×C—P), 137.8 (m, 2×C—C), 134.0 (m, 4×CH), 133.9 (2×C—P), 133.7 (m, 4×CH), 129.3 (2×CH), 128.8 (2×C—C), 128.8 (m, 4×C—H), 127.9 (m, 4×CH), 127.7 (2×CH), 124.9 (m, 2×C—P), 122.7 (2×CH), 34.8 (C), 34.4 (2×C), 32.1 (2×CH$_3$), 31.3 (6×CH$_3$), 21.3 (2×CH$_3$); $^{31}$P-NMR (CDCl$_3$): δ −16.8;

MS (EI, 70 eV) m/z; 718 (100, [M]$^+$), 703 (26, [M-CH$_3$]$^+$), 520 (21, [M-PPh(4-Me-Ph)+H]$^+$);

HRMS (ESI) [M+H]$^+$: m/z calc.: for C$_{49}$H$_{53}$OP$_2$ 719.35662, found: 719.35662, [M+Na]$^+$:

m/z calc.: for C$_{49}$H$_{52}$NaOP$_2$ 741.33856, found: 741.33748.

(1S,1'S)-(−)-(2,7-Di-ter-butyl-9,9-dimethyl-9H-xanthene-4,5-diyl)bis((1-naphthyl)(phenyl)phosphine) (compound I-B.e)

Yield: 66%; white solid; m.p.=110-112° C. (CC with cyclohexane/EtOAc 49/1);

[α]$_2$=−19.2 (c1.0, CHCl$_3$);

$^1$H-NMR (CDCl$_3$): δ 8.20 (2H, m, arom. H), 7.82 (2H, m, arom. H), 7.74 (2H, m, arom. H), 7.43 (2H, ddd, J 8.3. 7.0, 1.4 Hz, arom. H), 7.38 (2H, m, arom. H), 7.32 (2H, ddd, J 8.4. 6.8, 1.4 Hz, arom. H), 7.22 (2H, m, arom. H), 7.16-6.99 (10H, m, arom. H), 6.86 (2H, m, arom. H), 6.39 (2H, m, arom. H), 1.69 (6H, s, 2×CH$_3$), 0.99 (18H, s, 6×CH$_3$);

$^{13}$C-NMR (CDCl$_3$): δ 150.8 (m, 2×C—O), 145.3 (2×C—C), 136.3 (m, 2×C—P), 135.6 (m, 2×C—P), 135.2 (m, 2×C—C), 134.1 (m, 4×CH), 133.3 (m, 2×C—C), 131.4 (2×CH), 130.0 (2×CH), 129.1 (2×C—C), 128.8 (2×CH), 128.2 (2×CH), 128.1 (2×CH), 127.8 (m, 4×CH), 127.0 (m, 2×CH), 125.7 (2×CH), 125.5 (2×CH), 125.3 (2×CH), 123.7 (m, 2×C—P), 122.7 (2×CH), 35.0 (m, C), 34.4 (2×C), 31.7 (2×CH$_3$), 31.2 (6×CH$_3$);

$^{31}$P-NMR (CDCl$_3$): δ −23.6;

MS (EI, 70 eV) m/z; 790 (100, [M]$^+$), 775 (15, [M-CH$_3$]$^+$), 664 (5, [M-C$_{10}$H$_7$+H]), 556 (3, [M-PPh (I-naphthyl)+H]$^+$);

HRMS (ESI) [M+H]$^+$: m/z calc.: for C$_{55}$H$_{53}$OP$_2$ 791.35662, found: 791.35706.

(1S,1'S)-(−)-(2,7-Di-tert-butyl-9,9-dimethyl-9H-xanthene-4,5-diyl)bis((2-naphthyl)(phenyl)phosphine) (compound I-B.f)

Yield: 63%; white solid; m.p.=152-153° C. (from CH$_2$Cl$_2$/hexane);

[α]$_D^{21}$=−101.8 (c1.0, CHCl$_3$);

$^1$H-NMR (CDCl$_3$): δ 7.80 (2H, m, arom. H), 7.73-7.62 (6H, m, arom. H), 7.51-7.39 (6H, m, arom. H), 7.34-7.24 (2H, m, arom. H), 7.18-7.08 (4H, m, arom. H), 7.07-6.98 (6H, m, arom. H), 6.61 (2H, m, arom. H), 1.75 (6H, s, 2×CH$_3$), 1.10 (18H, s, 6×CH$_3$);

$^{13}$C-NMR (CDCl$_3$): δ 150.8 (m, 2×C—O), 145.4 (2×C—C), 137.3 (m, 2×C—P), 135.2 (m, 2×C—C), 133.9 (m, 2×CH), 133.8 (m, 4×CH), 133.2 (m, 2×C—P), 133.2 (2×C—C), 130.4 (m, 2×CH), 129.3 (2×CH), 129.1 (2×C—C), 128.1 (2×CH), 128.0 (2×CH), 127.9 (m, 2×CH), 127.6 (2×CH), 127.2 (m, 4×CH), 126.0 (2×CH), 125.7 (2×CH), 124.3 (m, 2×C—P), 122.8 (2×CH), 34.9 (C), 34.5 (C), 31.8 (2×CH$_3$), 31.3 (6×CH$_3$);

$^{31}$P-NMR (CDCl$_3$): δ −15.1;

MS (EI, 70 eV) m/z; 790 (100, [M]$^+$), 775 (15, [M-CH$_3$]$^+$), 664 (3, [m-C$_{10}$H$_7$+H]);

HRMS (ESI) [M+H]$^+$: m/z calc.: for C$_{55}$H$_{53}$OP$_2$ 791.35662, found: 791.35657, [M+Na]$^+$:

m/z calc.: for C$_{55}$H$_{52}$NaOP$_2$ 813.33856, found: 813.33800.

(1S,1'S)-(−)-(2,7-Di-tert-butyl-9,9-dimethyl-9H-xanthene-4,5-diyl)bis((9-phenanthryl)(phenyl)phosphine) (compound I-B.g)

Yield: 86%; white precipitate, m.p.=170-173° C. (from CH$_2$Cl$_2$/hexane);

[α]$_D^{22}$=−22.3 (c1.0, CHCl$_3$);

$^1$H-NMR (CDCl$_3$): δ 8.71-8.61 (4H, m, Hz, arom. H), 8.24 (2H, m, arom. H), 7.64-7.56 (4H, m, arom. H), 7.47-7.38 (8H, m, arom. H), 7.08 (2H, m, arom. H), 6.98-6.78 (10H, m, arom. H), 6.46 (2H, m, arom. H), 1.74 (6H, s, 2×CH$_3$) 0.99 (18H, s, 6×CH$_3$);

$^{13}$C-NMR (CDCl$_3$): δ 151.1 (m, 2×C—O), 145.5 (C—C), 135.9 (m, 2×C—P), 134.0 (m, 4×CH), 133.7 (m, 2×C—C), 133.7 (m, 2×C—C), 132.8 (2×CH), 131.6 (2×C—C), 130.8 (2×C—C), 130.1 (2×CH), 130.0 (m, 2×C—P), 129.5 (2×C—C), 128.7 (2×CH), 128.0 (2×CH), 128.0 (m, 2×CH), 127.7 (m, 4×CH), 126.6 (2×CH), 126.3 (2×CH), 126.1 (2×CH), 126.0 (2×CH), 123.5 (m, 2×C—P), 122.5 (2×CH), 122.5 (2×CH), 122.4 (2×CH), 35.1 (m, C), 34.4 (2×C), 31.3 (2×CH$_3$), 31.2 (6×CH$_3$);

$^{31}$P-NMR (CDCl$_3$): δ −21.0;

MS (EI, 70 eV) m/z; 890 (100, [M]$^+$), 875 (22, [M-CH$_3$]$^+$), 445 (37), 178 (31, C$_{14}$H$_{10}$]$^+$);

HRMS (ESI) [M+H]$^+$: m/z calc.: for C$_{63}$H$_{57}$OP$_2$ 891.38792, found: 891.38840, [M+Na]$^+$: m/z calc.: for C$_{63}$H$_{56}$NaOP$_2$ 913.36986, found: 913.38767.

(1S,1'S)-(-)-(2,7-Di-tert-butyl-9,9-dimethyl-9H-xanthene-4,5-diyl)bis((3,5-dimethoxy-phenyl)(phenyl)phosphine) (compound I-B.h)

Yield: 48%; white solid; m.p.=78-80° C. (from CH$_2$Cl$_2$/hexane);

$[\alpha]_D^{21}$=-5.7 (c1.0, CHCl$_3$);

$^1$H-NMR (CDCl$_3$): δ 7.37 (2H, d, J 2.5 Hz, arom. H), 7.25-7.16 (10H, m, arom. H), 6.56 (2H, m, arom. H), 6.39-6.34 (4H, m, arom. H), 6.31 (2H, m, arom. H), 3.64 (12H, s, 4×OCH$_3$), 1.66 (6H, s, 2×CH$_3$), 1.11 (18H, s, 6×CH$_3$);

$^{13}$C-NMR (CDCl$_3$): δ 160.2 (m, 4×C—Ome), 150.6 (m, 2×C—O), 145.3 (2×C—C), 140.1 (m, 2×C—P), 137.2 (m, 2×C—P), 133.9 (m, 4×CH), 129.3 (2×CH), 129.0 (2×C—C), 128.2 (2×CH), 127.9 (m, 4×CH), 124.2 (m, 2×C—P), 122.9 (2×CH), 111.3 (m, 4×CH), 100.9 (2×CH), 55.1 (4×OCH$_3$), 34.8 (M, C), 34.4 (2×C), 31.9 (2×CH$_3$), 31.3 (6×CH$_3$);

$^{31}$P-NMR (CDCl$_3$): δ -13.7;

MS (EI, 70 eV) m/z; 810 (100, [M]$^+$), 795 (43, [M-CH$_3$]$^+$), 779 (11, [M-OCH$_3$]$^+$), 733 (5, [M-Ph]$^+$, 566 (5, [M-PPh (3,5-MeO-Ph)+H]$^+$);

HRMS (EI) [M]$^+$: m/z calc.: for C$_{51}$H$_{56}$O$_5$P$_2$ 810.35975, found: 810.35888.

(1S,1'S)-(+)-(2,7-Di-tert-butyl-9,9-dimethyl-9H-xanthene-4,5-diyl)bis((2-isopropoxy-phenyl)(phenyl)phosphine) (compound I-B.i)

Yield: 69%; white solid; m.p.=80-82° C. (with CC cyclohexane/EtOAc 49/1);

$[\alpha]_D^{25}$=+17.5 (c1.0, CHCl$_3$);

$^1$H-NMR (CDCl$_3$): δ 7.34 (2H, d, J 2.4 Hz, arom. H), 7.30-7.21 (4H, m, arom. H), 7.18-7.10 (8H, m, arom. H), 6.72 (2H, m, arom. H), 6.67-6.54 (6H, m, arom. H), 4.39 (2H, sept, J 6.1 Hz, 2×OCH), 1.65 (6H, s, 2×CH$_3$), 1.09 (18H, s, 6×CH$_3$), 1.01 (6H, d, J 6.1 Hz, 2×CH$_3$), 0.96 (6H, d, J 6.1 Hz, 2×CH$_3$);

$^{13}$C-NMR (CDCl$_3$): δ 159.2 (m, 2×C—OiPr), 150.9 (m, 2×C—O), 144.6 (2×C—C), 137.8 (m, 2×C—P), 134.2 (m, 4×CH), 133.7 (m, 2×CH), 129.7 (2×CH), 129.1 (2×CH), 128.7 (2×C—C), 127.9 (m, 2×C—P), 127.7 (2×CH), 127.5 (m, 4×CH), 124.6 (m, 2×C—P), 122.4 (2×CH), 120.1 (2×CH), 111.6 (2×CH), 69.9 (2×OCH), 34.8 (m, C), 34.4 (2×C), 32.0 (2×CH$_3$), 31.3 (6×CH$_3$), 22.0 (2×CH$_3$), 21.6 (2×CH$_3$);

$^{31}$P-NMR (CDCl$_3$): δ -24.7;

MS (EI, 70 eV) m/z; 806 (100, [M]$^+$), 763 (5, [M-C$_3$H]$^+$), 729 (12, [M-Ph]$^+$),

HRMS (ESI) [M+H]$^+$: m/z calc.: for C$_{53}$H$_{61}$O$_3$P$_2$ 807.40905, found: 807.40956, [M+Na]$^+$:

m/z calc.: for C$_{53}$H$_{60}$NaO$_3$P$_2$ 829.39099, found: 829.39036.

(1S,1'S)-(+(+)-2,7-Di-tert-butyl-9,9-dimethyl-9H-xanthene-4,5-diyl)bis((2-isopropyl-phenyl)(phenyl)phosphine) (compound I-B.j)

Yield: 47%; white solid; m.p.=157-159° C. (with EtOH);

$[\alpha]_D^{22}$=+40.2 (c1.0, CHCl$_3$);

$^1$H-NMR (CDCl$_3$): δ 7.34 (2H, d, J 2.4 Hz, arom. H), 7.31-7.14 (14H, m, arom. H), 6.94 (2H, m, arom. H), 6.45 (2H, m, arom. H), 3.65 (2H, m, 2×CH), 1.66 (6H, s, 2×CH$_3$), 1.10 (6H, d, J 6.6 Hz, 2×CH$_3$), 1.08 (18H, s, 6×CH$_3$), 1.06 (6H, d, J 6.1 Hz, 2×CH$_3$);

$^{13}$C-NMR (CDCl$_3$): δ 153.4 (m, 2×C—O), 150.1 (m, 2×C—C), 145.0 (2×C—C), 137.9 (m, 2×C—P), 135.4 (m, 2×C—P), 134.2 (m, 4×CH), 133.6 (2×CH), 129.6 (2×CH), 128.7 (2×CH), 128.5 (2×C—C), 127.8 (m, 4×CH), 127.8 (2×CH), 125.6 (2×CH), 125.0 (m, 2×CH), 124.7 (m, 2×C—P), 122.8 (2×CH), 34.8 (m, C), 34.4 (2×C), 32.3 (2×CH$_3$), 31.3 (6×CH$_3$), 30.8 (m, 2×CH), 24.4 (2×CH$_3$), 23.7 (2×CH$_3$);

$^{31}$P-NMR (CDCl$_3$): δ -25.9;

MS (EI, 70 eV) m/z; 774 (26, [M]$^+$), 697 (9, [M-Ph]$^+$), 655 (11, [M-(2-iPr-Ph)]$^+$), 548 (69, [M-(PPh(2-iPr-Ph)+H]$^+$), 533 (100, [M-(PPh(2-iPr-Ph)-CH$_3$+H]$^+$);

HRMS (ESI) [M+H]$^+$: m/z calc.: for C$_{53}$H$_{61}$OP$_2$ 775.41922, found: 775.41890, [M+Na]$^+$:

m/z calc.: for C$_{53}$H$_{60}$NaOP$_2$ 797.40116, found: 797.40179.

(1S,1'S)-(-)-(2,7-Di-tert-butyl-9,9-dimethyl-9H-xanthene-4,5-diyl)bis((2-ethoxy-phenyl)(phenyl)phosphine) (compound I-B.k)

Yield: 63%; white solid; m.p.=78-80° C. (CC with cyclohexane/EtOAc 49/1);

$[\alpha]_D^{24}$=-2.2 (c1.0, CHCl$_3$);

$^1$H-NMR (CDCl$_3$): δ 7.36 (2H, d, J 2.4 Hz, arom. H), 7.26-7.09 (12H, m, arom. H), 6.76 (2H, m, arom. H), 6.68 (2H, dt, J 7.3, 1.0 Hz, arom. H), 6.64-6.54 (4H, m, arom. H), 3.88 (4H, m, 2×OCH$_2$), 1.66 (6H, s, 2×CH$_3$), 1.09 (18H, s, 6×CH$_3$), 0.98 (6H, t, J 7.1 Hz, 2×CH$_3$);

$^{13}$C-NMR (CDCl$_3$): δ 160.4 (m, 2×C—OEt), 150.8 (m, 2×C—O), 145.0 (2×C—C), 136.8 (m, 2×C—P), 134.0 (m, 4×CH), 133.4 (m, 2×CH), 129.6 (2×CH), 129.6 (2×CH), 128.9 (2×C—C), 128.0 (2×CH), 127.7 (m, 4×CH), 126.3 (m, 2×C—P), 123.7 (m, 2×C—P), 122.7 (2×CH), 120.6 (2×CH), 111.0 (2×CH), 63.8 (2×OCH$_2$), 34.9 (m, C), 34.4 (2×C), 32.0 (2×CH$_3$), 31.3 (6×CH$_3$), 14.4 (2×CH$_3$);

$^{31}$P-NMR (CDCl$_3$): δ -23.8;

MS (EI, 70 eV) m/z; 778 (100, [M]$^+$), 701 (35, [M-Ph]$^+$), 673 (20, [M-Ph-C$_2$H$_4$]$^+$), 535 (16, [M-CH$_3$—PPh(2-EtO-Ph)+H]$^+$);

HRMS (ESI) [M+H]$^+$: m/z calc.: for C$_{51}$H$_{57}$O$_3$P$_2$ 779.37775, found: 779.37897, [M+Na]$^+$: calc.: for C$_{51}$H$_{56}$NaO$_3$P$_2$ 801.35969, found: 801.35636.

(1S,1'S)-(-)-(2,7-Di-tert-butyl-9,9-dimethyl-9H-xanthene-4,5-diyl)bis((3-methoxyphenyl) (phenyl)phosphine) (compound I-B.l)

Yield: 47%; white solid; m.p.=84-85° C. (CC with cyclohexane/EtOAc 49/1);

$[\alpha]_D^{23}$=-7.3 (c1.0, CHCl$_3$);

$^1$H-NMR (CDCl$_3$): δ 7.36 (2H, d, J 2.3 Hz, arom. H), 7.24-7.08 (12H, m, arom. H), 6.79-6.71 (6H, m, arom. H), 6.53 (2H, m, arom. H), 3.64 (6H, m, 2×OCH$_3$), 1.65 (6H, s, 2×CH$_3$), 1.08 (18H, s, 6×CH$_3$);

$^{13}$C-NMR (CDCl$_3$): δ 159.1 (m, 2×C—OMe), 150.5 (m, 2×C—O), 145.3 (2×C—C), 139.2 (m, 2×C—P), 137.5 (m, 2×C—P), 133.9 (m, 4×CH), 129.3 (2×CH), 128.9 (2×C—C), 128.9 (m, 2×CH), 128.1 (2×CH), 128.0 (m, 4×CH), 126.3 (m, 2×CH), 124.4 (m, 2×C—P), 122.9 (2×CH), 118.6 (m, 2×C—H), 114.3 (2×CH), 55.0 (2×OCH$_3$), 34.8 (m, C), 34.5 (2×C), 32.0 (2×CH$_3$), 31.3 (6×CH$_3$);

$^{31}$P-NMR (CDCl$_3$): δ -15.2;

MS (EI, 70 eV) nm/z 750 (44, [M]$^+$), 735 (9, [M-CH$_3$]$^+$), 643 (1, [M-(3-MeO-Ph)]$^+$);

HRMS (EI) [M]$^+$: m/z calc.: for C$_{49}$H$_{52}$O$_3$P$_2$ 750.33862, found: 750.33735.

(1S,1'S)-(-)-(2,7-Di-tert-butyl-9,9-dimethyl-9H-xanthene-4,5-diyl)bis((3-isopropoxy-phenyl)(phenyl)phosphine) (compound I-B.m)

Yield: 69% white solid; m.p.=74-75° C. (CC with cyclohexane/EtOAc 99/1);

$[\alpha]_D^{23}$=−8.5 (c1.0, CHCl$_3$);

$^1$H-NMR (CDCl$_3$): δ 7.35 (2H, d, J 2.3 Hz, arom. H), 7.24-7.15 (10H, m, arom. H), 7.10 (2H, m, arom. H), 6.80-6.68 (6H, m, arom. H), 6.54 (2H, m, arom. H), 4.32 (2H, sept, J 6.0 Hz, 2×OCH), 1.64 (6H, s, 2×CH$_3$), 1.19 (6H, d, J 6.0 Hz, 2×CH$_3$), 1.18 (6H, d, J 6.0 Hz, 2×CH$_3$), 1.09 (18H, s, 6×CH$_3$);

$^{13}$C-NMR (CDCl$_3$): δ 157.5 (m, 2×C—OiPr), 150.5 (m, 2×C—O), 145.2 (2×C—C), 138.8 (m, 2×C—P), 137.4 (m, 2×C—P), 133.9 (m, 4×CH), 129.3 (2×CH), 129.0 (m, 2×CH), 128.9 (2×C—C), 128.2 (2×CH), 127.9 (m, 4×CH), 126.2 (m, 2×CH), 124.5 (m, 2×C—P), 122.9 (2×CH), 120.4 (m, 2×C—H), 116.7 (2×CH), 69.7 (2×OCH), 34.8 (m, C), 34.5 (2×C), 32.0 (2×CH$_3$), 31.3 (6×CH$_3$), 22.0 (2×CH$_3$), 22.0 (2×CH$_3$);

$^{31}$P-NMR (CDCl$_3$): 5-15.3;

MS (EI, 70 eV) m/z: 806 (90, [M]$^+$), 791 (10, [M-CH$_3$]$^+$), 564 (89, [M-(3-iPrO-Ph)+H]$^+$), 549 (100, [M-(3-iPrO-Ph)-CH$_3$+H]$^+$);

HRMS (ESI) [M+H]$^+$: m/z calc.: for C$_{53}$H$_{61}$O$_3$P$_2$ 807.40905, found: 807.40894, [M+Na]$^+$: m/z calc.: for C$_{53}$H$_{60}$NaO$_3$P$_2$ 829.39099, found: 829.39147.

(1S,1'S)-(−)-(2,7-Di-tert-butyl-9,9-dimethyl-9H-xanthene-4,5-diyl)bis((dibenzo[b,d]-furan-4-yl)(phenyl)phosphine) (compound I-B.n)

Yield: 49% white solid; m.p.=115-118° C. (CC with cyclohexane/EtOAc 99/1 to 19/1);

$[\alpha]_D^{22}$=−55.5 (c1.0, CHCl$_3$);

$^1$H-NMR (CDCl$_3$): δ 7.92 (2H, m, arom. H), 7.81 (2H, dd, J 7.5, 1.1 Hz, arom. H), 7.46-7.28 (8H, m, arom. H), 7.13-6.97 (8H, m, arom. H), 6.89 (4H, m, arom. H), 6.76 (2H, m, arom. H), 6.53 (2H, m, arom. H), 1.70 (6H, s, 2×CH$_3$),1.01 (18H, s, 6×CH$_3$);

$^{13}$C-NMR (CDCl$_3$): δ 158.1 (m, 2×C—O), 156.0 (2×C—O), 151.0 (m, 2×C—O), 145.4 (2×C—C) 135.6 (m, 2×C—P), 133.5 (m, 4×CH), 131.5 (m, 2×CH), 129.4 (2×CH), 129.2 (2×C—C), 128.1 (2×CH), 127.6 (m, 4×CH), 126.7 (2×CH), 124.2 (2×C—C), 123.3 (2×C—C), 122.8 (2×CH), 122.7 (m, 2×C—P), 122.6 (2×CH), 122.3 (2×CH), 121.3 (m, 2×C—P), 120.7 (2×CH), 120.4 (2×CH), 112.0 (2×CH), 35.0 (m, C), 34.4 (2×C) 31.6 (2×CH$_3$), 31.1 (6×CH$_3$);

$^{31}$P-NMR (CDCl$_3$): δ −27.3

MS (EI, 70 eV) m/z: 870 (100, [M]$^+$), 855 (34, [M-CH$_3$]$^+$), 581 (23, [M-PPh(4-DBF)-CH$_3$+H]$^+$), 168 (15, [DBF]$^+$;

HRMS (ESI) [M+H]$^+$: m/z calc.: for C$_{59}$H$_{53}$O$_3$P$_2$ 871.34644, found: 871.34658, [M+Na]$^+$:

m/z calc.: for C$_{59}$H$_{52}$NaO$_3$P$_2$ 893.32839, found: 893.32840.

(1S,1'S)-(+)-(2,7-Di-tert-butyl-9,9-dimethyl-9H-xanthene-4,5-diyl)bis((2-ethylphenyl)(phenyl)phosphine) (compound I-B.o)

Yield: 72%; white solid; m.p.=139-140° C. (from ethanol);

$[\alpha]_D^{21}$=+46.8 (c1.0, CHCl$_3$);

$^1$H-NMR (CDCl$_3$): δ 7.35 (2H, d, J 2.4 Hz, arom. H), 7.25-7.13 (14H, m, arom. H), 6.97 (2H, m, arom H), 6.73 (2H, m, arom. H), 6.46 (2H, m, arom. H), 2.77 (4H, m, 2×CH$_2$), 1.66 (6H, s, 2×CH$_3$), 1.08 (18H, s, 6×CH$_3$), 1.07 (6H, t, J 7.5 Hz, 2×CH$_3$);

$^{13}$C-NMR (CDCl$_3$): δ 150.5 (m, 2×C—O), 148.5 (m, 2×C-Et), 145.1 (2×C—C), 137.6 (m, 2×C—P), 136.0 (m, 2×C—P), 134.0 (m, 4×CH), 133.5 (2×CH), 129.6 (2×CH), 128.7 (2×C—C), 128.4 (2×CH), 127.9 (m, 4×CH), 127.8 (m, 2×CH), 127.7 (2×CH), 125.6 (2×CH), 124.4 (m, 2×C—P), 122.7 (2×CH), 34.8 (m, C), 34.4 (2×C), 32.1 (2×CH$_3$), 31.3 (6×CH$_3$), 27.2 (m, 2×CH$_2$), 15.1 (2×CH$_3$);

$^{31}$P-NMR (CDCl$_3$): δ −24.9;

MS (EI, 70 eV) m/z: 746 (100, [M]$^+$), 745 (25, [M−H]$^+$), 731 (5, [M-CH$_3$]$^+$), 669 (16, [M-Ph]$^+$), 641 (14, [M-(2-Et-Ph)]$^+$), 533 (12, [M-PPh(2-Et-Ph)]$^+$); HRMS (ESI) [M+H]$^+$: m/z calc.: for C$_{51}$H$_{57}$OP$_2$ 747.38792, found: 747.38815.

(1S,1'S)-(+)-(2,7-Di-tert-butyl-9,9-dimethyl-9H-xanthene-4,5-diyl)bis((3-isopropylphenyl) (phenyl)phosphine) (compound I-B.p)

Yield: 53%; white solid; m.p.=74-75° C. (from CC cyclohexane/EtOAc 99/1);

$[\alpha]_D^{21}$=+26.7 (c1.0, CHCl$_3$);

$^1$H-NMR (CDCl$_3$): δ 7.34 (2H, d, J 2.4 Hz, arom. H), 7.23-7.18 (10H, m, arom. H), 7.15-7.06 (6H, m, arom H), 6.91 (2H, m, arom. H), 6.50 (2H, m, arom. H), 2.78 (2H, sept, J 6.9 Hz, 2×CH), 1.64 (6H, s, 2×CH$_3$), 1.14 (6H, d, J 6.9 Hz, 2×CH$_3$), 1.13 (6H, t, J 6.9 Hz, 2×CH$_3$), 1.08 (18H, s, 6×CH$_3$);

$^{13}$C-NMR (CDCl$_3$): δ 150.5 (m, 2×C—O), 148.2 (m, C-iPr), 145.1 (2×C—C), 137.7 (m, 2×C—P), 137.3 (m, 2×C—P), 133.9 (m, 4×CH), 132.2 (m, 2×CH), 131.3 (m, 2×CH), 129.3 (2×CH), 128.9 (2×C—C), 128.0 (2×CH), 128.0 (m, 2×CH), 127.9 (m, 4×CH), 126.2 (2×CH), 124.9 (m, 2×C—P), 122.7 (2×CH), 34.8 (m, C), 34.4 (2×C), 34.0 (2×CH), 31.9 (2×CH$_3$), 31.3 (6×CH$_3$), 24.0 (2×CH$_3$), 23.9 (2×CH$_3$);

$^{31}$P-NMR (CDCl$_3$): δ −16.0;

MS (EI, 70 eV) m/z; 774 (100, [M]$^+$), 759 (14, [M-CH$_3$]$^+$), 697 (2, [M-Ph]$^+$), 655 (2, [M-(3-iPr-Ph)]$^+$);

HRMS (ESI) [M+H]$^+$: m/z calc.: for C$_{53}$H$_{61}$OP$_2$ 775.41922, found: 775.41913.

(1S,1'S)-(+)-(2,7-Di-tert-butyl-9,9-dimethyl-9H-xanthene-4,5-diyl)bis((3-methyl-phenyl)(phenyl)phosphine) (compound I-B.q)

Yield: 55%; white solid; m.p.=71-73° C. (from CC cyclohexane/EtOAc 49/1); [α]n=+7.5 (c1.0, CHCl$_3$);

$^1$H-NMR (CDCl$_3$): δ 7.37 (2H, d, J 2.3 Hz, arom. H), 7.25-7.16 (10H, m, arom. H), 7.14-7.01 (6H, m, arom H), 6.94 (2H, m, arom. H), 6.55 (2H, m, arom. H), 2.23 (6H, s, 2×CH$_3$), 1.67 (6H, s, 2×CH$_3$), 1.10 (18H, s, 6×CH$_3$);

$^{13}$C-NMR (CDCl$_3$): δ 150.6 (m, 2×C—O), 145.2 (2×C—C), 137.8 (m, 2×C—P), 137.4 (m, 2×C-Me), 137.2 (m, 2×C—P), 134.7 (m, 2×CH), 133.9 (m, 4×CH), 130.8 (m, 2×CH), 129.4 (2×CH), 128.9 (2×CH), 128.9 (2×C—C), 127.9 (m, 2×CH), 127.9 (m, 4×CH), 127.9 (m, 2×CH), 124.6 (m, 2×C—P), 122.8 (2×CH), 34.8 (m, C), 34.5 (C), 31.9 (2×CH$_3$), 31.3 (6×CH$_3$), 21.4 (2×CH$_3$);

$^{31}$P-NMR (CDCl$_3$): δ −16.2;

MS (EI, 70 eV) m/z; 718 (100, [M]$^+$), 703 (21, [M-CH$_3$]$^+$),

HRMS (ESI) [M+H]$^+$: m/z calc.: for C$_{49}$H$_{53}$OP$_2$ 719.35662, found: 719.35724.

(1S,1'S)-(+)-(2,7-Di-ter-butyl-9,9-dimethyl-9H-xanthene-4,5-diyl)bis((3-ethylphenyl) (phenyl)phosphine) (compound I-B.r)

Yield: 49%; white solid; m.p.=66-68° C. (from CC cyclohexane/EtOAc 49/1);

$[\alpha]_D^{24}$=+16.5 (c1.0, CHCl$_3$);

$^1$H-NMR (CDCl$_3$): δ 7.35 (2H, d, J 2.3 Hz, arom. H), 7.23-7.17 (10H, m, arom. H), 7.15-7.04 (6H, m, arom H), 6.93 (2H, m, arom. H), 6.53 (2H, m, arom. H), 2.52 (4H, t, J 7.6 Hz 2×CH$_2$), 1.65 (6H, s, 2×CH$_3$), 1.09 (6H, t, J 7.6 Hz, 2×CH$_3$), 1.07 (18H, s, 6×CH$_3$);

$^{13}$C-NMR (CDCl$_3$): δ 150.6 (m, 2×C—O), 145.1 (2×C—C), 143.6 (m, C-Et) 137.7 (m, 2×C—P), 137.4 (m, 2×C—P), 133.9 (m, 4×CH), 133.6 (m, 2×CH), 131.1 (m, 2×CH), 129.4

(2×CH), 128.9 (2×C—C), 128.0 (m, 4×CH), 127.9 (2×CHC), 127.9 (m, 2×CH), 127.8 (2×CH), 124.7 (m, 2×C—P), 122.7 (2×CH), 34.8 (m, C), 34.5 (2×C), 31.9 (2×CH$_3$), 31.3 (6×CH$_3$), 28.8 (2×CH$_2$), 15.6 (2×CH$_3$);

$^{31}$P-NMR (CDCl$_3$): δ −16.1;

MS (EI, 70 eV) m/z; 746 (100, [M]$^+$), 731 (22, [M-CH$_3$]$^+$);

HRMS (ESI) [M+H]$^+$: m/z calc.: for C$_{51}$H$_{57}$OP$_2$ 747.38792, found: 747.38778.

(1S,1'S)-(−)-(2,7-DI-ter-butyl-9,9-dimethyl-9H-xanthene-4,5-diyl)bis((3-ethoxyphenyl) (phenyl)phosphine) (compound I-B.s)

Yield: 37%, white solid; m.p.=63-65° C. (CC with cyclohexane/EtOAc 99/1);

[α]$_D^{22}$=−8.3 (c1.0, CHCl$_3$);

$^1$H-NMR (CDCl$_3$): δ 7.36 (2H, d, J 2.3 Hz, arom. H), 7.24-7.15 (10H, m, arom. H), 7.10 (2H, m, arom. H), 6.79-6.70 (6H, m, arom. H), 6.57 (2H, m, arom. H), 3.85 (4H, m, 2×OCH$_2$), 1.64 (6H, s, 2×CH$_3$), 1.29 (6H, t, J 7.0 Hz, 2×CH$_3$), 1.09 (18H, s, 6×CH$_3$);

$^{13}$C-NMR (CDCl$_3$): δ 158.4 (m, C-OEt), 150.5 (m, 2×C—O), 145.2 (2×C—C), 139.1 (m, 2×C—P), 137.5 (m, 2×C—P), 133.9 (m, 4×CH), 129.3 (2×CH), 128.9 (2×C—C), 128.9 (m, 2×CH), 128.1 (2×CH), 127.9 (m, 4×CH), 126.2 (m, 2×CH), 124.5 (m, 2×C—P), 122.9 (2×CH), 119.1 (m, 2×CH), 115.0 (2×CH), 63.1 (2×OCH$_2$), 34.8 (m, C), 34.5 (2×C), 32.0 (2×CH$_3$), 31.3 (6×CH$_3$), 14.8 (2×CH$_3$);

$^{31}$P-NMR (CDCl$_3$): δ −15.1;

MS (EI, 70 eV) nm/z 778 (4, [M]$^+$);

HRMS (ESI) [M+H]$^+$: m/z calc.: for C$_{51}$H$_{57}$O$_3$P$_2$ 779.37775, found: 779.37755, [M+Na]$^+$: m/z calc.: for C$_{51}$H$_{56}$NaO$_3$P$_2$ 801.35969, found: 801.35945.

(1S,1'S)-(+)-(2,7-Di-tert-butyl-9,9-dimethyl-9H-xanthene-4,5-diyl)bis((4-(rac-2-methylbutyl)(phenyl)phenylphosphine) (compound I-B.t)

Yield: 30%; white solid; m.p.=70-72° C. (CC with cyclohexane/EtOAc 99/1);

[α]$_D^{22}$=+11.8 (c1.0, CHCl$_3$);

$^1$H-NMR (CDCl$_3$): δ 7.35 (2H, br d, J 2.4 Hz, arom. H), 7.25-7.18 (10H, m, arom. H), 7.10-7.05 (4H, m, arom. H), 6.98 (4H, m, arom. H), 6.49 (2H, m, arom. H), 2.60 (2H, m, 2×H$_A$—CH$_2$Ph), 2.34 (2H, m, 2×He-CH$_2$Ph), 1.66 (6H, s, C(CH$_3$)$_2$), 1.65 (2H, m, 2×CH), 1.38 (2H, m, 2×H$_A$—CH$_2$), 1.14 (2H, m, 2×He-CH$_2$), 1.07 (18H, s, 6×CH$_3$), 0.88 (6H, t, J 7.4 Hz, CH$_3$), 0.82 (6H, d, J 6.7 Hz, CH$_3$);

$^{13}$C-NMR (CDCl$_3$): δ 150.4 (m, 2×C—O), 145.0 (2×C—C), 141.8 (2×C—C), 138.0 (2×C—P), 134.3 (2×C—P), 133.9 (m, 4×CH), 133.8 (m, 4×CH), 129.4 (2×CH), 129.0 (m, 4×C—H), 128.7 (2×C—C), 127.9 (m, 4×CH), 127.8 (2×CH), 125.1 (m, 2×C—P), 122.8 (2×CH), 43.2 (CH$_2$Ph), 36.6 (CH), 34.8 (m, C), 34.4 (C), 32.2 (2×CH$_3$), 31.2 (6×CH$_3$), 29.1 (CH$_2$), 19.0 (CH$_3$), 11.5 (CH$_3$);

$^{31}$P-NMR (CDCl$_3$): δ three signals in each case −17.1 ppm (three diastereomers);

MS (EI, 70 eV) m/z; 830 (100, [M]$^+$), 815 (9, [M-CH$_3$]$^+$), 754 (34, [M-Ph+H]$^+$), 684 (24, [M-(4-(2-Me-butyl)-Ph)+H]$^+$), 576 (24, M-PPh (4-(2-Me-butyl)-Ph)+H]$^+$);

HRMS (ESI) [M+H]$^+$: m/z calc.: for C$_{57}$H$_{69}$OP$_2$ 831.48182, found: 831.48104, [M+Na]$^+$:

calc.: for C$_{57}$H$_{68}$NaOP$_2$ 853.46376, found: 853.46323.

(1S,1'S)-(−)-2,7-Di-tert-butyl-9,9-dimethyl-9H-xanthene-4,5-diyl)bis((4-ethoxyphenyl) (phenyl)phosphine) (compound I-B.u)

Yield: 65%, white solid; m.p.=84-86° C. (ethanol);

[α]$_D^{22}$=−39.0 (c1.0, CHCl$_3$);

$^1$H-NMR (CDCl$_3$): δ 7.36 (2H, d, J 2.4 Hz, arom. H), 7.24-7.10 (14H, m, arom. H), 6.76 (4H, m, arom. H), 6.57 (2H, m, arom. H), 4.01 (4H, q, J 7.0 Hz, 2×OCH$_2$), 1.67 (6H, s, 2×CH$_3$), 1.42 (6H, t, J 7.0 Hz, 2×CH$_3$), 1.12 (18H, s, 6×CH$_3$);

$^{13}$C-NMR (CDCl$_3$): δ 159.2 (2×C—OEt), 150.4 (m, 2×C—O), 145.1 (2×C—C), 138.4 (m, 2×C—P), 135.7 (m, 4×CH), 133.5 (m, 4×CH), 129.2 (2×CH), 128.8 (2×C—C), 127.9 (m, 2×C—P), 127.9 (m, 4×CH), 127.6 (2×CH), 125.1 (m, 2×C—P), 122.7 (2×CH), 114.3 (m, 4×CH), 63.1 (2×OCH$_2$), 34.8 (m, C), 34.4 (2×C), 32.1 (2×CH$_3$), 31.3 (6×CH$_3$), 14.8 (2×CH$_3$);

$^{31}$P-NMR (CDCl$_3$): δ −17.5;

MS (EI, 70 eV) m/z; 778 (100, [M]$^+$), 701 (16, [M-Ph]$^+$), 551 (5, [M-PPh(4-EtO-Ph)+H]$^+$); HRMS (ESI) [M+H]$^+$: m/z calc.: for C$_{51}$H$_{57}$O$_3$P$_2$ 779.37775, found: 779.37787.

(1S,1'S)-(−)-(oxybis(2,1-phenylene))bis((2-methoxyphenyl) (phenyl)phosphine) (compound I-C.a)

Yield 18%; white solid; m.p.=148-149° C. (from CH$_2$Cl$_2$/hexane);

[α]$_D^{21}$=−14.7 (c1.0, CHCl$_3$);

$^1$H-NMR (CDCl$_3$): δ 7.28-7.15 (14H, m, arom. H), 6.94 (2H, dt, J 7.5, 1.1 Hz, arom. H), 6.84-6.74 (6H, m, arom. H), 6.73-6.64 (4H, m, arom. H), 3.69 (6H, s, 2×OCH$_3$);

$^{13}$C-NMR (CDCl$_3$): δ 160.8 (d, J 15.8 Hz, 2×C—OMe), 159.8 (d, J 17.7 Hz, 2×C—O), 135.7 (d, J 9.0 Hz, 2×C—P), 134.1 (d, J 20.4 Hz, 4×CH), 134.1 (d, J 2.4 Hz, 2×Ch), 133.8 (2×CH), 130.2 (2×CH), 129.9 (2×CH), 128.4 (2×CH), 128.1 (d, J 7.5 Hz, 4×CH), 127.9 (d, J 113.2 Hz, 2×C—P), 124.6 (d, J 10.8 Hz, 2×C—P), 123.4 (2×CH), 120.9 (2×CH), 118.5 (2×CH), 110.1 (2×CH), 55.5 (2×OCH$_3$);

$^{31}$P-NMR (CDCl$_3$): δ −25.7;

MS (EI, 70 eV) m/z: 598 (12, [M]$^+$), 597 (21, [M−H]$^+$), 521 (37, [M-Ph]$^+$), 491 (45, [M-(2-MeO-Ph)]$^+$), 384 (93, [M-PPh(2-MeO-Ph)+H]$^+$), 383 (100, [M-PPh(2-MeO-Ph)]$^+$), 215 (15, [PPh(2-MeO-Ph)]$^+$);

HRMS (EI) [M−H]$^+$: m/z calc.: for C$_{38}$H$_{31}$O$_3$P$_2$ 597.17429, found: 597.17420.

(1S,1'S)-(−)-(Oxybis(2,1-phenylene))bis((2-methylphenyl) (phenyl)phosphine) (compound I-C.b)

Yield 37%; white solid; m.p.=140-142° C. (from CH$_2$Cl$_2$/hexane);

[α]$_D^{19}$=−32.2 (c1.0, CHCl$_3$);

$^1$H-NMR (CDCl$_3$): δ 7.34-7.15 (14H, m, arom. H), 7.11-7.02 (4H, m, arom. H), 6.96 (2H, dt, J 7.4, 1.0 Hz, arom. H), 6.84-6.71 (6H, m, arom. H), 2.23 (6H, s, 2×CH$_3$);

$^{13}$C-NMR (CDCl$_3$): δ 159.3 (d, J 18.3 Hz, 2×C—O), 142.0 (d, J 27.0 Hz, 2×C—C), 135.8 (d, J 11.5 Hz, 2×C—P), 135.2 (d, J 12.6 Hz, 2×C—P), 134.2 (d, J 21.3 Hz, 4×CH), 134.1 (2×CH), 132.7 (2×CH), 130.1 (2×CH), 129.9 (m, 2×CH), 128.4 (2×CH), 128.3 (4×CH), 128.2 (2×CH), 128.2 (m, 2×C—P), 125.7 (2×CH), 123.6 (2×CH), 118.0 (2×CH), 21.3 (d, J 22.2 Hz, 2×CH$_3$);

$^{31}$P-NMR (CDCl$_3$): δ −24.0;

MS (EI, 70 eV) m/z: 566 (5, [M]$^+$), 565 (9, [M−H]$^+$), 489 (12, [M-Ph]$^+$), 475 (37, [M-(2-Me-Ph)]$^+$), 367 (100, [M-PPh(2-Me-Ph)]$^+$), 199 (72, [PPh(2-Me-Ph)]$^+$);

HRMS (ESI) [M+H]$^+$: m/z calc.: for C$_{38}$H$_{33}$OP$_2$ 567.20012, found: 567.20006, [M+Na]$^+$: calc.: for C$_{36}$H$_{32}$NaOP$_2$ 589.18206, found: 589.18073.

(1S,1'S)-(−)-(Oxybis(2,1-phenylene))bis((4-methoxyphenyl)(phenyl)phosphine) (compound I-C.c)

Yield: 61%; white solid; m.p.=73-75° C. (CC with cyclohexane/EtOAc 19/1):

[α]$_D^{23}$=−30.0 (c1.0, CHCl$_3$);

$^1$H-NMR (CDCl$_3$): δ 7.27-7.12 (16H, m, arom. H), 6.94 (2H, dt, J 7.4, 0.8 Hz, arom. H), 6.83-6.77 (6H, m, arom. H), 6.77 (2H, dd, J 8.1, 4.3 Hz, arom. H), 3.79 (6H, s, 2×OCH$_3$);

¹³C-NMR (CDCl₃): δ 160.1 (2×C—OMe), 159.1 (d, J 17.6 Hz, 2×C—O), 137.4 (d, J 11.4 Hz, 2×C—P), 135.6 (d, J 22.7 Hz, 4×CH), 133.8 (2×CH), 133.5 (d, J 20.5 Hz, 4×CH), 130.0 (2×CH), 129.4 (d, J 15.7 Hz, 2×C—P), 128.1 (m, 6×CH), 127.0 (d, J 8.3 Hz, 2×C—P), 123.5 (2×CH), 118.0 (2×CH), 114.0 (m, 4×CH), 55.1 (2×OCH₃);
³¹P-NMR (CDCl₃): δ −17.6;
MS (EI, 70 eV) m/z: 598 (3, [M]⁺), 597 (5, [M–H]⁺), 521 (5, [M-Ph]⁺), 383 (100, [M-PPh(4-MeO-Ph)]⁺);
HRMS (ESI) measured as dioxide [M+H]⁺: m/z calc.: for C₃₈H₃₃O₅P₂ 631.17977, found: 631.17934, [M+Na]: m/z calc.: for C₃₈H₃₂NaO₅P₂ 653.16172, found: 653.16234.

(1S,1'S)-(−)-(Oxybis(2,1-phenylene))bis((4-methylphenyl)(phenyl)phosphine) (compound I-C.d)

Yield 65%; white solid; m.p.=60-62° C. (CC with cyclohexane/EtOAc 19/1);
[α]_D²³=−8.5 (c1.0, CHCl₃);
¹H-NMR (CDCl₃): δ 7.26-7.03 (20H, m, arom. H), 6.95 (2H, dt, J 7.5, 1.1 Hz, arom. H), 6.80 (2H, ddd, J 7.6, 3.3, 1.8 Hz, arom. H), 6.68 (2H, ddd, J 8.2, 4.4, 1.1 Hz, arom. H), 2.32 (6H, s, 2×CH₃);
¹³C-NMR (CDCl₃): δ 159.2 (d, J 17.6 Hz, 2×C—O), 138.3 (2×C—C), 136.9 (d, J 11.5 Hz, 2×C—P), 134.1 (2×CH), 133.9 (4×CH), 133.7 (d, J 20.7 Hz, 4×CH), 133.2 (d, J 10.0 Hz, 2×C—P), 130.0 (2×CH), 129.2 (d, J 14.5 Hz, 2×C—P), 129.1 (m, 4×CH), 128.2 (m, 2×CH), 128.1 (4×CH), 123.5 (2×CH), 118.1 (2×CH), 21.3 (d, J 22.2 Hz, 2×CH₃);
³¹P-NMR (CDCl₃): δ −17.1;
MS (EI, 70 eV) m/z: 566 (10, [M]⁺), 565 (20, [M–H]⁺), 489 (20, [M-Ph]⁺), 475 (14, [M-(4-Me-Ph)]⁺), 367 (100, [M-PPh(4-Me-Ph)]⁺), 199 (65, [PPh(4-Me-Ph)]⁺);
HRMS (EI) [M–H]⁺: m/z calc.: for C₃₈H₃₁OP₂ 565.18447, found: 565.18421.

(1S,1'S)-(−)-(Oxybis(2,1-phenylene))bis((1-naphthyl)(phenyl)phosphine) (compound I-C.e)

Yield 40%; white solid; m.p.=195-198° C. (CC with cyclohexane/EtOAc 19/1 and subsequent crystallization from CH₂Cl₂/hexane);
[α]_D²⁴=−181.2 (c1.0, CHCl₃);
¹H-NMR (CDCl₃): δ 8.18 (2H, dd, J 8.3, 4.0 Hz, arom. H), 7.71 (2H, d, J 8.3 Hz, arom. H), 7.45-7.39 (4H, m, arom. H), 7.32 (2H, m, arom. H), 7.27-7.17 (12H, m, arom. H), 7.07 (2H, t, J 7.3 Hz, arom. H), 6.98-6.89 (4H, m, arom. H), 6.79 (2H, m, arom. H), 6.70 (2H, m, arom. H);
¹³C-NMR (CDCl₃): δ 159.5 (d, J 17.6 Hz, 2×C—O), 135.1 (d, J 10.1 Hz, 2×C—C), 134.9 (d, J 23.1 Hz, 2×C—P), 134.6 (2×CH), 134.4 (d, J 21.1 Hz, 4×CH), 133.1 (d, J 14.4 Hz, 2×C—C), 133.1 (m, 2×C—P), 131.6 (2×CH), 130.3 (2×CH), 128.8 (2×CH), 128.6 (2×CH), 128.6 (2×CH), 128.3 (m, 4×CH), 128.1 (d, J 14.9 Hz, 2×C—P), 126.3 (d, J 27.1 Hz, 2×CH), 125.6 (2×CH), 125.4 (2×CH), 125.1 (2×CH), 123.7 (2×CH), 118.1 (2×CH);
³¹P-NMR (CDCl₃): δ −23.1 ppm;
MS (EI, 70 eV) m/z, 638 (2, [M]⁺), 561 (3, [M-Ph]⁺), 511 (4, [M-Naphthyl]⁺), 403 (100, [M-PPh(Naphthyl)]⁺),
HRMS (ESI) [M+H]⁺: m/z calc.: for C₄₄H₃₃OP₂ 639.20012, found: 639.20023, [M+Na]⁺:
m/z calc.: for C₄₄H₃₂NaOP₂ 661.18206, found: 661.18174.

(1S,1'S)-(−)-(Oxybis(2,1-phenylene))bis((2-naphthyl)(phenyl)phosphine) (compound I-C.f)

Yield 39%; white solid; m.p.=148-150° C. (from CH₂Cl₂/hexane);
[α]_D²¹=−174.0 (c1.0, CHCl₃);
¹H-NMR (CDCl₃): δ 7.72 (2H, dd, J 7.8, 1.7 Hz, arom. H), 7.65-7.50 (6H, m, arom. H), 7.48-7.35 (4H, m, arom. H), 7.31-7.09 (14H, m, arom. H), 6.93 (2H, dt, J 7.5, 1.1 Hz, arom. H), 6.83-6.73 (4H, m, arom. H);
¹³C-NMR (CDCl₃): δ 159.3 (d, J 17.9 Hz, 2×C—O), 134.6 (m, C—P), 134.1 (d, J 20.2 Hz, 4×CH), 134.0 (m, 2×C—P), 134.0 (m, 2×CH), 133.8 (m, C—P), 133.2 (2×C—C), 130.3 (2×CH), 130.0 (d, J 19.6 Hz, 2×CH), 128.8 (m, 2×C—P), 128.6, (2×C—C), 128.5 (2×CH), 128.3 (m, 4×CH), 128.1 (2×CH), 127.6 (2×CH), 127.4 (m, 2×CH), 126.3 (2×CH), 125.8 (2×CH), 123.7 (2×CH), 118.1 (2×CH);
³¹P-NMR (CDCl₃): δ −15.5;
MS (EI, 70 eV) nm/z 638 (14, [M]⁺), 637 (23, [M–H]⁺), 561 (46, [M-Ph]⁺), 511 (34, [M-Naphthyl]⁺), 404 (91, [M-PPh (Naphthyl)+H]⁺), 403 (39, [M-PPh(Naphthyl)]⁺), 362 (100);
HRMS (EI) [M–H]⁺: m/z calc.: for C₄₄H₃₁OP₂ 637.18447, found: 637.18423.

(1R,1'R)-(+)-(Oxybis(2,1-phenylene))bis((9-phenanthryl)(phenyl)phosphine) (compound I-C.g*)

The title compound was prepared analogously by reaction with the compound from example 3g*.
Yield 51%, white solid; m.p.=178-180° C. (from CH₂Cl₂/hexane);
[α]_D²⁴=+90.2 (c1.0, CHCl₃);
¹H-NMR (CDCl₃): δ 8.58-8.45 (4H, m, arom. H), 8.15 (2H, m, arom. H), 7.59-7.37 (8H, m, arom. H), 7.32-7.16 (16H, m, arom. H), 6.96-6.85 (4H, m, arom. H), 6.82-6.74 (2H, m, arom. H);
¹³C-NMR (CDCl₃): δ 159.4 (t, J 18.3 Hz, 2×C—O), 135.4 (d, J 10.2 Hz, 2×C—C), 134.8 (2×CH), 134.4 (d, J 21.3 Hz, 4×CH), 133.3 (2×CH), 133.0 (d, J 21.9 Hz, C—P), 132.3 (d, J 14.6 Hz, 2×C—C), 131.3 (2×C—C), 130.5 (2×C—C), 130.3 (2×CH), 129.8 (m, 2×C—P), 128.7 (d, J 3.5 Hz, 4×CH), 128.3 (m, 4×CH), 128.0 (d, J 15.4 Hz, 2×C—P), 127.0 (d, J 28.6 Hz, 2×CH), 126.7 (2×CH), 126.3 (2×CH), 126.2 (2×CH), 126.0 (2×CH), 123.7 (2×CH), 122.6 (2×CH), 122.2 (2×CH), 117.9 (2×CH);
³¹P-NMR (CDCl₃): δ −22.6;
MS (EI, 70 eV) m/z; 738 (12, [M]⁺), 661 (7, [M-Ph]⁺), 561 (17, [M-C₁₄H₉]⁺), 453 (100, [M-PPh(9-phenanthryl)] P⁺);
HRMS (EI) [M]⁺: m/z calc.: for C₅₂H₃₆OP₂ 738.22359, found: 738.22137.

(1S,1'S)-(−)-(Oxybis(2,1-phenylene))bis((3,5-dimethoxyphenyl)(phenyl)phosphine) (compound I-C.h)

Yield 80%; white solid; m.p.=120-123° C. (from CH₂Cl₂/hexane);
[α]_D²⁰=−33.4 (c1.0, CHCl₃);
¹H-NMR (CDCl₃): δ 7.29-7.20 (10H, m, arom. H), 7.17 (2H, m, arom. H), 6.94 (2H, dt, J 7.6, 1.1 Hz, arom. H), 6.77 (2H, ddd, J 7.7, 4.0, 1.7 Hz, arom. H), 6.77 (2H, ddd, J 8.1, 4.4, 0.8 Hz, arom. H), 6.37 (2H, m, arom. H), 6.35 (4H, m, 2H), 3.67 (12H, s, 4×OCH₃);
¹³C-NMR (CDCl₃): δ 160.4 (m, 4×C—OMe), 159.1 (d, J 18.0 Hz, 2×C—O), 138.9 (d, J 12.2 Hz, 2×C—P), 136.3 (d, J 11.9 Hz, 2×C—P), 134.0 (d, J 21.1 Hz, 4×CH), 133.9 (2×CH), 130.1 (2×CH), 128.7 (d, J 16.4 Hz, 2×C—P), 128.5 (m, 2×CH), 128.2 (m, 4×CH), 123.6 (2×CH), 117.9 (2×CH), 111.3 (m, 4×CH), 55.2 (4×OCH₃);
³¹P-NMR (CDCl₃): δ −14.2;
MS (EI, 70 eV) m/z; 658 (2, [M]⁺), 643 (2, [M-CH₃]⁺), 581 (10, [M-Ph]⁺), 521 (10, [M-(3,5-MeO-Ph)]⁺), 413 (100, [M-PPh((3, 5-MeO-Ph)]⁺;
HRMS (ESI) [M+H]⁺: m/z calc.: for C₄₀H₃₇OP₂ 659.21107, found: 659.21143.

(1S,1'S)-(+)-(oxybis(2,1-phenylene))bis((2-isopropylphenyl)(phenyl)phosphine) (compound I-C.j)

Yield: 59%, white solid; m.p.=156-157° C. (from CH$_2$Cl$_2$/hexane);

[α]$_D^{22}$=+7.6 (c1.0, CHCl$_3$);

$^1$H-NMR (CDCl$_3$): δ 7.33-7.13 (14H, m, arom. H), 7.10 (2H, m, arom. H), 7.00 (2H, m, arom. H), 6.90 (2H, dt, J 7.4, 1.0 Hz, arom. H), 6.81 (2H, m, arom. H), 6.75 (2H, m, arom. H), 6.52 (2H, m, arom. H), 3.63 (2H, m, 2×OCH), 1.07 (6H, d, J 6.7 Hz, 2×CH$_3$), 1.05 (6H, d, J 6.7 Hz, 2×CH$_3$);

$^{13}$C-NMR (CDCl$_3$): δ 159.2 (d, J 18.7 Hz, 2×C—O), 153.4 (d, J 25.5 Hz, 2×C—C), 136.7 (m, 2×C—P), 134.2 (2×CH), 134.1 (d, J 21.4 Hz, 4×CH), 134.1 (m, 2×C—P), 133.7 (2×CH), 129.9 (m, 2×CH), 129.4 (d, J 16.3 Hz, 2×C—P), 129.0 (2×CH), 128.2 (2×CH), 128.1 (m, 4×CH), 125.8 (2×CH), 125.1 (m, 2×CH), 123.3 (2×CH), 117.9 (2×CH), 31.1 (d, J 26.9 Hz, 2×CH), 24.0 (2×CH$_3$), 23.9 (2×CH$_3$);

$^{31}$P-NMR (CDCl$_3$): δ −27.0;

MS (EI, 70 eV) m/z: 622 (1, [M]$^+$), 621 (2, [M−H]$^+$), 545 (3, [M-Ph]$^+$), 503 (8, [M-(2-iPr-Ph]$^+$), 395 (100, [M-PPh(2-iPr-Ph)]$^+$), 227 (8, [PPh (2-iPr-Ph)]$^+$);

HRMS (ESI) [M+H]$^+$: m/z calc.: for C$_{42}$H$_{41}$OP$_2$ 623.26272, found: 623.26232, [M+Na]$^+$:

m/z calc.: for C$_{42}$H$_{40}$NaOP$_2$ 645.24466, found: 645.24396.

(1S,1'S)-(+)-(Oxybis(2,1-phenylene))bis((2-ethoxyphenyl)(phenyl)phosphine) (compound I-C.k)

Yield: 58%; white solid; m.p.=62-64° C. (from CC with cyclohexane/EtOAc 49/1);

[α]$_D^{23}$=+12.3 (c1.0, CHCl$_3$);

$^1$H-NMR (CDCl$_3$): δ 7.28-7.15 (14H, m, arom. H), 6.94 (2H, m, arom. H), 6.88 (2H, m, arom. H), 6.77 (2H, m, arom. H), 6.73-6.63 (6H, m, arom. H), 3.89 (4H, m, 2×OCH$_2$), 1.08 (6H, t, J 7.0 Hz, 2×CH$_3$);

$^{13}$C-NMR (CDCl$_3$): δ 160.0 (d, J 14.7 Hz, 2×C—OEt), 159.9 (d, J 117.1 Hz, 2×C—O), 136.1 (d, J 9.6 Hz, 2×C—P), 134.3 (d, J 20.9 Hz, 4×CH), 134.2 (2×CH), 133.6 (d, J 2.6 Hz, 2×CH, 130.1 (2×CH), 129.6 (2×CH), 128.3 (d, J 13.9 Hz, 2×C—P), 128.2 (2×CH), 128.0 (d, J 7.4 Hz, 4×CH), 125.3 (d, J 12.3 Hz, 2×C—P), 123.3 (2×CH), 120.7 (2×CH), 118.5 (2×CH), 110.9 (2×CH), 63.7 (2×OCH$_2$), 14.4 (2×CH$_3$); $^{31}$P-NMR (CDCl$_3$): δ −24.6 ppm;

MS (EI, 70 eV) nm/z 626 (10, [M]$^+$), 625 (13, [M−H]$^+$), 581 (8, [M-OEt]$^+$), 549 (20, [M-Ph]$^+$), 505 (21, [M-(2-EtO-Ph)]$^+$), 397 (100, [M-PPh(2-EtO-Ph)]$^+$;

HRMS (EI) [M]$^+$: m/z calc.: for C$_{40}$H$_{36}$O$_3$P$_2$ 626.21342, found: 626.21025, [M−H]$^+$: m/z calc.: for C$_{40}$H$_{35}$O$_3$P$_2$ 625.20599, found: 625.20525;

HRMS (ESI) [M+H]$^+$: m/z calc.: for C$_{40}$H$_{37}$O$_3$P$_2$ 627.22124, found: 627.22137.

(1S,1'S)-(−)-(Oxybis(2,1-phenylene))bis((3-methoxyphenyl)(phenyl)phosphine) (compound I-C.l)

Yield: 47%; white solid; m.p.=59-60° C. (from CC with cyclohexane/EtOAc 49/1);

[α]$_D^{22}$=−17.1 (c1.0, CHCl$_3$);

$^1$H-NMR (CDCl$_3$): δ 7.37-7.14 (14H, m, arom. H), 6.95 (2H, m, arom. H), 6.88-6.74 (8H, m, arom. H), 6.70 (2H, arom. H), 3.69 (4H, m, 2×OCH$_3$);

$^{13}$C-NMR (CDCl$_3$): δ 159.2 (m, 2×C—OEt), 159.1 (d, J 17.8 Hz, 2×C—O), 138.1 (d, J 12.6 Hz, 2×C—P), 136.4 (d, J 12.1 Hz, 2×C—P), 133.9 (d, J 20.7 Hz, 4×CH), 133.9 (2×CH), 130.1 (2×CH), 129.2 (m, 2×CH), 128.8 (d, J 16.7 Hz, 2×C—P), 128.4 (2×CH), 128.2 (m, 4×CH), 126.1 (d, J 19.4 Hz, 2×CH), 123.5 (2×CH), 118.9 (d, J 23.0 Hz, 2×CH), 117.9 (2×CH), 114.1 (2×CH), 55.1 (2×OCH$_3$); $^{31}$P-NMR (CDCl$_3$): δ −15.6 ppm;

MS (EI, 70 eV) m/z: 598 (10, [M]$^+$), 597 (19, [M−H]$^+$), 521 (20, [M-Ph]$^+$), 491 (21, [M-(3-MeO-Ph)]$^+$), 383 (100, [M-PPh(3-MeO-Ph)]$^+$;

HRMS (ESI) [M+H]$^+$: m/z calc.: for C$_{38}$H$_{33}$O$_3$P$_2$ 599.18994, found: 599.18978, [M+Na]$^+$:

m/z calc.: for C$_{38}$H$_{32}$NaO$_3$P$_2$ 621.17189, found: 621.17144.

(1S,1'S)-(−)-(Oxybis(2,1-phenylene))bis((3-isopropoxyphenyl)(phenyl)phosphine) (compound I-C.m)

Yield: 40%; white solid; m.p.=60-62° C. (from CC with cyclohexane/EtOAc 49/1);

[α]$_D^{22}$=−0.7 (c1.0, CHCl$_3$);

$^1$H-NMR (CDCl$_3$): δ 7.29-7.12 (14H, m, arom. H), 6.95 (2H, dt, J 7.5, 1.1 Hz, arom. H), 6.88-6.74 (8H, m, arom. H), 6.70 (2H, ddd, J 8.2 3.6 1.1 Hz arom. H), 4.41 (4H, sept, J 6.1 Hz, 2×OCH), 1.26 (6H, d, J 6.1 Hz, 2×CH$_3$), 1.24 (6H, d, J 6.1 Hz, 2×CH$_3$);

$^{13}$C-NMR (CDCl$_3$): δ 159.2 (d, J 18.3 Hz, 2×C—O), 157.6 (m, 2×C—OiPr), 138.1 (d, J 11.9 Hz, 2×C—P), 136.4 (d, J 11.9 Hz, 2×C—P), 133.9 (2×CH), 133.8 (d, J 20.7 Hz, 4×CH), 130.1 (2×CH), 129.2 (m, 2×CH), 129.0 (d, J 16.4 Hz, 2×C—P), 128.3 (2×CH), 128.2 (m, 4×CH), 126.1 (d, J 20.7 Hz, 2×CH), 123.5 (2×CH), 120.8 (d, J 22.5 Hz, 2×CH), 117.9 (2×CH), 116.2 (2×CH), 69.6 (2×OCH), 22.0 (2×CH$_3$), 21.9 (2×CH$_3$);

$^{31}$P-NMR (CDCl$_3$): δ −15.7 ppm;

MS (EI, 70 eV) m/z: 577 (1, [M-Ph]$^+$), 411 (47, [M-PPh(3-iPrO-Ph)]$^+$), 243 (6, [PPh(3-iPrO-Ph)]$^+$), 165 (66, [P(3-iPrO-Ph)-H]$^+$, 59 (100, [C$_3$H$_7$O]$^+$);

HRMS (ESI) [M+H]$^+$: m/z calc.: for C$_{42}$H$_{41}$O$_3$P$_2$ 655.25254, found: 655.25212.

(1S,1'S)-(−)-(Oxybis(2,1-phenylene))bis((dibenzo[b,d]-furan-4-yl)(phenyl)phosphine) (compound I-C.n)

Yield: 22%; white solid; m.p.=110-112° C. (from CC with cyclohexane/EtOAc 49/1);

[α]$_D^{22}$=−257.5 (c1.0, CHCl$_3$);

$^1$H-NMR (CDCl$_3$): δ 7.73 (2H, m, arom. H), 7.47-7.17 (18H, m, arom. H), 7.01-6.90 (4H, m, arom. H), 6.86-6.74 (6H, m, arom. H), 6.65 (2H, ddd, J 7.6, 4.3, 1.6 Hz, arom. H);

$^{13}$C-NMR (CDCl$_3$): δ 159.6 (d, J 117.8 Hz, 2×C—O), 157.1 (d, J 17.5 Hz, 2×C—O), 155.9 (2×C—O), 134.8 (d, J 10.1 Hz, 2×C—P), 134.2 (d, J 21.2 Hz, 4×CH), 134.1 (2×CH), 130.7 (2×CH), 130.5 (2×CH), 128.8 (2×CH), 128.4 (d, J 7.6 Hz, 4×CH), 127.3 (d, J 13.9 Hz, 2×C—P), 126.8 (2×CH), 124.3 (2×C—C), 123.9 (2×CH), 122.7 (2×C—C), 122.3 (2×CH), 122.2 (2×CH), 120.7 (2×CH), 120.1 (2×CH), 118.7 (d, J 15.9 Hz, 2×C—P), 118.3 (2×CH), 111.8 (2×CH);

$^{31}$P-NMR (CDCl$_3$): δ −28.5 ppm;

MS (EI, 70 eV) m/z: 718 (5, [M]$^+$), 717 (7, [M−H]$^+$), 641 (10, [M-Ph]$^+$), 551 (9, [M-DBF]$^+$), 443 (100, [M-PPh(DBF)]$^+$), 275 (14, [PPh(DBF)]$^+$);

HRMS (ESI) [M+H]$^+$: m/z calc.: for C$_{48}$H$_{33}$O$_3$P$_2$ 719.18994, found: 719.18952, [M+Na]$^+$: m/z calc.: for C$_{48}$H$_{32}$NaO$_3$P$_2$ 741.17189, found: 741.17165.

(1S,1'S)-(−)-(Oxybis(2,1-phenylene))bis((2-ethylphenyl)(phenyl)phosphine) (compound I-C.o)

Yield: 33%; white solid; m.p.=129-131° C. (from CH$_2$Cl$_2$/hexane);

[α]$_D^{22}$=−9.5 (c1.0, CHCl$_3$);

$^1$H-NMR (CDCl$_3$): δ 7.28-7.12 (16H, m, arom. H), 7.03 (2H, dt, J 7.5, 1.4 Hz, arom. H), 6.93 (2H, dt, J 7.5, 1.0 Hz, arom. H), 6.85 (2H, ddd, J 7.6, 4.2, 1.3 Hz, arom. H), 6.75 (2H, dt, J 7.6, 3.9, 1.6 Hz, arom. H), 6.61 (2H, m, arom. H), 2.75 (4H, m, 2×CH$_2$) 1.05 (6H, t, J 7.4 Hz, 2×CH$_3$);

$^{13}$C-NMR (CDCl$_3$): δ 159.3 (d, J 18.2 Hz, 2×C—O), 148.5 (d, J 27.1 Hz, 2×C—C), 136.4 (d, J 11.2 Hz, 2×C—P), 134.6 (d, 113.4 Hz, 2×C—P), 134.1 (d, J 21.4 Hz, 4×CH), 134.1 (2×CH), 133.6 (2×CH), 130.0 (2×CH), 128.9 (d, J 15.9 Hz, 2×C—P), 128.7 (m, 2×CH), 128.3 (2×CH), 128.2 (m, 4×CH), 128.0 (m, 2×CH), 125.8 (2×CH), 123.5 (2×CH), 118.0 (2×CH), 27.4 (d, J 23.6 Hz, 2×CH$_2$), 15.3 (2×CH$_3$);

$^{31}$P-NMR (CDCl$_3$): δ −26.0 ppm;

MS (EI, 70 eV) m/z: 594 (1, [M]$^+$), 517 (2, [M-Ph]$^+$), 489 (37, [M-(2-Et-Ph)]$^+$), 381 (100, [M-PPh(2-Et-Ph)]$^+$), 289 (17, [C$_{20}$H$_{18}$P]$^+$);

HRMS (ESI) [M+H]$^+$: m/z calc.: for C$_{40}$H$_{37}$OP$_2$ 595.23142, found: 595.23150.

(1S,1'S)-(+)-(Oxybis(2,1-phenylene))bis((3-isopropylphenyl)(phenyl)phosphine) (compound I-C.p)

Yield: 40%; white solid, m.p.=118-120° C. (from CH$_2$Cl$_2$/hexane);

[α]$_D^{22}$=+19.4 (c1.0, CHCl$_3$);

$^1$H-NMR: δ 7.28-7.10 (18H, m, arom. H), 6.99 (2H, m, arom. H), 6.93 (2H, ddd, J 7.4, 7.4, 1.1 Hz, arom. H), 6.80 (2H, ddd, J 7.5, 4.2, 1.6 Hz, arom. H), 6.64 (2H, ddd, J 8.2, 4.6, 1.0 Hz, arom. H), 2.81 (2H, sept, J 6.9 Hz 2×CH), 1.17 (6H, t, J 6.9 Hz, 2×CH$_3$), 1.17 (6H, t, J 6.9 Hz, 2×CH$_3$);

$^{13}$C-NMR: δ 159.2 (d, J 17.7 Hz, 2×C—O), 148.5 (m, 2×C—C), 136.7 (m, 2×C—P), 136.4 (m, 2×C—P), 133.9 (2×CH), 133.7 (d, J 21.0 Hz, 4×CH), 132.5 (d, J 25.4 Hz, 2×CH), 131.4 (d, J 16.9 Hz, 2×CH), 130.0 (2×CH), 129.3 (d, J 16.6 Hz, 2×C—P), 128.3-1.28.1 (2×CH, 2×CH, 4×CH), 126.5 (2×CH) 123.4 (2×CH), 118.0 (2×CH), 34.0 (2×CH), 23.9 (4×CH$_3$);

$^{31}$P-NMR: δ −16.2;

MS (EI, 70 eV) m/z: 622 (2, [M]$^+$), 621 (4, [M-H]$^+$), 577 (6, [M-Ph]$^+$), 503 (5, [M-(3-iPr-Ph)]$^+$), 396 (76, [M-PPh(3-Pr-Ph)+H]$^+$), 395 (100, [M-PPh(3-iPr-Ph)]$^+$);

HRMS (ESI) [M+H]$^+$: m/z calc.: for C$_{42}$H$_{41}$OP$_2$ 623.26272, found 623.26326.

(1S,1'S)-(−)-(Oxybis(2,1-phenylene))bis((3-methylphenyl)(phenyl)phosphine) (compound I-C.q)

Yield: 65%; white solid; m.p.=132-133° C. (from CC with cyclohexane/EtOAc 49/1);

[α]$_D^{23}$=−16.6 (c1.0, CHCl$_3$);

$^1$H-NMR (CDCl$_3$): δ 7.27-7.01 (18H, m, arom. H), 6.96 (2H, m, arom. H), 6.93 (2H, t, J 7.7 Hz, arom. H), 6.78 (2H, m, arom. H), 6.65 (2H, m, arom. H), 2.24 (6H, s, 2×CH$_3$);

$^{13}$C-NMR (CDCl$_3$): δ 159.2 (d, 117.4 Hz, 2×C—O), 137.6 (m, 2×C—C), 136.7 (m, 2×C—P), 136.2 (m, 2×C—P), 134.5 (d, J 23.3 Hz, 2×CH), 134.0 (2×CH), 133.9 (d, J 20.8 Hz, 4×CH), 130.9 (d, J 18.9 Hz, 2×CH), 130.1 (2×CH), 129.3 (2×CH), 128.9 (m, 2×C—P), 128.2 (d, J 13.4 Hz 4×CH), 128.2 (m, 2×CH), 128.1 (m, 2×CH), 123.5 (2×CH), 118.0 (2×CH), 21.4 (2×CH$_3$);

$^{31}$P-NMR (CDCl$_3$): δ −16.3

MS (EI, 70 eV) m/z: 566 (2, [M]$^+$), 565 (5, [M-H]$^+$), 489 (8, [M-Ph]$^+$), 475 (7, [M-(3-Me-Ph)]$^+$), 367 (100, [M-PPh (3-Me-Ph]$^+$), 199 (37, [PPh(3-Me-Ph)]$^+$);

HRMS (ESI) [M+H]$^+$: m/z calc.: for C$_{38}$H$_{33}$OP$_2$ 567.20012, found: 567.19973, [M+Na]$^+$: m/z calc.: for C$_{38}$H$_{32}$NaOP$_2$ 589.18206, found: 589.18202.

(1S,1'S)-(−)-(Oxybis(2,1-phenylene))bis((4-ethoxyphenyl)(phenyl)phosphine) (compound I-C.u)

Yield: 21%; white solid; m.p.=146-149° C. (from CC cyclohexane/EtOAc 49/1);

[α]$_D^{23}$=−1.9 (c1.0, CHCl$_3$);

$^1$H-NMR (CDCl$_3$): δ 7.30-7.09 (16H, m, arom. H), 6.94 (2H, dt, J 7.7, 1.1 Hz, arom. H), 6.85-6.75 (6H, m, arom. H), 6.72 (2H, arom. H), 4.01 (4H, q, J 6.9 Hz, 2×OCH$_2$), 1.40 (6H, t, J 6.9 Hz, 2×CH$_3$);

$^{13}$C-NMR (CDCl$_3$): δ 159.5 (2×C—OEt), 159.1 (d, J 117.8 Hz, 2×C—O), 137.2 (d, J 11.7 Hz, 2×C—P), 135.6 (d, J 22.3 Hz, 4×CH), 133.7 (2×CH), 133.5 (d, J 20.5 Hz, 4×CH), 130.0 (2×CH), 129.5 (d, J 15.4 Hz, 2×C—P), 128.1 (2×CH), 128.1 (d, J 7.6 Hz, 4×CH), 126.8 (m, 2×C—P), 123.4 (2×CH), 118.0 (2×CH), 114.5 (m, 4×CH), 63.2 (2×OCH$_2$), 14.8 (2×CH$_3$);

$^{31}$P-NMR (CDCl$_3$): δ −17.8 ppm;

MS (EI, 70 eV) m/z: 626 (6, [M]$^+$), 625 (10, [M-H]$^+$), 549 (8, [M-Ph]$^+$), 505 (5, [M-(4-EtO-Ph)]$^+$), 397 (100, [M-PPh(4-EtO-Ph)]$^+$;

HRMS (ESI) [M+H]$^+$: m/z calc.: for C$_{40}$H$_{37}$O$_3$P$_2$ 627.22124, found: 627.22094.

II. Application Examples

II.1.1 Asymmetric Hydrogenation at 25° C.

Example 4: Asymmetric Hydrogenation of Isophorone

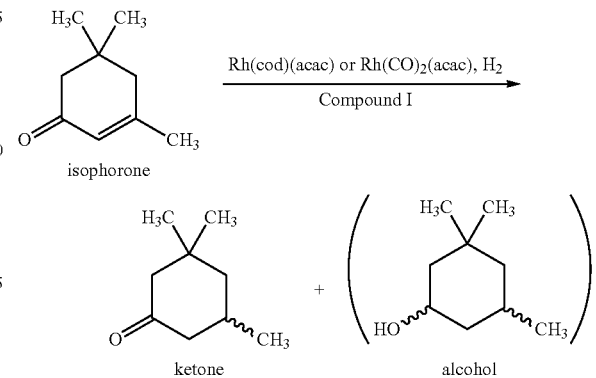

The hydrogenations were carried out in a parallel reactor apparatus (HPChemScan, HEL). In a glass vial with a Teflon-coated cross-blade stirrer, 5 μmol of rhodium complex and 1.2 equivalents of the compound of the formula I (1.2 eq., 6 μmol) as per table 1 were initially introduced. Then, the addition of the isophorone (1 mmol, 138 mg) was carried out from a stock solution in the corresponding solvent (0.33 M, 3 ml), i.e. substrate:rhodium:ligand=200:1:1.2, unless stated otherwise. The autoclaves were flushed in four cycles with argon (5 bar) and then with three cycles of hydrogen (10 bar) and heated to 40° C. at a pressure of 15 bar hydrogen. After reaching this internal temperature, the desired pressure (50 bar) was established and the hydrogenation was carried out isobarically over a period according to table 1 depending on the rhodium catalyst used. Then, the system was cooled. Following decompression, the autoclaves were flushed again with argon (5×5 bar).

Substrate:rhodium:ligand=200:1:1.2, unless emphasized otherwise.

The conversion was determined and the fractions of ketone and alcohol were ascertained by means of NMR spectroscopy. The ee values were ascertained by means of gas chromatography.

TABLE 1

Hydrogenation of isophorone

| Ligand of the compound | Rhodium complex | Solvent | Time [h] | Conversion [%] | Ketone % ee (product fraction) |
|---|---|---|---|---|---|
| I-A.a | Rh(CO)$_2$(acac) | THF | 4 | 100 | 84.0 (S) (97%) |
| I-A.a | Rh(CO)$_2$(acac) | Toluene | 20 | 100 | 84.9 (S) (81%) |
| I-B.a | Rh(CO)$_2$(acac) | THF | 4 | 100 | 79.9 (S) (98%) |
| I-B.a | Rh(CO)$_2$(acac) | Toluene | 20 | 100 | 77.4 (S) (95%) |
| I-C.a | Rh(CO)$_2$(acac) | THF | 4 | 97 | 50.5 (S) (99%) |
| I-C.a | Rh(CO)$_2$(acac) | Toluene | 4 | 100 | 59.3 (S) (99%) |
| I-A.b | Rh(CO)$_2$(acac) | THF | 4 | 100 | 96.5 (S) (99%) |
| I-A.b | Rh(CO)$_2$(acac) | Toluene | 4 | 100 | 96.4 (S) (99%) |
| I-A.b | Rh(acac)(cod) | Toluene | 15 | 70 | 50.1 (S) (98%) |
| I-A.e | Rh(CO)$_2$(acac) | THF | 4 | 84 | 91.2 (S) (98%) |
| I-A.e | Rh(CO)$_2$(acac) | Toluene | 4 | 87 | 91.9 (S) (98%) |
| I-A.g | Rh(CO)$_2$(acac) | THF | 4 | 89 | 91.9 (S) (98%) |
| I-A.g | Rh(CO)$_2$(acac) | Toluene | 4 | 89 | 91.9 (S) (98%) |
| I-B.k | Rh(CO)$_2$(acac) | THF | 4 | 98 | 83.5 (S) (95%) |
| I-B.k | Rh(CO)$_2$(acac) | Toluene | 8 | 100 | 85.1 (S) (99%) |

Examples 5-7

Hydrogenation of Neral and Geranial Under Standard Conditions

The individual hydrogenation experiments were carried out on a laboratory scale under the following conditions. In an autoclave (AK), the corresponding amounts of rhodium precursor [Rh(acac)(COD)] or Rh(acac)(CO)$_2$), compound of the formula I and neral or geranial are initially introduced and, by means of flushing several times, treated with argon under an inert atmosphere. Then, by means of a corresponding inlet valve, 7.5 ml of toluene are added by means of a syringe. The Ar atmosphere is exchanged for hydrogen by flushing several times. A hydrogen pressure of 1 bar at 25° C. was established. The reaction is terminated following expiry of the desired time for the hydrogenation of the first C═C bond in the neral or geranial or optionally after visible ending of the hydrogen absorption. Then, the hydrogen atmosphere was again automatically replaced by argon. The qualitative and quantitative evaluation of the reaction was carried out by means of NMR spectroscopy. The results are summarized in table 2.

Example 5: Asymmetric Hydrogenation of Neral

Condition: substrate, neral; Rh complex: 0.5 mmol of [Ru(acac)(cod)]; 2 equivalents of the compound I-A.b, 7.5 ml; toluene; 1 bar hydrogen pressure, 25° C.

Example 6: Asymmetric Hydrogenation of Neral

Conditions: substrate: neral; Rh precursor: Rh(acac)-(CO)$_2$; compound I-A.b, 7.5 ml toluene; 1 bar hydrogen pressure, 25° C.

Example 7: Asymmetric Hydrogenation of Geranial

Conditions: substrate: geranial; Rh complex: 0.5 mmol of [Ru(acac)(cod)]; 2 equivalents of the compound I-A.b, 7.5 ml; toluene; 1 bar hydrogen pressure, 25° C.

TABLE 2 asymmetric hydrogenation of neral and geranail under standard conditions

| Ex. | Substrate | Rh:compound I-A.b:substrate | Conversion [%] | Total runtime [min] | % ee Citronellal | Citronellal vs. Citronellol |
|---|---|---|---|---|---|---|
| 5 | Neral | 1:2:100 | 90 | 450 | 21.7 (S) | 97:3 |
| 6 | Neral | 1:2:200** | 96 | 210 | 21.3 (S) | 98:2 |
| 7 | Geranial | 1:2:100 | 88 | 440 | 17.2 (R) | 98:2 |

**Rh(acac)(CO)$_2$ as Rh precursor

II.2 Pd-Catalyzed Alkylation

Example 8: Pd-Catalyzed Alkylation of (±)-trans-1,3-diphenylallyl Acetate

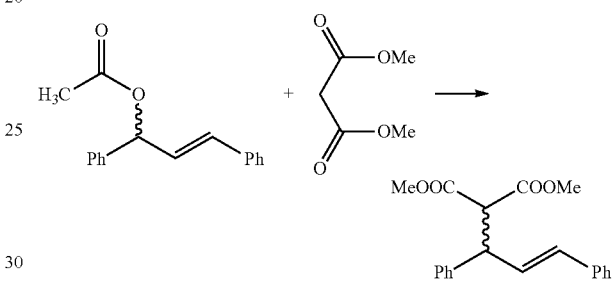

Dimethyl malonate (1 mmol, 132 mg), (±)-trans-1,3-diphenylallyl acetate (1 mmol, 252 mg) and lithium acetate (1 mmol, 66 mg) in 5 ml of 1,2-dichloroethane were initially introduced into a Schlenk vessel and cooled to approx. −20° C. Then, BSA (1 mmol, 203 mg) and Pd(dba)$_2$ complex (0.01 mmol, 5.75 mg) were added. The solution was stirred over a period of 24 hours and the temperature increased gradually to room temperature. For work-up, the mixture was treated with dichloromethane (20 ml) and washed with water (5 ml). After drying (Na$_2$SO$_4$) and evaporation on a rotary evaporator, the pure product was isolated by column chromatography (cyclohexane/EtOAc=19:1). The value for the enantiomer excess was provided by HPLC (Chiralpak IA (150×4.6 mm), hexane/i-PrOH=95/5, 1 ml/min, $t_R$=6.1 min (R)-enantiomer and $t_R$=7.3 min (S)-enantiomer).

TABLE 3

Results of the asymmetric alkylation of (±)-trans-1,3-diphenylallyl acetate

| Ligand | Yield [%] | ee [%] |
|---|---|---|
| I-A.a | 92 | 93.3 (R) |
| I-B.a | 92 | 88.6 (R) |
| I-C.a | 89 | 81.7 (R) |
| I-A.b | 82 | 90.4 (R) |
| I-B.b | 90 | 80.0 (R) |
| I-C.b | 91 | 64.9 (R) |
| I-A.e | 89 | 87.4 (R) |
| I-B.e | 88 | 90.2 (R) |
| | 96[b] | 88.7 (R) |
| | 91[a] | 88.8 (R) |
| | 90[c] | 88.8 (R) |
| I-C.e | 85 | 89.0 (R) |
| I-A.g | 88 | 87.9 (R) |
| | 91[b] | 88.5 (R) |
| I-B.g | 89 | 89.9 (R) |

TABLE 3-continued

Results of the asymmetric alkylation
of (±)-trans-1,3-diphenylallyl acetate

| Ligand | Yield [%] | ee [%] |
| --- | --- | --- |
| I-C.g* | 66[a] | 80.4 (S) |
|  | 90 | 71.0 (S) |
| I-A.h | 31[a] | 39.9 (R) |
|  | 90[b] | 36.4 (R) |
|  | 92 | 36.4 (R) |
| I-B.h | 86 | 46.1 (R) |
| I-C.h | 80 | 64.5 (R) |
| I-B.j | 79 | 45.2 (R) |
| I-C.j | 88 | 36.8 (R) |

[a]0.2 mmol of LiOAc;
[b]0.5 mmol of LiOAc;
0.1 mmol of LiOAc

The invention claimed is:
1. A chiral compound of the general formula (I)

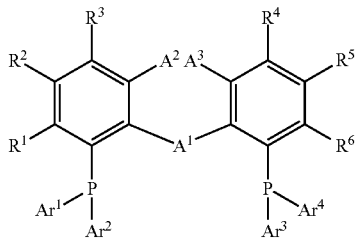

in which
$A^1$ is O, S, $CR^aR^b$, $NR^a$, $S(=O)$, $S(=O)_2$, $BR^a$, $PR^a$ or $P(=O)R^a$, where $R^a$ and $R^b$, independently of one another, are hydrogen, $C_1$-$C_{30}$-alkyl, $C_3$-$C_{12}$-cycloalkyl, heterocycloalkyl with 3 to 12 ring atoms, $C_6$-$C_{14}$-aryl or hetaryl with 5 to 14 ring atoms, where the cycloalkyl, heterocycloalkyl, aryl and hetaryl groups are unsubstituted or carrying one, two or three substituents selected from $C_1$-$C_{10}$-alkyl and $C_1$-$C_{10}$-alkoxy, $A^2$ and $A^3$, independently of one another, are hydrogen, $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-haloalkyl, hydroxy, mercapto, cyano, nitro, polyalkylene oxide, polyalkyleneimine, halogen, carboxyl, carboxylate, formyl, acyl, sulfo, sulfonate or $NE^1E^2$, in which $E^1$ and $E^2$ are in each case identical or different radicals selected from hydrogen, $C_1$-$C_{30}$-alkyl, $C_3$-$C_{12}$-cycloalkyl and $C_6$-$C_{14}$-aryl, or
$A^2$ and $A^3$ together are a chemical bond between the two benzene rings, or
$A^2$ and $A^3$ together are O, S, $CR^cR^d$, $NR^c$, $SiR^cR^d$, $S(=O)$, $S(=O)_2$, $BR^c$, $PR^c$ or $P(=O)R^c$, where $R^c$ and $R^d$, independently of one another, are hydrogen, $C_1$-$C_{30}$-alkyl, $C_3$-$C_{12}$-cycloalkyl, heterocycloalkyl with 3 to 12 ring atoms,
$C_6$-$C_{14}$-aryl or hetaryl with 5 to 14 ring atoms, where cycloalkyl, heterocycloalkyl, aryl and hetaryl groups are unsubstituted or carry one, two or three substituents selected from $C_1$-$C_{10}$-alkyl or $C_1$-$C_{10}$-alkoxy, or
$A^1$, $A^2$ and $A^3$ together are a bridging group

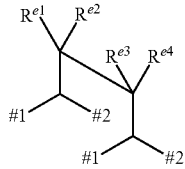

where
each of the variables #1 and #2 is a binding site, where the binding sites #1 are bonded to two adjacent carbon atoms of the one benzene ring and the binding sites #2 are bonded to two adjacent carbon atoms of the other benzene ring,
$R^{e1}$, $R^{e2}$, $R^{e3}$ and $R^{e4}$, independently of one another, are hydrogen, $C_1$-$C_{20}$-alkyl, $C_3$-$C_{12}$-cycloalkyl, $C_6$-$C_{14}$-aryl, halogen, trifluoromethyl, carboxyl or carboxylate,
where $R^{e1}$, also together with $R^{e3}$, can be the binding fraction of a double bond between the two carbon atoms to which $R^{e1}$ and $R^{e3}$ are bonded, or
$R^{e1}$, $R^{e2}$, $R^{e3}$ and $R^{e4}$ together with the carbon atoms of the bridging group to which they are bonded can also be a benzene ring or a condensed aromatic ring system with 1, 2 or 3 benzene rings, where the benzene rings are unsubstituted or where each of the benzene rings can have 1 or 2 substituents which are selected, independently of one another, from $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-haloalkyl, hydroxy, mercapto, cyano, nitro, polyalkylene oxide, polyalkyleneimine, halogen, carboxyl, carboxylate, formyl, acyl, sulfo, sulfonate or $NE^3E^4$, in which $E^3$ and $E^4$ are in each case identical or different radicals selected from hydrogen, $C_1$-$C_{30}$-alkyl, $C_3$-$C_{12}$-cycloalkyl and $C_6$-$C_{14}$-aryl, $Ar^1$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_3$-$C_{12}$-cycloalkyl and $C_6$-$C_{14}$-aryl, $Ar^2$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_3$-$C_{12}$-cycloalkyl and $C_6$-$C_{14}$-aryl, $Ar^3$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_3$-$C_{12}$-cycloalkyl and $C_6$-$C_{14}$-aryl, $Ar^4$ is $C_6$-$C_{14}$-aryl or hetaryl with 5 to 14 ring atoms, where aryl and hetaryl are unsubstituted or carry 1, 2 or 3 identical or different substituents which are selected from $C_1$-$C_6$-alkyl, $C_1$-$C_6$-alkoxy or $NE^5E^6$, in which $E^5$ and $E^6$ are in each case identical or different radicals selected from hydrogen, $C_1$-$C_{30}$-alkyl, $C_3$-$C_{12}$-cycloalkyl and $C_6$-$C_{14}$-aryl, with the proviso that $Ar^1$ and $Ar^2$ do not have the same meaning, and that $Ar^3$ and $Ar^4$ do not have the same meaning, $R^1$, $R^2$, $R^3$, $R^4$, $R^5$ and $R^6$, independently of one another, are hydrogen, $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-halo alkyl, hydroxy, mercapto, cyano, nitro, polyalkylene oxide, polyalkyleneimine, halogen, carboxyl, carboxylate, formyl, acyl, sulfo, sulfonate or $NE^5E^6$, in which $E^5$ and $E^6$ are in each case identical or different radicals selected from hydrogen, $C_1$-$C_{20}$-alkyl, $C_3$-$C_{12}$-cycloalkyl and $C_6$-$C_{14}$-aryl, where two adjacent radicals $R^1$ to $R^6$, together with the carbon atoms of the benzene ring to which they are bonded, can also be a condensed ring system with 1, 2 or 3 further benzene rings, where the benzene rings of the condensed ring system are unsubstituted or each of the benzene rings can have 1 or 2 substituents which are selected, independently of one another, from $C_1$-$C_{20}$-alkyl, $C_1$-$C_{20}$-alkoxy, $C_3$-$C_{12}$-cycloalkyl, $C_3$-$C_{12}$-cycloalkyloxy, heterocycloalkyl with 3 to 12 ring atoms, heterocycloalkyloxy with 3 to 12 ring atoms, $C_6$-$C_{14}$-aryl, $C_6$-$C_{14}$-aryloxy, hetaryl with 5 to 14 ring atoms, hetaryloxy with 5 to 14 ring atoms, $C_1$-$C_{20}$-hydroxyalkyl, $C_1$-$C_{20}$-aminoalkyl, $C_1$-$C_{20}$-halo alkyl, hydroxy, mercapto, cyano, nitro, polyalkylene oxide, polyalkyleneimine, halogen, carboxyl, carboxylate, formyl, acyl, sulfo, sulfonate or $NE^7E^8$, in which $E^7$ and $E^8$ are in each case identical or different radicals selected from hydrogen, $C_1$-$C_{20}$-alkyl, $C_3$-$C_{12}$-cycloalkyl and $C_6$-$C_{14}$-aryl.

2. The chiral compound according to claim 1, where
$A^1$ is O and $A^2$ and $A^3$ are a chemical bond between the benzene rings, or
$A^1$ is O and $A^2$ and $A^3$ together are $CR^cR^d$, where $R^c$ and $R^d$, independently of one another, are hydrogen or $C_1$-$C_4$-alkyl, or
$A^1$ is O and $A^2$ and $A^3$ are both hydrogen.

3. The chiral compound according to claim 1, where $R^1$, $R^2$, $R^3$, $R^4$, $R^5$ and $R^6$, independently of one another, are selected from hydrogen, $C_1$-$C_{20}$-alkyl and $C_1$-$C_{20}$-alkoxy.

4. The chiral compound according to claim 1, where two of the radicals $R^1$, $R^2$, $R^3$, $R^4$, $R^5$ and $R^6$ are $C_1$-$C_{20}$-alkyl or $C_1$-$C_{20}$-alkoxy, and the others are hydrogen.

5. The chiral compound according to claim 1, where $Ar^1$, $Ar^2$, $Ar^3$ and $Ar^4$, independently of one another, are selected from phenyl, 1-naphthyl, 2-naphthyl, 9-phenanthryl, 2-tolyl, 3-tolyl, 4-tolyl, 2-ethylphenyl, 3-ethylphenyl, 2-isopropylphenyl, 3-isopropylphenyl, 4-(2-methylbutyl)phenyl, 2-anisyl, 3-anisyl, 4-anisyl, 2-ethoxyphenyl, 4-ethoxyphenyl, 3-ethoxyphenyl, 2-isopropoxyphenyl, 3-isopropoxyphenyl, 3,5-dimethoxyphenyl and dibenzo[b,d]-furan-4-yl.

6. The chiral compound according to claim 1, where $Ar^2$ and $Ar^4$ are both 1-naphthyl, 2-naphthyl, 9-phenanthryl, 2-tolyl, 3-tolyl, 4-tolyl, 2-ethylphenyl, 3-ethylphenyl, 2-isopropylphenyl, 3-isopropylphenyl, 4-(2-methylbutyl)phenyl, 2-anisyl, 3-anisyl, 4-anisyl, 2-ethoxyphenyl, 4-ethoxyphenyl, 3-ethoxyphenyl, 2-isopropoxyphenyl, 3-isopropoxyphenyl, 3,5-dimethoxyphenyl or dibenzo[b,d]-furan-4-yl.

7. A chiral catalyst comprising at least one transition metal complex which has at least one chiral compound of the general formula (I) as defined in claim 1 as ligands.

8. A process for preparing a chiral compound of the general formula (I) as defined in claim 1, in which
a) a compound of the general formula (I.a)

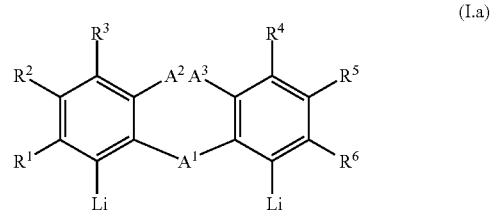

(I.a)

is provided, in which $A^1$, $A^2$, $A^3$, $R^1$, $R^2$, $R^3$, $R^4$, $R^5$ and $R^6$ have the meanings given in claim 1,
b) a compound of the general formula (I.b1) is provided and, if $Ar^1$ and $Ar^3$ and $Ar^2$ and $Ar^4$ do not have the same meaning, a compound of the general formula (I.b2) is provided

A.

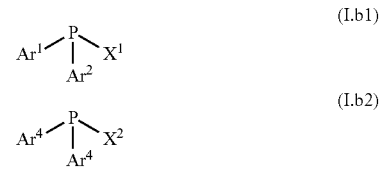

in which
$Ar^1$, $Ar^2$, $Ar^3$ and $Ar^4$ have the meanings given in claim 1, and
$X^1$ and $X^2$, independently of one another, are $C_1$-$C_4$-alkoxy,
and
c) the compound of the general formula (I.a) is reacted with the compound of the general formula (I.b1) and, if present, with the compound of the general formula (I.b2), to give a compound of the general formula (I).

9. The process according to claim 8, where, for providing the compounds of the general formula (I.b1) and, if $Ar^1$ and $Ar^3$ and $Ar^2$ and $Ar^4$ do not have the same meaning, (I.b2) in step b):
b1) an optically active ephedrine composition is subjected to a reaction with a compound of the general formula $Ar^1$—$P(N(C_1$-$C_4$-alkyl$)_2)_2$ and a borane adduct to give an optically active compound of the general formula (III)

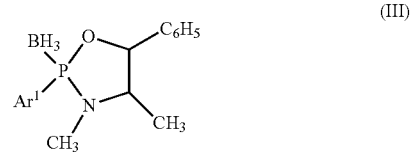

(III)

b2) the compound of the general formula (III) is subjected to a reaction with an aryllithium compound $Ar^2$—Li and then a proton donor to give an optically active compound of the general formula (IV)

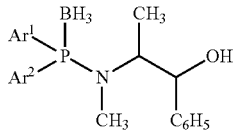
(IV)

b3) the compound of the general formula (IV) is subjected to a reaction with a $(C_1$-$C_4)$-alkanol to give an optically active compound of the general formula (V)

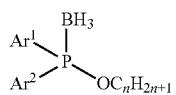
(V)

where n=1-4 b4) the compound of the general formula (V) is subjected to a reaction with a Lewis base to give an optically active compound of the general formula (I.b1)

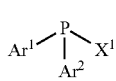
(I.b1)

in which $X^1$ is $C_1$-$C_4$-alkoxy, where, for preparing a compound of the general formula (I.b2) in which $X^2$ is $C_1$-$C_4$-alkoxy, the reaction steps b1) to b4) are carried out with the proviso that, in step b1), an optically active ephedrine composition is subjected to a reaction with a compound of the general formula $Ar^a$—P(N($C_1$-$C_4$-alkyl)$_2$)$_2$ and a borane adduct and that, in step b2), the compound of the general formula (III) is subjected to a reaction with an aryl-lithium compound $Ar^4$—Li.

10. A process for preparing chiral compounds by reacting a prochiral compound which comprises at least one ethylenically unsaturated double bond in the presence of a chiral catalyst comprising at least one transition metal complex with at least one compound of the general formula (I) as defined in claim 1 as ligands.

11. The process according to claim 10, which is a hydrogenation, allylic alkylation, hydroformylation, hydrocyanation, carbonylation, hydroacylation, hydroamidation, hydroesterification, hydrosilylation, hydroboration, aminolysis, alcoholysis, isomerization, metathesis, cyclopropanation or aldol condensation.

12. A process for preparing an optically active carbonyl compound by asymmetric hydrogenation of a prochiral α,β-unsaturated carbonyl compound with hydrogen in the presence of at least one optically active transition metal catalyst that is soluble in the reaction mixture and which has rhodium as catalytically active transition metal and a chiral compound of the general formula (I) as defined in claim 1 as ligands.

13. The process according to claim 12, where the prochiral α,β-unsaturated carbonyl compound is selected from compounds of the general formula (II)

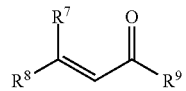
(II)

in which $R^7$, $R^8$ are different from one another and in each case is an unbranched, branched or cyclic hydrocarbon radical having 1 to 25 carbon atoms which is saturated or has one or more nonconjugated ethylenic double bonds, and which is unsubstituted or carries one or more identical or different substituents which are selected from $OR^{10}$, $NR^{11a}R^{11b}$, halogen, $C_6$-$C_{10}$-aryl and hetaryl with 5 to 10 ring atoms, $R^9$ is hydrogen or an unbranched, branched or cyclic hydrocarbon radical having 1 to 25 carbon atoms which is saturated or has one or more nonconjugated ethylenic double bonds, and which is unsubstituted or carries one or more identical or different substituents which are selected from $OR^{10}$, $NR^{11a}R^{11b}$, halogen, $C_6$-$C_{10}$-aryl and hetaryl with 5 to 10 ring atoms, or $R^9$ together with one of the radicals $R^7$ or $R^8$ can also be a 3- to 25-membered alkylene group in which 1, 2, 3 or 4 nonadjacent $CH_2$ groups can be replaced by O or N—$R^{11c}$, where the alkylene group is saturated or has one or more nonconjugated ethylenic double bonds, and where the alkylene group is unsubstituted or carries one or more identical or different substituents which are selected from $OR^{10}$, $NR^{11a}R^{11b}$, halogen, $C_1$-$C_4$-alkyl, $C_6$-$C_{10}$-aryl and hetaryl with 5 to 10 ring atoms, where two substituents can also together be a 2- to 10-membered alkylene group, where the 2- to 10-membered alkylene group is saturated or has one or more nonconjugated ethylenic double bonds, and where the 2- to 10-membered alkylene group is unsubstituted or carries one or more identical or different substituents which are selected from $OR^{10}$, $NR^{11a}R^{11b}$, halogen, $C_6$-$C_{10}$-aryl and hetaryl with 5 to 10 ring atoms;

where $R^{10}$ is hydrogen, $C_1$-$C_6$-alkyl, $C_6$-$C_{10}$-aryl, $C_6$-$C_{14}$-aryl-$C_1$-$C_{10}$-alkyl, or $C_1$-$C_{10}$-alkyl-$C_6$-$C_{14}$-aryl;

$R^{11a}$, $R^{11b}$ are in each case independently of one another hydrogen, $C_1$-$C_6$-alkyl, $C_6$-$C_{10}$-aryl, $C_6$-$C_{14}$-aryl-$C_1$-$C_{10}$-alkyl or $C_1$-$C_{10}$-alkyl-$C_6$-$C_{14}$-aryl; or $R^{11a}$ and $R^{11b}$ can together also be an alkylene chain having 2 to 5 carbon atoms which can be interrupted by N or O; and $R^{11c}$ is hydrogen, $C_1$-$C_6$-alkyl, $C_6$-$C_{10}$-aryl, $C_6$-$C_{14}$-aryl-$C_1$-$C_{10}$-alkyl or $C_1$-$C_{10}$-alkyl-$C_6$-$C_{14}$-aryl.

14. The process according to claim 12, where the prochiral α,β-unsaturated carbonyl compound is selected from compounds of the general formulae (IIa) and (IIb)

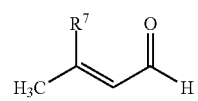
(IIa)

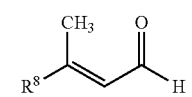
(IIb)

in which

R⁷, R⁸ is in each case an unbranched or branched hydrocarbon radical having 2 to 25 carbon atoms which is saturated or has 1, 2, 3, 4 or 5 nonconjugated ethylenic double bonds.

15. The process according to claim 14 for preparing optically active citronellal of the formula (VI)

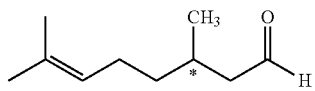
(VI)

in which * designates the asymmetry center, by asymmetric hydrogenation of geranial of the formula (IIa-1) or of neral of the formula (IIb-1)

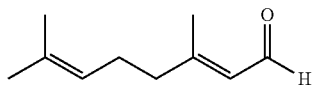
(IIa-1)

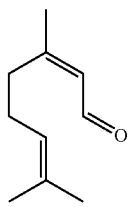
(IIb-1)

or a mixture comprising neral and geranial.

16. A process for preparing optically active menthol, in which optically active citronellal of the formula (VI), according to claim 15, is subjected to a cyclization to give optically active isopulegol, and the optically active isopulegol is hydrogenated to give optically active menthol.

17. The chiral compound according to claim 1, wherein Ar² and Ar⁴, independently of one another, are selected from phenyl, 1-naphthyl, 2-naphthyl, 9-phenanthryl, 2-tolyl, 3-tolyl, 4-tolyl, 2-ethylphenyl, 3-ethylphenyl, 2-isopropylphenyl, 3-isopropylphenyl, 4-(2-methylbutyl)phenyl, 2-anisyl, 3-anisyl, 4-anisyl, 2-ethoxyphenyl, 4-ethoxyphenyl, 3-ethoxyphenyl, 2-isopropoxyphenyl, 3-isopropoxyphenyl, 3,5-dimethoxyphenyl and dibenzo[b,d]-furan-4-yl, and wherein Ar¹ and Ar³ are both phenyl.

18. A chiral catalyst consisting of at least one transition metal complex which has at least one chiral compound of the general formula (I) as defined in claim 1 as ligands.

* * * * *